United States Patent [19]
Nelson

[11] 3,933,897

[45] Jan. 20, 1976

[54] PGA$_1$-OXA-PHENYLENE COMPOUNDS

[75] Inventor: Norman A. Nelson, Galesburg, Mich.

[73] Assignee: The Upjohn Company, Kalamazoo, Mich.

[22] Filed: July 18, 1974

[21] Appl. No.: 489,849

Related U.S. Application Data

[63] Continuation-in-part of Ser. No. 302,567, Oct. 30, 1972, abandoned, which is a continuation-in-part of Ser. No. 121,572, March 5, 1971, abandoned.

[52] U.S. Cl... 260/473 A; 260/211 R; 260/247.2 R; 260/268 R; 260/293.8; 260/326.2; 260/429.9; 260/439 R; 260/448 R; 260/468 D; 260/473 G; 260/501.1; 60/501.15; 260/501.17; 260/501.2; 260/514 D; 260/520

[51] Int. Cl.$^2$.................. C07C 65/22; C07C 69/76
[58] Field of Search............. 260/473 A, 473 G, 520

[56] References Cited
FOREIGN PATENTS OR APPLICATIONS
784,809   12/1972   Belgium............................ 260/468

Primary Examiner—Robert Gerstl
Attorney, Agent, or Firm—Morris L. Nielsen

[57] ABSTRACT

This invention is a group of PGA$_1$-type oxa-phenylene compounds, and processes for making them. These compounds are useful for a variety of pharmacological purposes, including anti-ulcer, treatment of asthma, and management of renal dysfuction.

30 Claims, No Drawings

PGA₁-OXA-PHENYLENE COMPOUNDS

CROSS REFERENCE TO RELATED APPLICATIONS

This application is a continuation-in-part of my copending application Ser. No. 302,567, filed Oct. 30, 1972, which was a continuation-in-part of my then copending application Ser. No. 121,572, filed Mar. 5, 1971 both now abandoned.

BACKGROUND OF THE INVENTION

This invention relates to compositions of matter, and to methods and intermediates for producing them. In particular, the several aspects of this invention relate to novel oxa-phenylene analogs of some of the known prostaglandins, for example prostaglandin $E_1$ ($PGE_1$), prostaglandin $E_2$ ($PGE_2$), prostaglandin $F_1$ ($PGF_1$ $\alpha$ and $PGF_1$ $\beta$), prostaglandin $F_2$ ($PGF_2$ $\alpha$ and $PGF_2$ $\beta$), prostaglandin $A_1$ ($PGA_1$), prostaglandin $A_2$ ($PGA_2$), prostaglandin $B_1$ ($PGB_1$), prostaglandin $B_2$ ($PGB_2$), the corresponding $PG_3$'s, and the dihydro $PG_1$ derivatives, to novel methods for producing those novel prostaglandin analogs, and to novel chemical intermediates useful in those novel methods.

Each of the above-mentioned known prostaglandins is a derivative of prostanoic acid which has the following structure and atom numbering:

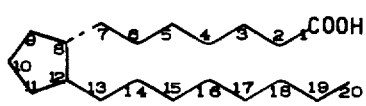

I

A systematic name for prostanoic acid is 7-[(2β-octyl)-cyclopent-1α-yl] heptanoic acid.

$PGE_1$ has the following structure:

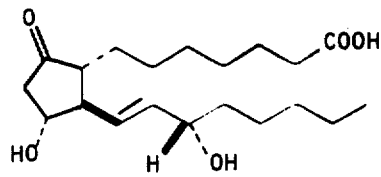

II $PGF_1$ $\alpha$ has the following structure:

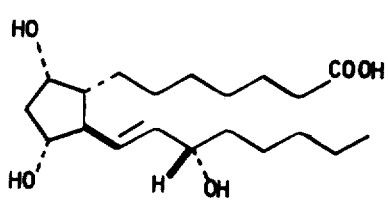

III $PGF_1$ $\beta$ has the following structure:

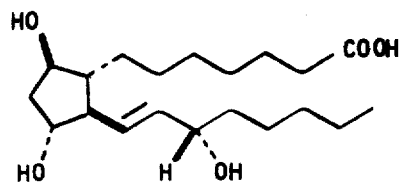

IV $PGA_1$ has the following structure:

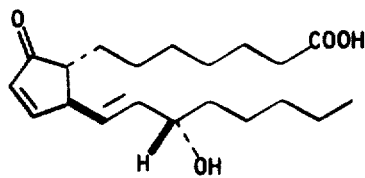

V $PGB_1$ has the following structure:

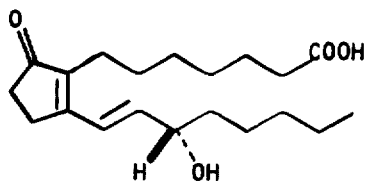

VI

Each of the known prostaglandins $PGE_2$, $PGF_2$ $\alpha$, $PGF_2$ $\beta$, $PGA_2$, and $PGB_2$ has a structure the same as that shown for the corresponding $PG_1$ compound except that in each, C-5 and C-6 are linked with a cis carbon-carbon double bond. For example, $PGE_2$ has the following structure:

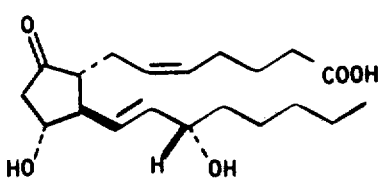

VII

Each of the known $PG_3$ prostaglandins has a structure the same as that of the $PG_2$ compounds except that in each, C-17 and C-18 are linked with a cis carbon-carbon double bond. For example, $PGE_3$ has the following structure:

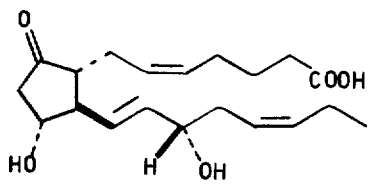

VIII

Each dihydro derivative of $PGE_1$, $PGF_1$ $\alpha$, $PGF_1$ $\beta$, $PGA_1$, and $PGB_1$ has a structure the same as that shown for the corresponding $PG_1$ compound except that in each, C-13 and C-14 are linked with a carbon-carbon single bond. For example, dihydro-$PGE_1$ has the following structure:

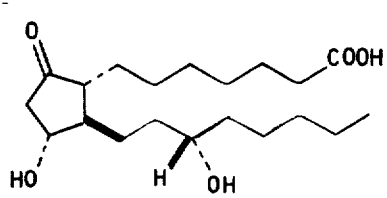

IX

The prostaglandin formulas mentioned above each have several centers of asymmetry. As drawn, formulas II to IX each represents the particular optically active form of the prostaglandin obtained from certain mammalian tissues, for example, sheet vesicular glands, swine lung, and human seminal plasma, or by reduction or dehydration of a prostaglandin so obtained. See, for example, Bergstrom et al., Pharmacol. Rev. 20, 1 (1968), and references cited therein. The mirror image of each formula represents a molecule of the enantiomer of that prostaglandin. The racemic form of the prostaglandin consists of equal numbers of two types of molecules, one represented by one of the above formulas and the other represented by the mirror image of that formula. Thus, both formulas are needed to define a racemic prostaglandin. See Nature 212, 38 (1966) for discussion of the stereochemistry of the prostaglandins.

In formulas I-IX, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

Prostaglandins with carboxyl-terminated side chains attached to the cyclopentane ring in beta configuration are also known. These are derivatives of 8-iso-prostanoic acid which has the following formula:

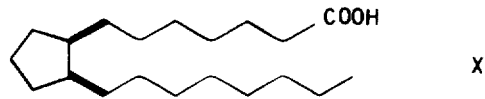

X

A systematic name for 8-iso-prostanoic acid is 7-[(2β-octyl)-cyclopent-1β-yl] heptanoic acid.

The side-chain hydroxy at C-15 in formulas II to IX is in alpha (S) configuration. See Nature 212, 38 (1966) for discussion of the stereochemistry of the prostaglandins.

PGE$_1$, PGE$_2$, dihydro-PGE$_1$, and the corresponding PGF$_\alpha$, PGF$_\beta$, PGA, and PGB compounds, and their esters, acylates, and pharmacologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological responses are stimulation of smooth muscle as shown, for example, by tests of strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decreasing blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments.

Because of these biological responses; these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application.

The PGE, PGF$_\alpha$, PGF$_\beta$, and PGA compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, ephedrine, etc); xanthine derivatives (theophylline and aminophylline); and corticosteroids (ACTH and predinisolone). Regarding use of these compounds see South African Pat. No. 681,055.

The PGE and PGA compounds are useful in mammals, including man and certain useful animals, e.g., dogs and pigs, to reduce and control excessive gastric secrection, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, PGF$_\alpha$, and PGF$_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, PGF $_\alpha$, and PGF $_\beta$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, PGE$_2$, for example, is useful in place of or in combination with less than usual amounts of these known smooth muscle stimulators, for example, to relieve the symptoms of paralytic ileus, or to control or prevent antonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50$\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE, PGF $_\alpha$, and PGF $_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50$\mu$g. per kg. of body weight per minute until or near the termination of the second stage of labor, i.e., expulsion of the fetus. These compounds are especially useful when the female is one or more weeks post-mature and natural labor has not started, or 12 or 60 hours after the membranes have ruptured and natural labor has not yet started. An alternative route of administration is oral.

The PGE, PGF $_\alpha$, and PGF $_\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose PGF$_2$ $_\alpha$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGA compounds and derivatives and salts thereof increase the flow of blood in the mammalian kidney, thereby increasing volume and electrolyte content of the urine. For that reason, PGA compounds are useful in managing cases of renal dysfunction, especially those involving blockage of the renal vascular bed. Illustratively, the PGA compounds are useful to alleviate and correct cases of edema resulting, for example, from massive surface burns, and in the management of shock. For these purposes, the PGA compounds are preferably first administered by intravenous injection at a dose in the range of 10 to 1000$\mu$g. per kg. of body weight or by intravenous infusion at a dose in the range 0.1 to 20$\mu$g. per kg. of body weight per minute until the desired effect is obtained. Subsequent doses are given by intravenous, intramuscular, or subcutaneous injection or infusion in the range 0.05 to 2 mg. per kg. of body weight per day.

The PGE and PGB compounds promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the cite where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 µg./ml. of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

The PGE and PGF compounds are useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by PGE and PGF compounds is useful in assisting sperm movement to the uterus. Cervical dilation by prostaglandins is also useful in operative gynecology such as D and C (Cervical Dilation and Uterine Curettage) where mechanical dilation may cause performation of the uterus, cervical tears, or infections. It is also useful in diagnostic procedures where dilation is necessary for tissue examination. For these purposes, the PGE and PGF compounds are administered locally or systemically. $PGE_2$, for example, is administered orally or vaginally at doses of about 5 to 50 mg. per treatment of an adult female human, with from one to five treatments per 24 hour period. $PGE_2$ is also administered intramuscularly or subcutaneously at doses of about one to 25 mg. per treatment. The exact dosages for these purposes depend on the age, weight, and condition of the patient or animal.

The PGE, $PGF_\alpha$, $PGF_\beta$, PGA, and PGB compounds are useful in reducing the undesirable gastrointestinal effects resulting from systemic administration of anti-inflammatory prostaglandin synthetase inhibitors, and are used for that purpose by concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including $PGE_1$, $PGE_2$, $PGE_3$, 13,14-dihydro-$PGE_1$, and the corresponding 11-deoxy-PGE and PGA compounds.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration. The prostaglandin is administered along with the anti-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally or, alternatively, orally or, in the case of women vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered.

SUMMARY OF THE INVENTION

It is a purpose of this invention to provide novel oxa-phenylene prostaglandin analogs, and process for making them.

The novel prostaglandin analogs of this invention each have an oxa oxygen (—O—) and a divalent phenylene moiety

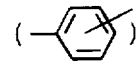

in the carboxyl-terminated side chain of the prostanoic acid structure (I) or the 8-iso-prostanoic acid structure (X). These divalent groups are located between the carboxyl group and the cyclopentane ring, and are either in addition to the six methylene portions of said chain or in place of one to five of said methylene portions. Bonding to the phenylene ring is either ortho, meta, or para. The oxa group is between the phenylene moiety and the carboxyl group.

Some of the novel prostaglandin analogs of this invention also have, in addition, a benzene ring as part of the C-13 to C-20 chain of the prostanoic acid structure (I) or 8-iso-prostanoic acid structure (X). That benzene ring is present as a substituted or unsubstituted phenyl moiety attached as a substituent to one of the methylenes between C-15 and the terminal methyl of the prostanoic acid or 8-isoprostanoic acid structure. Alternatively, the substituted or unsubstituted phenyl moiety is attached to the terminal or omega carbon of the C-16 to C-20 portion of the chain, replacing one of the hydrogens of the terminal methyl, the entire terminal methyl, or the terminal methyl plus one to four of the methylenes adjacent to that terminal methyl.

For example, five of the novel prostaglandin analogs of this invention are represented by the formulas:

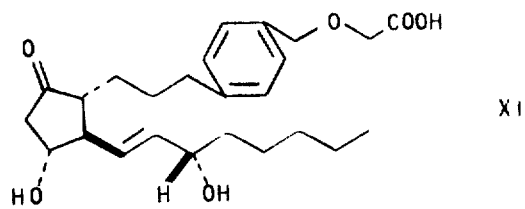

XI

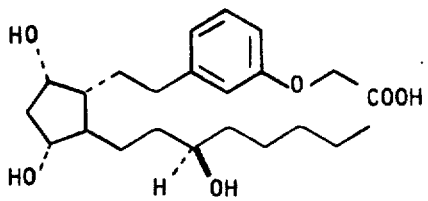

XII

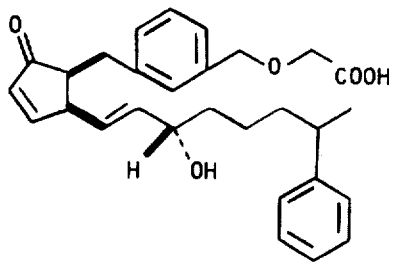

XIII

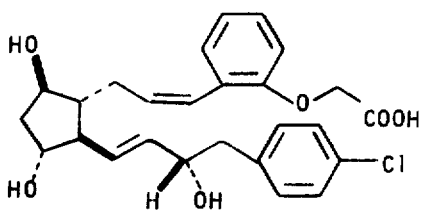

XIV

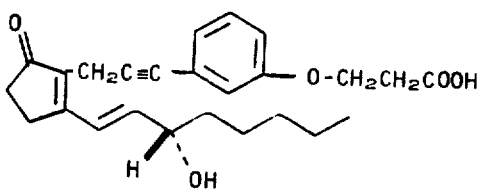

XV

Based on its relationship to PGE₁ and prostanoic acid, the compound of formula XI is named 3-oxa-4,5-inter-p-phenylene-PGE₁. Similarly, the compound of formula XII is named 15(R)-3-oxa-3,6-inter-m-phenylene-4,5-dinor-13,14-dihydro-PGF₁ α , the compound of formula XIII is named 8-iso-3-oxa-19-phenyl-4,7-inter-m-phenylene-5,6-dinor-PGA₁, the compound of the formula XIV is named 3-oxa-16-(4-chloro-phenyl)-3,5-inter-o-phenylene-4,17,18,19,20-pentanor-PGF₂ β , and the compound of formula XV is named 5,6-dehydro-4-oxa-4,5-inter-m-phenylene-PGB₂.

These names for the compounds of formulas XI to XV are typical of the names used hereinafter for the novel compounds of this invention. These names can better be understood by reference to the structure and numbering system of prostanoic acid (Formula I, above). That formula has seven carbon atoms in the carboxy-terminated chain and eight carbon atoms in the hydroxy-containing chain. In these names, "3-oxa" and "4-oxa" indicate an oxa oxygen (—O—) in place of the 3-methylene and 4-methylene, respectively of the PG compound.

The use of "nor," "dinor," "trinor," "tetranor," "pentanor," "hexanor," and the like in the names for the novel compounds of this invention indicates the absence of one or more of the chain carbon atoms and the attached hydrogen atoms. The number or numbers in front of nor, dinor, etc., indicate which of the original prostanoic acid carbon atoms are missing in the named compound.

Each of the names of the novel compounds of this invention contains (inter-p-phenylene), (inter-m-phenylene), or (inter-o-phenylene), preceded by two numbers. That indicates that p-phenylene, m-phenylene, or o-phenylene has been inserted between (inter) the two carbon atoms so numbered in the formula of prostanoic acid.

Thus, formula XIII differs from prostanoic acid in that an oxa oxygen replaces carbon 3, carbons 5 and 6 of prostanoic acid are missing, m-phenylene has been inserted between carbons 4 and 7 of prostanoic acid, and a phenyl has been attached to carbon 19 of prostanoic acid. Formula XIII also, of course, is an A type prostaglandin, having a carbonyl oxygen and a 10:11 double bond.

Novel compounds of this invention with the carboxyl-terminated chain attached to the cyclopentane ring in beta configuration are 8-iso compounds (formula X), and are so designated by using "8-iso" in the name. An example is the name given above for the compound of formula XIII. If 8-iso does not appear in the name, attachment of the carboxy-terminated chain in alpha configuration is to be assumed.

Novel compounds of this invention with epi configuration for the hydroxy at C-15 are so designated by using "15(R)" in the name. See, for example, the name given above for the formula-XII compound. Alternately, "15-beta" is used. See. R. S. Cahn, Journal of Chemical Education Vol. 41, page 116 (1964) for a discussion of S and R configurations. If "15(R)" or "15-beta" does not appear in the name, the natural configuration for the C-15 hydroxy, identified as the "S" configuration for PGE₁, is to be assumed.

Some of the novel compounds of this invention differ structurally in other ways from the known prostanoic acid derivatives, having for example, more or fewer carbon atoms in either chain, and having one or more alkyl and/or fluoro substituents in the chains.

The following formulas represent the novel oxaphenylene compounds of this invention.

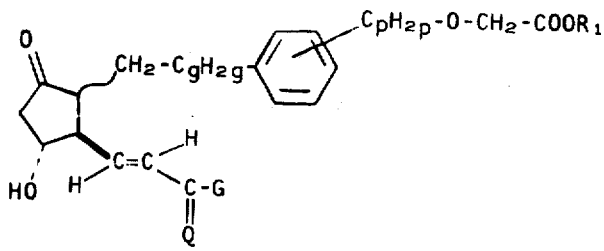

XVI

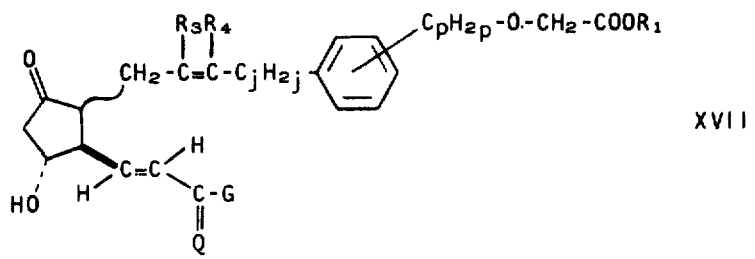
XVII
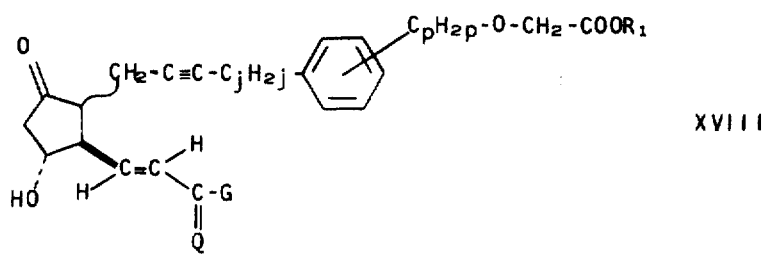
XVIII
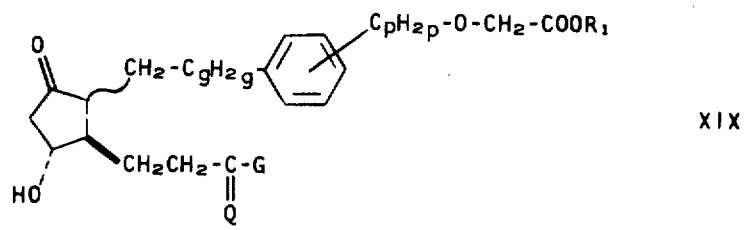
XIX
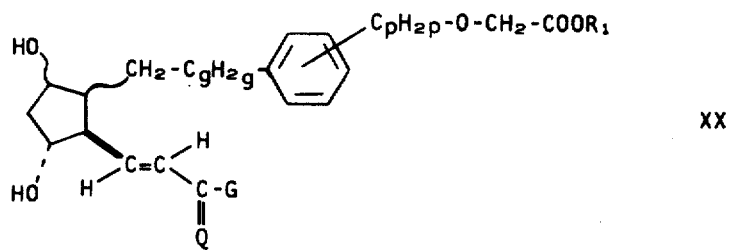
XX
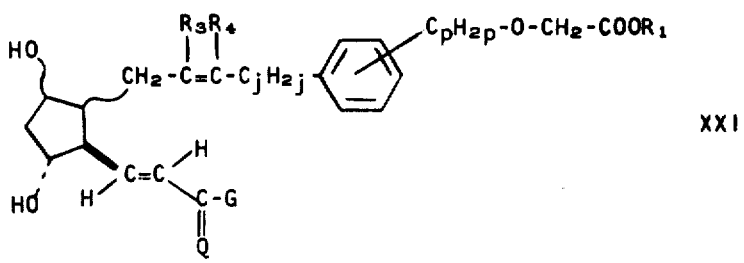
XXI
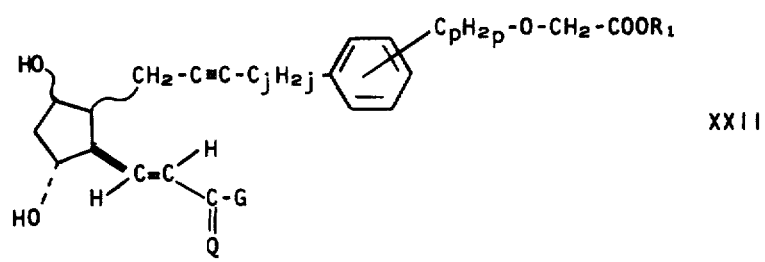
XXII

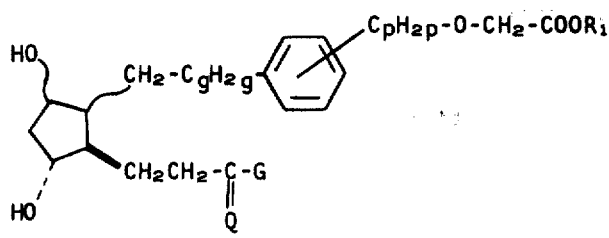
XXIII
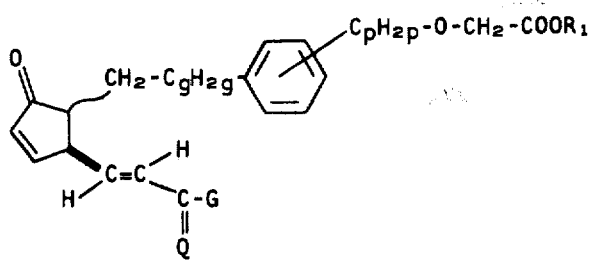
XXIV
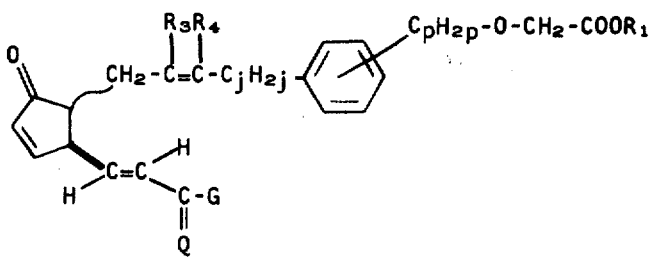
XXV
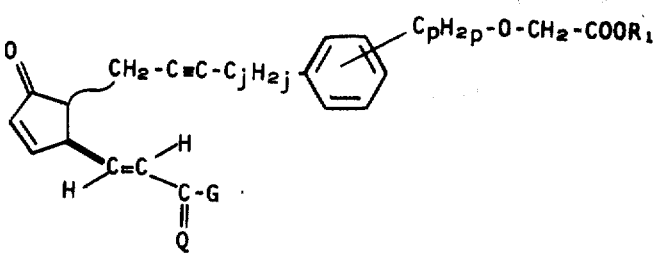
XXVI
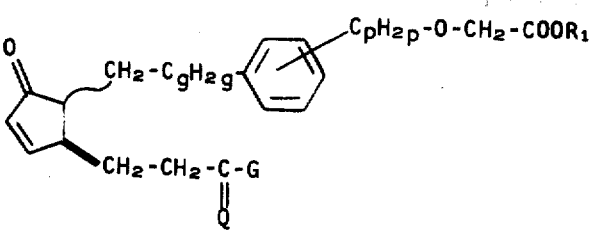
XXVII
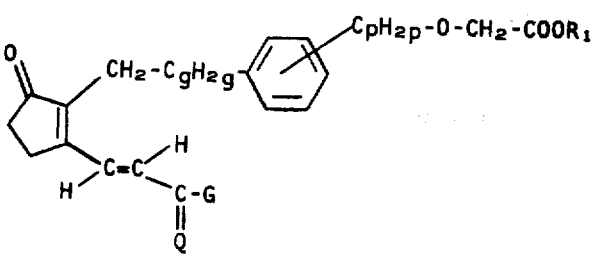
XXVIII

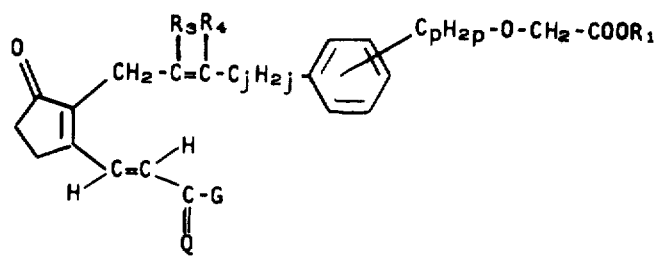
XXIX
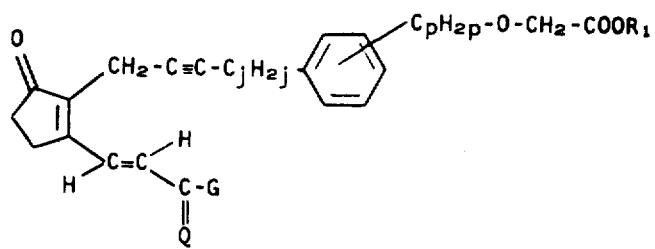
XXX
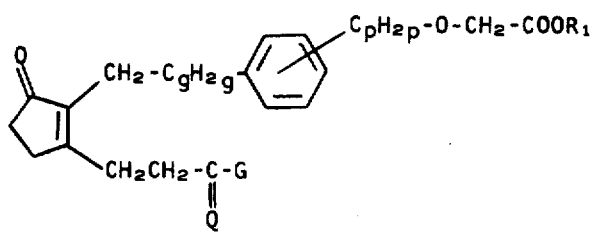
XXXI
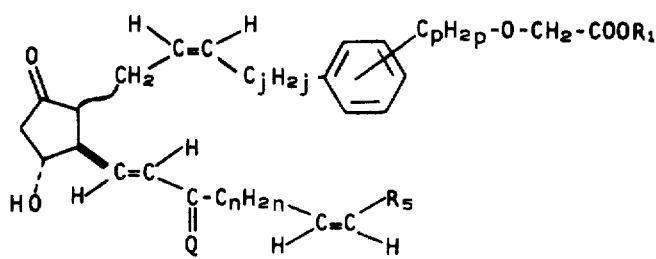
XXXII
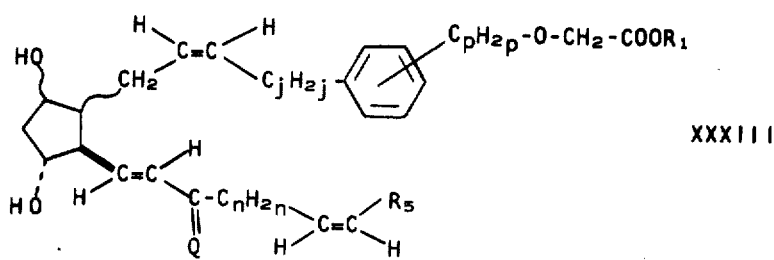
XXXIII
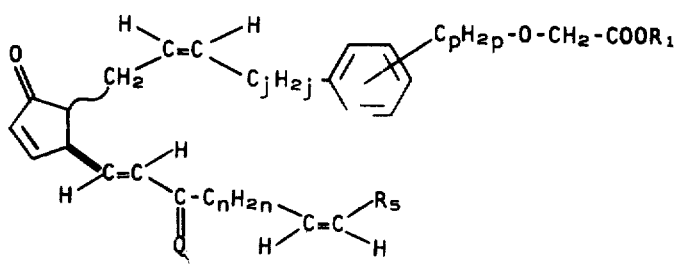
XXXIV

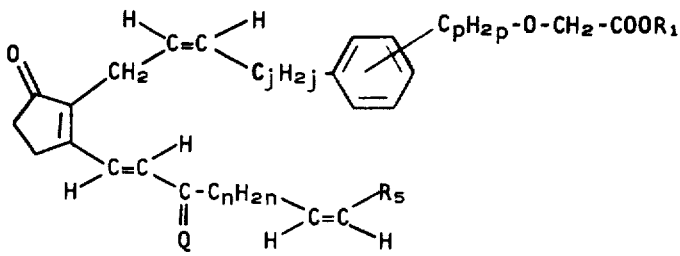

XXXV

Formulas XVI–XIX, and XXXII represent oxa-phenylene compounds of the PGE type. Formulas XX-XXIII, and XXXIII represent oxa-phenylene compounds of the PGF type. Formulas XXIV-XXVII, and XXXIV represent oxa-phenylene compounds of the PGA type. Formulas XXVIII-XXXI, and XXXV represent oxa-phenylene compounds of the PGB type.

In formulas XVI to XXXV, the wavy line ~ indicates attachment of the hydroxyl or the side chain to the cyclopentane ring in alpha or beta configuration;

G is (1) alkyl of 2 to 10 carbon atoms, inclusive, substituted with zero, one, 2, or 3 fluoro or (2) a monovalent moiety of the formula

wherein $C_tH_{2t}$ represents a valence bond or alkylene of 1 to 10 carbon atoms, inclusive, substituted with zero, one, or 2 fluoro, with one to 7 carbon atoms, inclusive, between

and the ring, wherein T is alkyl of one to 4 carbon atoms, inclusive, fluoro, chloro, trifluoromethyl, or —$OR_6$, wherein $R_6$ is hydrogen or alkyl of one to 4 carbon atoms, inclusive, and wherein s is zero, one, 2, or 3, with the proviso that not more than two T's are other than alkyl, $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro, 2 or 3 bromo, or 1, 2, or 3 iodo; Q is

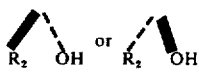

wherein $R_2$ is hydrogen or alkyl of one to 4 carbon atoms, inclusive; $R_3$ and $R_4$ are hydrogen or methyl; and $R_5$ is alkyl of one to 4 carbon atoms, inclusive, substituted with zero, one, 2, or 3 fluoro.

Likewise, in formulas XVI to XXXV, $C_gH_{2g}$ represents a valence bond or alkylene of one to 4 carbon atoms, inclusive, with one or 2 chain carbon atoms between —$CH_2$— and the ring; $C_jH_{2j}$ represents a valence bond or alkylene of one or 2 carbon atoms with one chain carbon atom between the chain unsaturation and the ring; $C_nH_{2n}$ is alkylene of one to 4 carbon atoms, inclusive; $C_pH_{2p}$ represents a valence bond or alkylene of one to 4 carbon atoms, inclusive, with one or 2 chain carbon atoms between the ring and —O—, wherein $C_gH_{2g}$ and $C_pH_{2p}$ together represent zero to 8 carbon atoms, inclusive, with total chain lengths zero to 3 carbon atoms, inclusive, and wherein $C_jH_{2j}$ and $C_pH_{2p}$ together represent zero to 6 carbon atoms, inclusive, with total chain lengths zero to 3 carbon atoms, inclusive.

Regarding the meaning of $C_gH_{2g}$, $C_jH_{2j}$, and $C_pH_{2p}$ as defined above, the novel compounds of this invention include compounds wherein a carbon atom of the phenylene moiety is attached directly to the C-7 methylene or the C-5 = $CR_4$ —in ortho, meta, or para orientation relative to the oxa-containing portion of the carboxyl chain. When $C_gH_{2g}$ represents alkylene, the chain of carbon atoms which connects the C-7 methylene to a carbon atom of phenylene will be one or 2 carbon atoms long. When $C_jH_{2j}$ represents alkylene, the chain of carbon atoms which connects =$CR_4$— to a carbon atom of phenylene will be one carbon atom long. $C_pH_{2p}$ represents a valence bond or alkylene of one to 6 carbon atoms, inclusive, with one or 2 carbon atoms between the ring and the —O—. Any or all of these alkylene chains are unsubstituted or substituted with alkyl carbons in the form of one or more alkyl groups within the total carbon content of each chain as specified above, i.e., a maximum of 4 carbon atoms of $C_gH_{2g}$, 2 carbons for $C_jH_{2j}$, and 4 carbons for $C_pH_{2p}$. When $C_gH_{2g}$ or $C_jH_{2j}$ is alkylene, it is the same as or different than $C_pH_{2p}$, 8 carbon atoms being the maximum total carbon content and 3 carbon atoms being the maximum total chain length for the combination of $C_gH_{2g}$ and $C_pH_{2p}$, and 6 carbon atoms being the maximum total carbon content and 3 carbon atoms being the maximum total chain length for the combination of $C_jH_{2j}$ and $C_pH_{2p}$. To illustrate these definitions, when $C_gH_{2g}$ is ethylene, $C_pH_{2p}$ is methylene, or one of them is a valence bond and the other is ethylene, but both are not ethylene. In this first illustration, where the total chain length of $C_gH_{2g}$ and $C_pH_{2p}$ is 3 carbon atoms, up to 5 carbon atoms are in the alkyl substituents.

Formulas XVI through XXXV include the separate isomers wherein Q is either

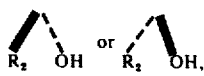

i.e. where the hydroxyl is in either alpha (natural) or beta configuration. Referring to the prostanoic acid atom numbering (formula I above), the point of attachment corresponds to C-15, and, herein, regardless of the variation in the C-1 to C-7 carboxy chain, these epimers are referred to as "C-15 epimers".

Formulas XX–XXIII, and XXXIII wherein the C-9 hydroxyl (following prostanoic acid atom numbering) is attached to the cyclopentane with a wavy line ~ include both PGF$_\alpha$ - and PGF$_\beta$ -type compounds.

Included in Formulas XVII, XXI, XXV, and XXIX, are both the cis and the trans compounds with respect to the C-5 to C-6 double bonds in the carboxyl-terminated side chain. In all of the compounds containing the $C_{13}$ to $C_{14}$ double bond, that double bond is in trans configuration, and the chain containing that moiety is attached to the cyclopentane ring in beta configuration in compounds encompassed by formulas XVI to XXXV.

The novel oxa-phenylene compounds of this invention include racemic compounds and both optically active enantiomeric forms thereof. As discussed hereinabove, two structural formulas are required to define accurately these racemic compounds. The formulas as drawn herein are intended to represent compounds with the same configuration as the naturally-occurring prostaglandins. However, for convenience in the charts herein only a single structural formula is used, for example in Chart D, to define not only the optically active form but also the racemic compounds which generally undergo the same reactions.

Formula XVI represents 3-oxa-4,5-inter-p-phenylene-PGE$_1$ (formula XI hereinabove) when $C_oH_{2o}$ is ethylene, $C_pH_{2p}$ is methylene, G is n-pentyl, Q is

$R_1$ is hydrogen, $C_oH_{2o}$ and $C_pH_{2p}$ are attached to the phenylene in para orientation, and the carboxyl-terminated side chain is attached to the cyclopentane ring in alpha configuration.

With regard to formulas XVI to XXXV, examples of alkyl of one to 4 carbon atoms, inclusive, or methyl, ethyl, propyl, butyl, and isomeric forms thereof. Examples of alkyl of 1 to 8 carbon atoms, inclusive, are those given above, and pentyl, hexyl, heptyl, octyl, and isomeric forms thereof. Examples of alkyl of one to 12 carbon atoms, inclusive, are those given above, and nonyl, decyl, undecyl, dodecyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 3-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of alkyl of two to 10 carbon atoms, inclusive, substituted with one to 3 fluoro, are 2-fluoroethyl, 2-fluorobutyl, 3-fluorobutyl, 4-fluorobutyl, 5-fluoropentyl, 4-fluoro-4-methylpentyl, 3-fluoroisoheptyl, 8-fluorooctyl, 3,4-difluorobutyl, 4,4-difluoropentyl, 5,5-difluoropentyl, 5,5,5-trifluoropentyl, and 10,10,10-trifluorodecyl.

Examples of alkylene within the various scopes of $C_oH_{2o}$, $C_jH_{2j}$, $C_pH_{2p}$, $C_nH_{2n}$, and $C_tH_{2t}$, as those are defined above, are methylene, trimethylene, tetramethylene, pentamethylene, hexamethylene, and heptamethylene, and those alkylene with one or more alkyl substituents on one or more carbon atoms, thereof, e.g., —CH(CH$_3$)—, —C(CH$_3$)$_2$—, —CH(CH$_2$CH$_3$)—, —CH$_2$—CH(CH$_3$)—, —CH(CH$_3$)—CH(CH$_3$)—, —CH$_2$—C(CH$_3$)$_2$—, —CH$_2$—CH(CH$_3$)—CH$_2$—, —CH$_2$—CH$_2$—CH(CH$_2$CH$_3$)—, —CH(CH$_3$)—CH(CH$_3$)—CH$_2$—CH$_2$—, —CH$_2$—CH$_2$—CH$_2$—C(CH$_3$)$_2$—CH$_2$—, —CH$_2$—CH$_2$—CH$_2$—CH$_2$—CH(CH$_3$)—, —CH$_2$—CH$_2$—CH$_2$—CH$_2$—CH$_2$—C(CH$_3$)$_2$—, —CH(CH$_3$)—CH$_2$—CH(CH$_3$)—CH$_2$—CH$_2$—CH(CH$_3$)—, and —CH$_2$—CH$_2$—CH$_2$—CH$_2$—CH$_2$—CH$_2$—C(CH$_3$)$_2$—.

Examples of alkylene substituted with one or 2 fluoro and within the scope of $C_tH_{2t}$, as defined above, are —CHF—CH$_2$—, CHF—CHF—, —CH$_2$—CH$_2$—CF$_2$—, —CH$_2$—CHF—CH$_2$—, —CH$_2$—CH$_2$—CF(CH$_3$)—, —CH$_2$—CH$_2$—CH$_2$—CF$_2$—, and —CHF—CH$_2$—CH$_2$—CH$_2$—CH$_2$—CH$_2$—.

Examples of

as defined above are phenyl, p-tolyl, m-tolyl, o-tolyl, p-fluorophenyl, m-fluorophenyl, o-fluorophenyl, p-chlorophenyl, m-chlorophenyl, o-chlorophenyl, p-trifluoromethylphenyl, m-trifluoromethylphenyl, p-trifluoromethylphenyl, p-hydroxyphenyl, m-hydroxyphenyl, o-hydroxyphenyl, p-methoxyphenyl, m-methoxyphenyl, o-methoxyphenyl, p-tetrahydropyranyloxyphenyl, m-tetrahydropyranyloxyphenyl, o-tetrahydropyranyloxyphenyl, o-ethylphenyl, m-isopropylphenyl, p-tert-butylphenyl, p-butoxyphenyl, 3,4-dimethylphenyl, 2,4-diethylphenyl, 2,4,6-trimethylphenyl, 3,4,5-trimethylphenyl, 2,4-dichlorophenyl, 3,4-difluorophenyl, 2-chloro-4-methylphenyl, 2-fluoro-4-methoxyphenyl, 3,5-dimethyl-4-fluorophenyl, 2,6-dimethyl-4-hydroxyphenyl, and 2,4-di(trifluoromethyl)phenyl.

The novel formula XVI-XIX, and XXXII PGE-type oxa-phenylene compounds, the novel formula XX-XXIII, and XXXIII PGF$_\alpha$-type and PGF$_\beta$-type oxa-phenylene compounds, the novel formula XXIV-XXVII, and XXXIV PGA-type oxa-phenylene compounds, and the novel formula XXVIII-XXXI, and XXXV PGB-type oxa-phenylene compounds each cause the biological responses described above for the PGE, PGF$_\alpha$, PGF$_\beta$, PGA, and PGB compounds, respectively, and each of these novel compounds is accordingly useful for the above-described corresponding purposes, and is used for those purposes in the same manner as described above.

The known PGE, PGF$_\alpha$, PGF$_\beta$, PGA, and PGB compounds uniformly cause multiple biological responses even at low doses. For example, PGE$_1$ and PGE$_2$ both cause vasodepression and smooth muscle stimulation at the same time they exert antilipolytic activity. Moreover, for many applications, these known prostaglandins have an inconveniently short duration of biological activity. In striking contrast, the novel prostaglandin analogs of formulas XVI to XXXV are substantially more specific with regard to potency in causing prostaglandin-like biological responses, and have a substantially longer duration of biological activity. Therefore, each of these novel prostaglandin analogs is useful in place of one of the corresponding above-mentioned known prostaglandins for at least one of the pharmacological purposes indicated above for the latter, and is surprisingly and unexpectedly more useful for that purpose because it has a different and narrower spectrum of biological activity than the known prostaglandin, and therefore is more specific in its activity and causes smaller and fewer undesired side effects than the known prostaglandin. Moreover, because of its prolonged activity, fewer and smaller doses of the novel prostaglandin analog can frequently be used to attain the desired result.

To obtain the optimum combination of biological response specificity, potency, and duration of activity, certain compounds within the scope of formulas XVI to XXXV are preferred. For example, in compounds of formulas XVI, XIX, XX, XXIII, XXIV, XXVII, XXVIII, and XXXI, it is preferred that the carboxyl-terminated side chain contain a total of 2 to 4 chain carbon atoms, inclusive, excluding the phenylene and $-COOR_1$, and including the C-7 methylene. In other words, preferred compounds of these formulas are those wherein $C_oH_{2o}$ and $C_pH_{2p}$ together represent zero, one, or 2 chain carbon atoms. Especially preferred compounds of these formulas are those wherein $C_oH_{2o}$ and $C_pH_{2p}$ each represent a valence bond, and those wherein $C_oH_{2o}$ represents a valence bond and $C_pH_{2p}$ represents a single chain carbon atom, especially methylene.

In compounds of formulas XVII, XVIII, XXI, XXII, XXV, XXVI, XXIX, XXX, XXXII, XXXIII, XXXIV, and XXXV, it is preferred that the carboxyl-terminated side chain contain a total of 4 or 5 chain carbon atoms, excluding the phenylene and $-COOR_1$, and including $-CH_2-CR_3=CR_4-$ and $-CH_2-C\equiv C-$. In other words, preferred compounds of these formulas are those wherein $C_jH_{2j}$ and $C_pH_{2p}$ together represent zero or one chain carbon atoms. Included in these coumpounds are those wherein $C_jH_{2j}$ and $C_pH_{2p}$ each represent a valence bond, and those wherein $C_jH_{2j}$ represents a valence bond, and $C_pH_{2p}$ represents a single chain carbon atom, especially methylene.

As used herein, a chain carbon atom is part of the direct chain carbon atoms linking the C-7 methylene or $=CR_4-$ to the phenylene, the phenylene to the oxa, and the oxa to $-COOR_1$. Thus, the chain $-CH(CH_3)-C(CH_3)_2-$ contains 5 carbon atoms but only 2 chain atoms.

Another preference for the carboxy-terminated side chain in compounds of formulas XVI to XXXV is that the phenylene be a meta-phenylene.

Another preference for the compounds of formulas XVI to XXXV is that $R_2$, $R_3$, and $R_4$ are hydrogen or methyl. All of those R groups can be hydrogen, all can be methyl, or there can be any of the possible combinations of hydrogen and methyl.

Certain variations in the nature of G in the compounds of formulas XVI to XXXV are especially important. In the known $PG_1$ and $PG_2$ prostaglandins, e.g., $PGE_1$, the portion of the molecule corresponding to G in formulas XVI to XXXI is n-pentyl. When G is unsubstituted alkyl or fluoro-substituted alkyl as defined above, there is a preference which results in compounds with optimum combinations of biological properties: namely that G is straight chain alkyl of 3 to 7 carbon atoms, inclusive, with or without a fluoro substituent at the 1-position, e.g., $-CHF-(CH_2)_a-CH_3$, wherein $a$ is one, 2, 3, 4, or 5. Especially preferred among these are n-pentyl and 1-fluoropentyl.

When G is substituted alkyl, it is preferred that the 1-position be mono- or di-substituted with one or two alkyl groups containing from one to 4 carbon atoms, inclusive. Especially preferred are formula XVI-to-XXXV compounds wherein G is substituted at the 1-position with methyl and/or ethyl, e.g. $-CH(CH_3)-(CH_2)_c-CH_3$, $-CH(C_2H_5)-(CH_2)_c-CH_3$, $-C(CH_3)_2-(CH_2)_c-CH_3$, $-C(C_2H_5)_2-(CH_2)_c-CH_3$, or $-C(CH_3)(C_2H_5)-(CH_2)_c-CH_3$, wherein $c$ is 2, 3, or 4.

When G represents

as defined above, it is preferred for compounds with optimum combination of biological properties that $C_tH_{2t}$ be a valence bond, i.e., $t$ is zero, or alkylene of one to 4 carbon atoms, inclusive, i.e., $-(CH_2)_d-$ wherein $d$ is one, 2, 3, or 4, with or without a fluoro or alkyl substituent on the carbon adjacent to the hydroxy-substituted carbon (C-15 in $PGE_1$), e.g., $-CHF-(CH_2)_e-$, $-CH(CH_3)-(CH_2)_e-$, or $-C(CH_3)_2-(CH_2)_e-$, wherein $e$ is zero, one, 2, or 3. Further, it is preferred that the phenyl ring when present and substituted, be substituted at least at the para position.

In compounds of formulas XXXII to XXXV, it is preferred that $C_nH_{2n}$ be methylene and that $R_5$ be ethyl.

Another way of expressing the above preferences for G is that when G is alkyl or fluoro-substituted alkyl it be a group represented by

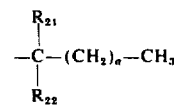

wherein $a$ is one, 2, 3, 4, or 5, and wherein $R_{21}$ and $R_{22}$ are hydrogen, alkyl of one to 4 carbon atoms, inclusive, or fluoro, being the same or different, with the proviso that $R_{22}$ is fluoro only when $R_{21}$ is hydrogen or fluoro.

Furthermore, when G is

it is preferred that when $C_tH_{2t}$ is alkylene or fluoro-substituted alkylene it be a group represented by

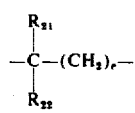

wherein $e$ is zero, one, 2, or 3, and wherein $R_{21}$ and $R_{22}$ are as defined above.

Still another preference is that Q be

wherein $R_2$ is as defined hereinabove.

Another advantage of the novel compounds of this invention, especially the preferred compounds defined hereinabove, compared with the known prostaglandins, is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

The PGE, PGF$_\alpha$, PGF$_\beta$, PGA, and PGB type oxa-phenylene compounds encompassed by formulas XVI to XXXV including the special classes of compounds described above, are used for the purposes described above in the free acid form, in ester form, or in pharmacologically acceptable salt form. When the ester form is used, the ester is any of those within the above definition of $R_1$. However it is preferred that the ester be alkyl of one to 12 carbon atoms, inclusive. Of those alkyl, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of these formula XVI-to-XXXV compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, n-butylethanolamine, 2-amino-1-butanol, 2-amino-2-ethyl-1,3-propanediol, 2-amino-2-methyl-1-propanol, tris-(hydroxymethyl)aminomethane, N-phenylethanolamine, N-(p-tert-amylphenyl)-diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The PGE, PGF$_\alpha$, PGF$_\beta$, PGA, and PGB type oxa-phenylene compounds encompassed by formulas XVI to XXXV including the special classes of compounds described above, are also used for the purposes described above in free hydroxy form or in the form wherein the hydroxy moieties are transformed to lower alkanoate moieties, e.g., —OH to —OCOCH$_3$. Examples of lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

As discussed above, the compounds of formulas XVI to XXXV are administered in various ways for various purposes; e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For that purpose, it is preferred because of increased water solubility that $R_1$ in the formula XVI-to-XXXV compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The PGE, PGF$_\alpha$, PGF$_\beta$, PGA and PGB type oxa-phenylene compounds encompassed by formulas XVI to XXXV are produced by the reactions and procedures described and exemplified hereinafter.

The various PGF$_\alpha$-type and PGF$_\beta$-type oxa-phenylene compounds encompassed by formulas XX–XXIII and XXXIII are prepared by carbonyl reduction of the corresponding PGE type compounds encompassed by formulas XVI–XIX and XXXII. For example, carbonyl reduction of 3-oxa-3,7-inter-m-phenylene-4,5,6-trinor-PGE$_1$ gives a mixture of 3-oxa-3,7-inter-m-phenylene-4,5,6-trinor-PGF$_{1\alpha}$ and 3-oxa-3,7-inter-m-phenylene-4,5,6-trinor-PGF$_{1\beta}$.

These ring carbonyl reductions are carried out by methods known in the art for ring carbonyl reductions of known prostanoic acid derivatives. See, for example, Bergstrom et al., Arkiv Kemi 19, 563 (1963), Acta Chem. Scand. 16, 969 (1962), and British Patent Specification No. 1,097,533. Any reducing agent is used which does not react with carbon-carbon double bonds or ester groups. Preferred reagents are lithium(tri-tert-butoxy)aluminum hydride, the metal borohydrides, especially sodium, potassium and zinc borohydrides, and metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et al., J. Biol. Chem. 240, 457 (1965), and Green et al., J. Lipid Research 5, 117 (1964). Especially preferred as separation methods are partition chromatographic procedures, both normal and reversed phase, preparative thin layer chromatography, and countercurrent distribution procedures.

The various PGA-type oxa-phenylene compounds encompassed by formulas XXIV–XXVII and XXXIV are prepared by acidic dehydration of the corresponding PGE type compounds encompassed by formulas XVI–XIX and XXXII. For example, acidic dehydration of 3-oxa-3,7-inter-m-phenylene-4,5,6-trinor-PGE$_1$ gives 3-oxa-3,7-inter-m-phenylene-4,5,6-trinor-PGA$_1$.

These acidic dehydrations are carried out by methods known in the art for acidic dehydrations of known prostanoic acid derivatives. See, for example, Pike et al., Proc. Nobel Symposium II, Stockholm (1966), Interscience Publishers, New York, pp. 162–163 (1967); and British Patent Specification No. 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent, e.g., tetrahydrofuran, are also useful as reagents for this acidic dehydration, although these reagents may cause partial hydrolysis of an ester reactant.

The various PGB-type oxa-phenylene compounds encompassed by formulas XXVIII–XXXI and XXXV are prepared by basic dehydration of the corresponding PGE type compounds encompassed by formulas XVI–XIX and XXXII, or by contacting the corresponding PGA type compounds encompassed by formulas XXIV–XXVII and XXXIV with base. For example, both 3-oxa-3,7-inter-m-phenylene-4,5,6-trinor-PGE$_1$ and 3-oxa-3,7-inter-m-phenylene-4,5,6-trinor-PGA$_1$ give 3-oxa-3,7-inter-m-phenylene-4,5,6-trinor-PGB$_1$ on treatment with base.

These basic dehydrations and double bond migrations are carried out by methods known in the art for similar reactions of known prostanoic acid derivatives. See, for example, Bergstrom et al., J. Biol. Chem. 238, 3555 (1963). The base is any whose aqueous solution has pH greater than 10. Preferred bases are the alkali metal hydroxides. A mixture of water and sufficient of a water-miscible alkanol to give a homogeneous reaction mixture is suitable as a reaction medium. The PGE-type or PGA-type compound is maintained in such a reaction medium until no further PGB-type compound is formed, as shown by the characteristic ultraviolet light absorption near 278 m$\mu$ for the PGB type compound.

The various transformations of PGE-type oxa-phenylene compounds of formulas XVI-XIX to the corresponding PGF $\alpha$, PGF $\beta$, PGA and PGB type oxa-phenylene compounds are shown in Chart A, wherein G, Q, R$_1$, and ~ are as defined above, wherein E' is —CH$_2$CHR$_9$— or trans—CH=CR$_9$—, wherein R$_{28}$ and R$_9$ are hydrogen or alkyl of one to 4 carbon atoms, inclusive, and wherein J' is

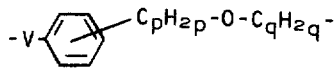

wherein V is C$_s$H$_{2s}$, cis or trans

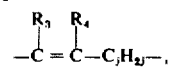

or —C≡C—C$_j$H$_{2j}$ wherein C$_s$H$_{2s}$, C$_j$H$_{2j}$, C$_p$H$_{2p}$, R$_3$, and R$_4$ are as defined above, and wherein C$_q$H$_{2q}$ represents alkylene of one to 6 carbon atoms, inclusive, with one, 2, or 3 carbon atoms between —O— and —COOR$_1$.

The various 13,14-dihydro-PGE$_1$, -PGF$_1$, -PGA$_1$, and -PGB$_1$ type oxa-phenylene compounds encompassed by formulas XIX, XXIII, XXVII, and XXXI are prepared by carbon-carbon double bond reduction of the corresponding PGE, PGF, PGA, and PGB type compound containing a trans double bond in the hydroxy-containing side chain. A cis or trans double bond or a triple bond can also be present in the carboxy-terminated side chain of the unsaturated reactant, and will be reduced at the same time to —CH$_2$CH$_2$—. For example, 13,14-dihydro-3-oxa-3,7-inter-m-phenylene-4,5,6-trinor-PGE$_1$ is produced by reduction of 3-oxa-3,7-inter-m-phenylene-4,5,6-trinor-PGE$_1$, 3-oxa-3,7-inter-m-phenylene-4,5,6-trinor-PGE$_2$, or 5,6-dehydro-3-oxa-3,7-inter-m-phenylene-4,5,6-trinor-PGE$_2$.

These reductions are carried out by reacting with the unsaturated PGE, PGF $\alpha$, PGF $\beta$, PGA, or PGB type oxa-phenylene compound with diimide, following the general procedure described by van Tamelen et al., J. Am. Chem. Soc. 83, 3725 (1961).

CHART A

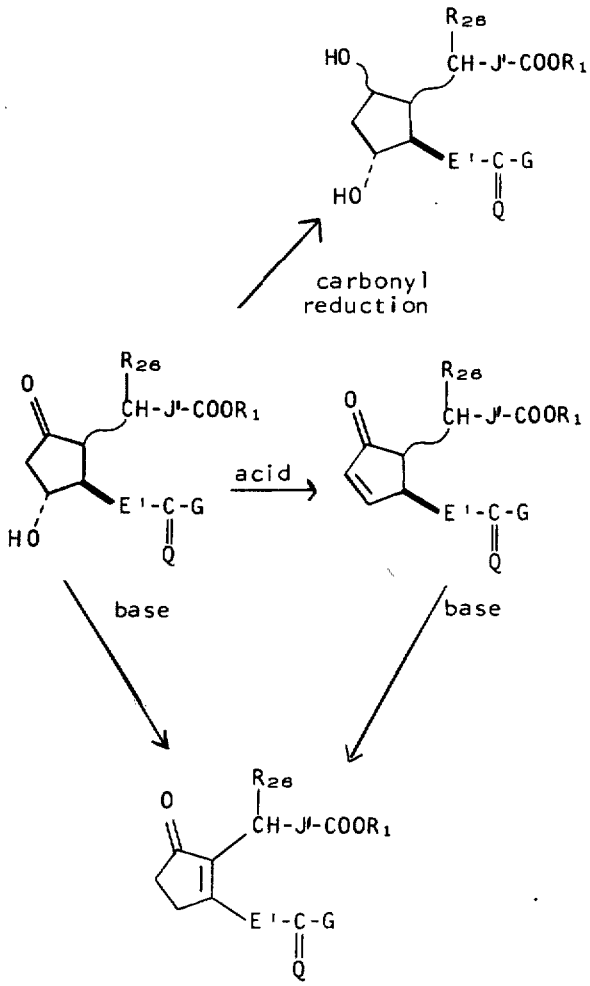

See also Fieser et al., "Topics in Organic Chemistry," Reinhold Publishing Corp., New York, pp. 432–434 (1963) and references cited therein. The unsaturated acid or ester reactant is mixed with a salt of azodiformic acid, preferably an alkali metal salt such as the disodium or dipotassium salt, in the presence of an inert diluent, preferably a lower alkanol such as methanol or ethanol, and preferably in the absence of substantial amounts of water. At least one molecular equivalent of the azodiformic acid salt is used for each multiple bond equivalent of the unsaturated reactant. The resulting suspension is then stirred, preferably with exclusion of oxygen, and the mixture is made acid, advantageously with a carboxylic acid such as acetic acid. When a reactant wherein $R_1$ is hydrogen is used, the carboxylic acid reactant also serves to acidify an equivalent amount of the azodiformic acid salt. A reaction temperature in the range of about 10° to about 40° C. is usually suitable. Within that temperature range, the reaction is usually complete within less than 24 hours. The desired dihydro production is then isolated by conventional methods, for example, evaporation of the diluent, followed by separation from inorganic materials by solvent extraction.

In the case of the oxa-phenylene unsaturated PGE, PGF $\alpha$, and PGF $\beta$ type reactants, the reductions to the corresponding dihydro-PGE$_1$, dihydro-PGF$_1$ $\alpha$, and dihydro-PGF$_1$ $\beta$ type oxa-phenylene compounds are also carried out by catalytic hydrogenation. For that purpose, palladium catalysts, especially on a carbon carrier, are preferred. It is also preferred that the hydrogenation be carried out in the presence of an inert liquid diluent, for example, methanol, ethanol, dioxane, ethyl acetate, and the like. Hydrogenation pressures ranging from about atmospheric to about 50 p.s.i., and hydrogenation temperatures ranging from about 10° to about 100° C. are preferred. The resulting dihydro product is isolated from the hydrogenation reaction mixture by conventional methods, for example, removal of the catalyst by filtration or centrifugation, followed by evaporation of the solvent.

Diimide reductions and catalytic hydrogenations to produce the various novel formula XIX, XXIII, XXVII, and XXXI 13,14-dihydro compounds of this invention from the corresponding PGE, PGF, PGA and PGB type oxa-phenylene compounds of the PG$_1$, PG$_2$, trans-5,6-dehydro-PG$_1$, and 5,6-dehydro-PG$_2$ series are shown in Chart B. G, J', Q, $R_1$, $R_9$, $R_{26}$, and ~ are as defined above, and L' is

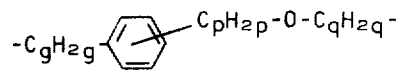

wherein $C_gH_{2g}$, $C_pH_{2p}$, and $C_qH_{2q}$ are as defined above.

The oxa-phenylene compounds of the PGE$_2$, PGF$_2$, PGA$_2$, and PGB$_2$ type wherein the carbon-carbon double bond in the carboxy-terminated side chain is in cis configuration are prepared by reduction of the corresponding acetylenic oxa-phenylene compounds, i.e., those with a carbon-carbon triple bond in place of said carbon-carbon double bond. For that purpose, there are used any of the known reducing agents which reduce an acetylenic linkage to a cis-ethylenic linkage. Especially preferred for that purpose are diimide, or hydrogen and a catalyst, for example, palladium (5%) on barium sulfate, especially in the presence of pyridine. See Fieser et al., "Reagents for Organic Synthesis," pp. 566–567, John Wiley and Sons, Inc., New York, N.Y. (1967).

CHART B

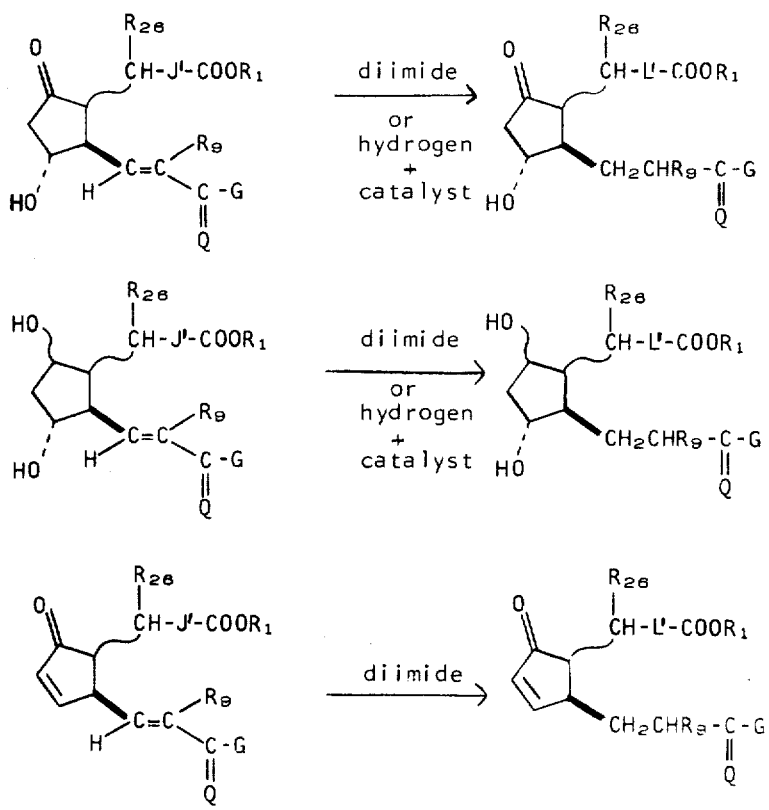

CHART B — Continued

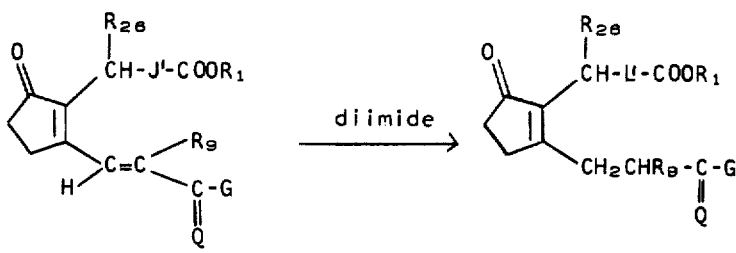

These reductions are shown in Chart C, wherein G, Q, $R_1$, $R_9$, $R_{26}$, and ~ are as defined above, and M' is

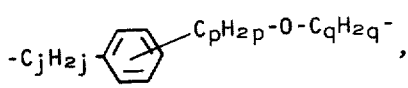

wherein $C_jH_{2j}$, $C_pH_{2p}$, and $C_qH_{2q}$ are defined above. These oxa-phenylene cis compounds of the $PGE_2$, $PGF_{2\alpha}$, $PGF_{2\beta}$, $PGA_2$, and $PGB_2$ type are also prepared as described hereinafter.

The oxa-phenylene PGE-type compounds of formulas XVI–XIX except wherein $R_1$ is hydrogen, and the oxa-phenylene PGA-type compounds of formulas XXIV–XXVII except wherein $R_1$ is hydrogen, are prepared by the series of reactions shown in Chart D, wherein G, J', $R_2$, $R_9$, and $R_{26}$ are as defined above; G' is the same as G except that T is replaced by T', wherein T' is the same as T above except that $R_9$ is not hydrogen; $R_{10}$ is the same as the above definition of $R_1$ except that $R_{10}$ does not include hydrogen; $R_{11}$ and $R_{12}$ are alkyl of one to 4 carbon atoms, inclusive; $R_{13}$ is alkyl of one to 5 carbon atoms, inclusive; and ~ indicates attachment of $-CHR_{26}-J'-COOR_{10}$ to the cyclopentane ring in alpha or beta configuration, and attachment of the moiety to the cyclopropane ring in exo or endo configuration.

The oxa-phenylene $PGE_1$-type compounds of formula XVI, the oxa-phenylene 5,6-dehydro-$PGE_2$ type compounds of formula XVIII, the oxa-phenylene $PGA_1$-type compounds of the formula XXIV and the oxa-phenylene 5,6-dehydro-$PGA_2$ type compounds of formula XXVI are also prepared by the series of reactions shown in Chart E, wherein G, G', $R_2$, $R_9$, $R_{10}$, $R_{13}$, and $R_{26}$ are as defined above; Z' is L' or $-C \equiv C-M'-$ wherein L' and M' are as defined above; and ~ indicates attachment of $-CHR_{26}-Z'-COOR_{10}$ to the cyclopentane ring in alpha or beta configuration, and attachment of the moiety to the cyclopropane ring in exo or endo configuration.

CHART C

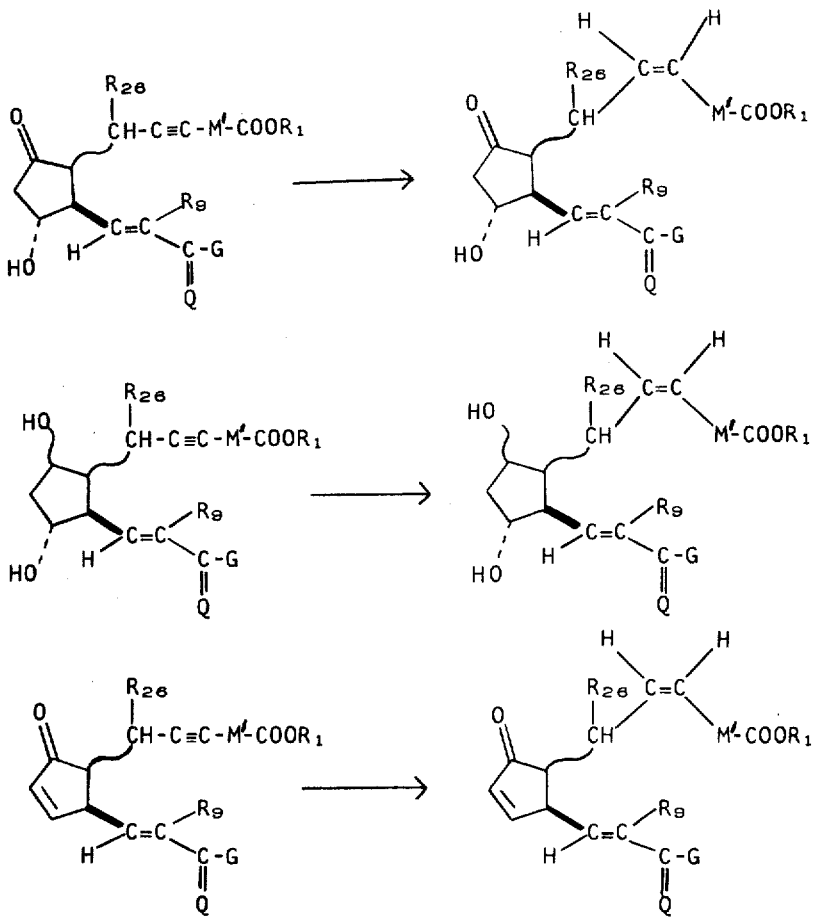

CHART C—Continued
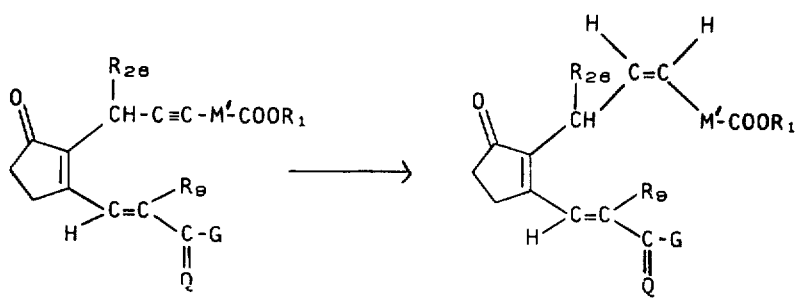
CHART D
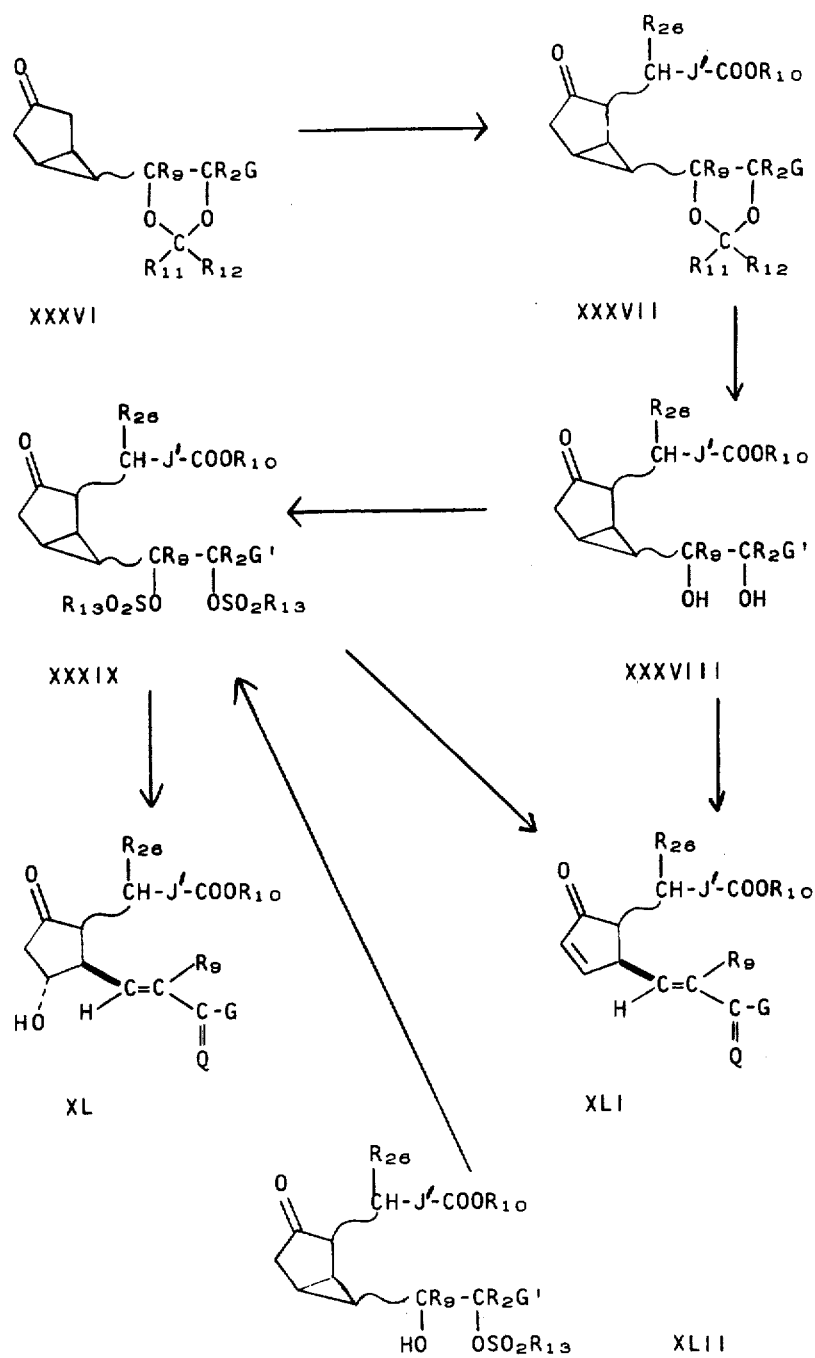

CHART E

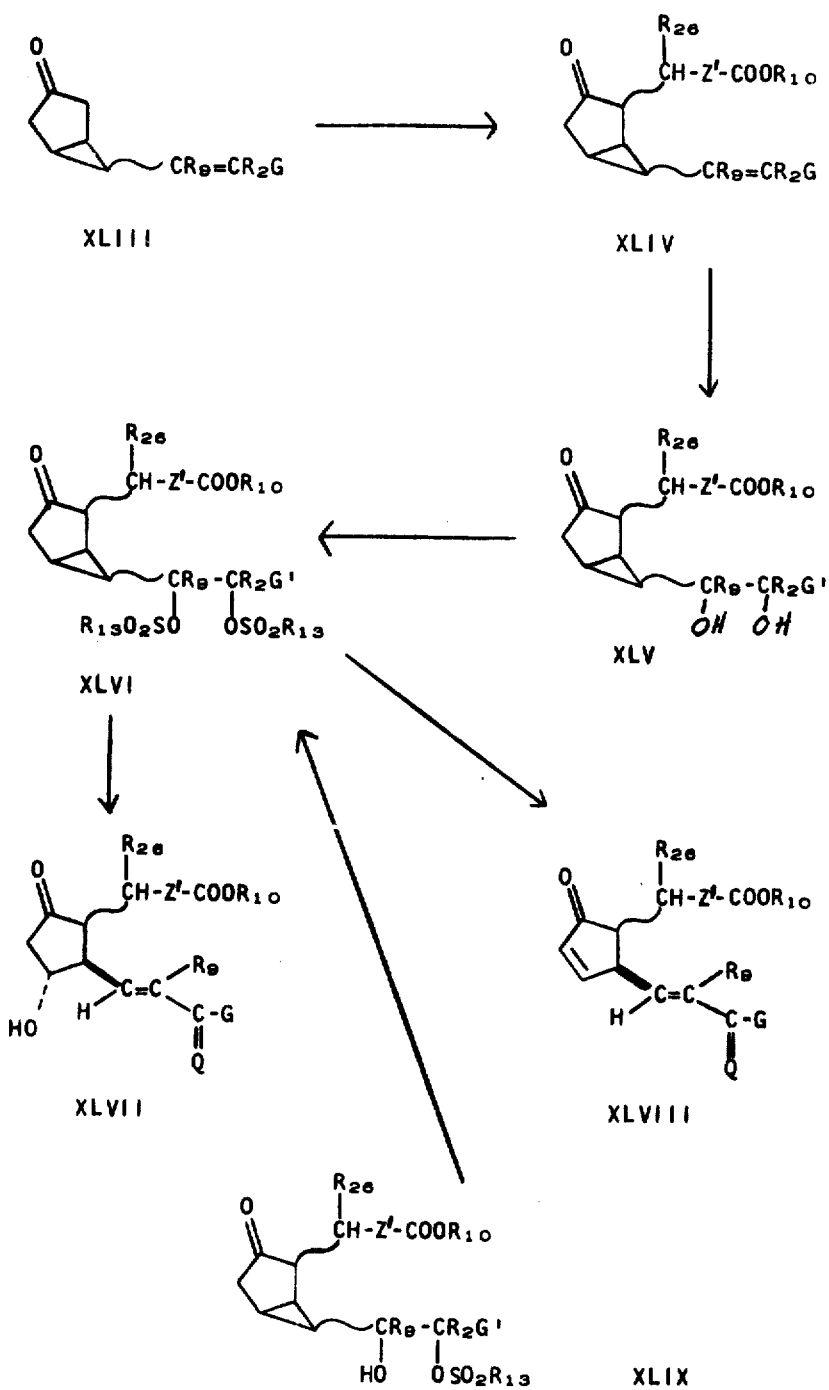

It should be observed regarding the series of reactions shown in Charts D and E, that the reactions starting with glycol XXXVIII in Chart D are similar to the reactions starting with glycol XLV in Chart E. The only differences here are the definitions of the divalent moieties J' (Chart D) and Z' (Chart E). J' includes saturated, cis and trans ethylenic, and acetylenic divalent moieties. Z' is limited to the saturated and acetylenic divalent moieties encompassed by J'. In other words, final oxa-phenylene PGE-type compounds of formula XL (Chart D) encompass compounds of formulas XVI to XVIII. Final oxa-phenylene PGA-type compounds of formula XLI (Chart D) encompass compounds of formulas XXIV to XXVI. On the other hand, final oxa-phenylene PGE-type compounds of formula XLVII (Chart E) encompass only compounds of formulas XVI and XVIII, and final oxa-phenylene PGA-type compounds of formula XLVIII (Chart E) encompass only compounds of formula XXIV and XXVI.

As will subsequently appear, an acetylenic intermediate of formulas XXXVII, XXXVIII, or XLV is transformed by step-wise reduction to the corresponding cis or trans ethylenic intermediates of formulas XXXVII or XXXVIII; and an acetylenic intermediate of formulas XXXVII, XXXVIII, or XLV or a cis or trans ethylenic intermediate of formulas XXXVII or XXXVIII is transformed by reduction to the corresponding saturated intermediate of formulas XXVII, XXXVIII, or XLV.

The initial bicyclo-ketone reactant of formula XLIII in Chart E is also used as an initial reactant to produce the initial bicyclo-ketone cyclic ketal reactant of formula XXXVI in Chart D. The following reactions will produce cyclic ketal XXXVI, wherein THP is tetrahydropyranyl, and $\phi$ is phenyl:

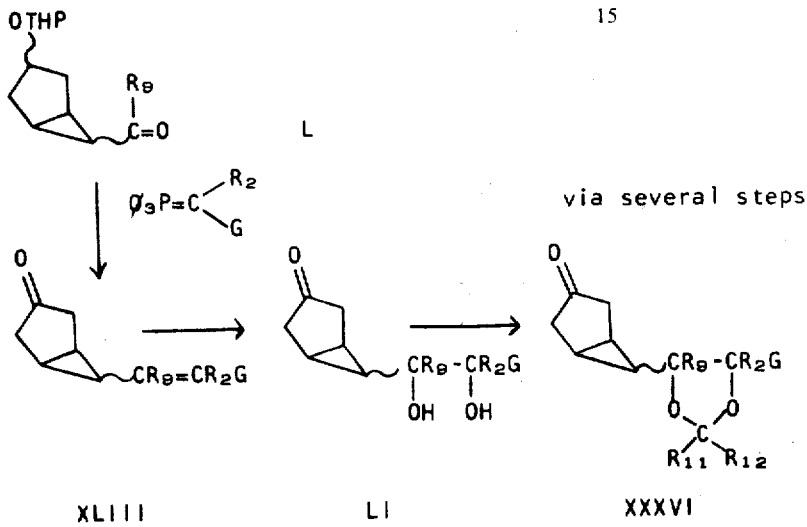

The bicyclo-ketone reactant of formula XLIII exists in four isomeric forms, exo and endo with respect to the attachment of the $-CR_9=CR_2G$ moiety, and cis and trans with respect to the double bond in that same moiety. Each of those isomers separately or various mixtures thereof are used as reactants according to this invention to produce substantially the same final oxaphenylene PGE or PGA type product mixture.

The process for preparing either the exo or endo configuration of the formula-XLIII bicyclo-ketone is known to the art. See. U.S. Pat. No. 3,776,940 and Belgian Pat. No. 702,477, Derwent Farmdoc No. 30,905.

See West Germany Offenlegungsschrift No. 1,937,912; reprinted in Farmdoc Complete Specifications, Book No. 14, No. 6869 R, Week $R_5$, Mar. 18, 1970.

In said U.S. Pat. No. 3,776,940 a reaction sequence capable of forming exo ketone XLIII is as follows: The hydroxy of 3-cyclopentenol is protected, for example, with a tetrahydropyranyl group. Then a diazoacetic acid ester is added to the double bond to give an exo-endo mixture of a bicyclo[3.1.0]hexane substituted at 3 with the protected hydroxy and at 6 with an esterified carboxyl. The exo-endo mixture is treated with a base to isomerize the endo isomer in the mixture to more of the exo isomer. Next, the carboxylate ester group at 6 is transformed to an aldehyde group or ketone group,

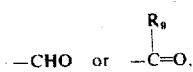

wherein $R_9$ is as defined above. Then, said aldehyde group or said keto group is transformed by the Wittig reaction, in this case to a moiety of the formula $-CR_9=CR_2$ G which is in exo configuration relative to the bicyclo ring structure. Next, the protective group is removed to regenerate the 3-hydroxy which is then oxidized, for example, by the Jones reagent, i.e., chromic acid (see J. Chem. Soc. 39 (1946)), to give said exo ketone XLIII.

Separation of the cis-exo and trans-exo isomers of XLIII is described in said U.S. Pat. No. 3,776,940. However, as mentioned above, that separation is usually not necessary since the cis-trans mixture is useful as a reactant in the next process step.

The process described in said U.S. Pat. No. 3,776,940 for producing the exo form of bicyclo-ketone XLIII uses, as an intermediate, the exo form of a bicyclo [3.1.0]-hexane substituted at 3 with a protected hydroxy, e.g., tetrahydropyranyloxy, and at 6 with an esterified carboxyl. When the corresponding endo compound is substituted for that exo intermediate, the process in said Offenlegungsschrift No. 1,937,912 leads to the endo form of bicyclo-ketone XLIII. That endo compound to be used has the formula:

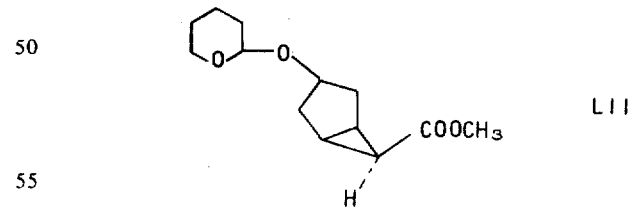

Compound LII is prepared by reacting endo-bicyclo[3.1.0]-hex-2-ene-6-carboxylic acid methyl ester with diborane in a mixture of tetrahydrofuran and diethyl ether, a reaction generally known in the art, to give endo-bicyclo[3.1.0]-hexane-3-ol-6-carboxylic acid methyl ester which is then reacted with dihydropyran in the presence of a catalytic amount of $POCl_3$ to give the desired compound. This is then used as described in said German Offenlegungsschrift No. 1,937,912 to produce the endo form of bicyclo-ketone XLIII.

As for exo XLIII, the above process produces a mixture of endo-cis and endo-trans compounds. These are separated as described for the separation of exo-cis and exo-trans XLIII, but this separation is usually not necessary since, as mentioned above, the cis-trans mixture is useful as a reactant in the next process step.

In the processes of said U.S. patent and said Offenlegungsschrift, certain organic halides, e.g., chlorides and bromides, are necessary to prepare the Wittig reagents used to generate the generic moiety, $-CR_9=CR_2G$ of bicyclo-ketone XLIII. These organic chlorides and bromides

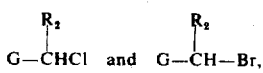

are known in the art or can be prepared by methods known in the art.

To illustrate the availability of these organic chlorides consider first the above-described oxa-phenylene PGE-type compounds of formulas XVI to XIX wherein $R_2$ is hydrogen and G is either (1) alkyl of one to 10 carbon atoms, inclusive, substituted with zero, one, 2, or 3 fluoro or (2)

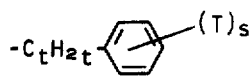

wherein $C_tH_{2t}$ represents a valence bond or alkylene of one to 10 carbon atoms, inclusive, substituted with zero, one, or 2 fluoro, with one to 7 carbon atoms, inclusive, between

and the ring; wherein T is alkyl of one to 4 carbon atoms, inclusive, fluoro, chloro, trifluoromethyl, or $-OR_6$, wherein $R_6$ is hydrogen or alkyl of one to 4 carbon atoms, inclusive, and s is zero, one, 2, or 3, with the proviso that not more than two T's are other than alkyl.

For those products wherein G is alkyl of two to 10 carbon atoms, substituted with 0-3 fluoro atoms, there are available the monohalo hydrocarbons, e.g., bromo- (or chloro-) -ethane, -propane, -pentane, -octane, and -decane; and the monohalofluorohydrocarbons, e.g., $CH_2FCH_2Br$, $CHF_2CH_2Cl$, $CF_3CH_2Br$, $F(CH_2)_3Br$, $CH_3CF_2CH_2Cl$, $CF_3(CH_2)_2Br$, $F(CH_2)_4Cl$, $CH_3CF_2CH_2CH_2Cl$, $C_4H_9CFHCH_2Br$, $CF_3(CH_2)_3Cl$, $CF_3(CH_2)_2BrCH_3$, $CH_2F(CH_2)_4Cl$, $C_2H_5CF_2(CH_2)_2Cl$, $CF_3(CH_2)_4Cl$, $CH_3(CH_2)_4CF_2(CH_2)_2CH_2Cl$, and $CH_3(CH_2)_3CF_2(CH_2)_3CH_2Cl$, as described in "Aliphatic Fluorine Compounds," A. M. Lovelace et al., Am. Chem. Soc. Monograph Series, 1958, Reinhold Publ. Corp. Those halides not available are prepared by methods known in the art by reacting the corresponding primery alcohol $G-CH_2OH$ with $PCl_3$, $PBr_3$, or any of the other halogenating agents useful for this purpose. Available alcohols include $CH_2CH(CF_3)CH_2OH$, $(CH_3)_2CHCH_2CH_2OH$, $(CH_3)_3CCH_2OH$, $CF_3CH(CH_3)CH_2CH_2OH$, for example. For those halides of the formula $G-CH_2-Hal$ wherein Hal is chloro or bromo, G is $R_{27}-(CH_2)_h-$, h being one, 2, 3, or 4, and $R_{27}$ being isobutyl, tert-butyl, 3,3-difluorobutyl, 4,4-difluorobutyl, or 4,4,4-trifluorobutyl, the intermediate alcohols are prepared as follows.

In the case of $R_{27}$ being isobutyl or tert-butyl, known alcohols are converted to bromides, thence to nitriles with sodium cyanide, thence to the corresponding carboxylic acids by hydrolysis, and thence to the corresponding primary alcohols by reduction, e.g., with lithium aluminum hydride, thus extending the carbon chain one carbon atom at a time until all primary alcohols are prepared.

In the case of $R_{27}$ being 3,3-difluorobutyl, the necessary alcohols are prepared from keto carboxylic acids of the formula, $CH_3-CO-(CH_2)_r-COOH$, wherein r is 2, 3, 4, 5, or 6. All of those acids are known. The methyl esters are prepared and reacted with sulfur tetrafluoride to produce the corresponding $CH_3-CF_2-(CH_2)_r-COOCH_3$ compounds, which are then reduced with lithium aluminum hydride to $CH_3-CF_2-(CH_2)_r-CH_2OH$. These alcohols are then transformed to the bromide or chloride by reaction with $PBr_3$ or $PCl_3$.

In the case of $R_{27}$ being 4,4-difluorobutyl, the initial reactants are the known dicarboxylic acids, $HOOC-(CH_2)_f-COOH$, wherein f is 3, 4, 5, 6, or 7. These dicarboxylic acids are esterified to $CH_3OOC-(CH_2)_f-COOCH_3$ and then half-saponified, for example with barium hydroxide, to give $HOOC-(CH_2)_f-COOCH_3$. The free carboxyl group is transformed first to the acid chloride with thionyl chloride and then to an aldehyde by the Rosenmund reduction. Reaction of the aldehyde with sulfur tetrafluoride then gives $CHF_2-(CH_2)_f-COOCH_3$ which by successive treatment with lithium aluminum hydride and $PBr_3$ or $PCl_3$ gives the necessary bromides or chlorides, $CHF_2-(CH_2)_f-CH_2Br$ or $CHF_2-(CH_2)_f-CH_2Cl$.

In the case of $R_{27}$ being 4,4,4-trifluorobutyl, aldehydes of the formula $CH_3OOC-(CH_2)_f-CHO$ are prepared as described above. Reduction of the aldehyde with sodium borohydride gives the alcohol $CH_3OOC-(CH_2)_f-CH_2OH$. Reaction with $PBr_3$ or $PCl_3$ then gives $CH_3OOC-(CH_2)_f-CH_2-Hal$. Saponification of that ester gives the carboxylic acid which by reaction with sulfur tetrafluoride gives the necessary $CF_3-(CH_2)_f-CH_2-Br$ or $CF_3-(CH_2)_f-CH_2-Cl$.

For the above reactions of $SF_4$, see U.S. Pat. No. 3,211,723 and J. Org. Chem. 27, 3164 (1962).

For those products wherein $R_2$ is hydrogen and G is

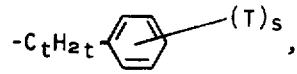

the halides necessary to prepare those compounds, if not readily available, are advantageously prepared by reacting the corresponding primary alcohol,

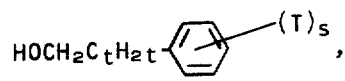

with $PCl_3$, $PBr_3$, HBr, or any of the other halogenating agents known in the art to be useful for this purpose. Some of the readily available halides are shown in Table I wherein s, T, and t of the formula for the intermediate halides are as defined above, and Hal is chloro, bromo, or iodo. Thus, compound No. 1 of Table I is represented by the formula wherein s and t are zero, and Hal is chloro, i.e.

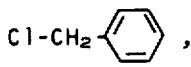

namely α-chlorotoluene or benzyl chloride; compound No. 8 of Table I is represented by the formula wherein s is zero, t is 2, and Hal is bromo, i.e.

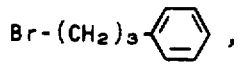

namely 1-bromo-3-phenylpropane or 3-bromopropylbenzene; and compound No. 63 of Table I represented by the formula wherein s is 3, T is methyl in the 2-, 4- and 5-positions with respect to the $C_tH_{2t}$ substitution, t is 2, and Hal is bromo, i.e.,

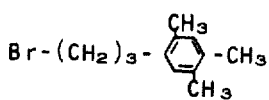

namely 1-(3-bromopropyl)-2,4,5-trimethylbenzene.

TABLE I

Intermediate Halides represented by the formula

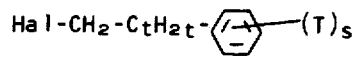

| No. | s | T | t | Hal |
|---|---|---|---|---|
| 1 | 0 | — | 0 | Cl |
| 2 | 0 | — | 0 | Br |
| 3 | 0 | — | 0 | I |
| 4 | 0 | — | 1 | Cl |
| 5 | 0 | — | 1 | Br |
| 6 | 0 | — | 1 | I |
| 7 | 0 | — | 2 | Cl |
| 8 | 0 | — | 2 | Br |
| 9 | 0 | — | 2 | I |
| 10 | 0 | — | 3 | Cl |
| 11 | 0 | — | 3* | Cl |
| 12 | 0 | — | 3 | Br |
| 13 | 0 | — | 4 | Cl |
| 14 | 1 | 2—CH₃ | 0 | Cl |
| 15 | 1 | 2—C₂H₅ | 0 | Cl |
| 16 | 1 | 4—C₂H₅ | 0 | Cl |
| 17 | 1 | 2—CF₃ | 0 | Cl |
| 18 | 1 | 4—OCH₃ | 0 | Cl |
| 19 | 1 | 3—CH₃ | 0 | Br |
| 20 | 1 | 4—CH₃ | 0 | Br |
| 21 | 1 | 4—C₅H₁₁ | 0 | Br |
| 22 | 1 | 4—Cl | 0 | Br |
| 23 | 1 | 2—CF₃ | 0 | Br |
| 24 | 1 | 3—CF₃ | 0 | Br |
| 25 | 1 | 4—CH₃ | 0 | I |
| 26 | 1 | 4—F | 1 | Cl |
| 27 | 1 | 3—Cl | 1 | Br |
| 28 | 1 | 4—Cl | 1 | Br |
| 29 | 1 | 4—F | 1 | Br |
| 30 | 1 | 2—Cl | 2 | Br |
| 31 | 1 | 3—Cl | 2 | Br |
| 32 | 1 | 4—Cl | 2 | Br |
| 33 | 1 | 4—F | 3* | Br |
| 34 | 1 | 2—Cl | 4 | Br |
| 35 | 1 | {2—CH₃, 4—CH₃} | 0 | Cl |
| 36 | 2 | {2—CH₃, 5—CH₃} | 0 | Cl |
| 37 | 2 | {2—CH₃, 6—CH₃} | 0 | Cl |
| 38 | 2 | {3—CH₃, 4—CH₃} | 0 | Cl |
| 39 | 2 | {2—CH₃, 4—Cl} | 0 | Cl |
| 40 | 2 | {2—CH₃, 5—CH₃} | 0 | Br |
| 41 | 2 | {2—CH₃, 6—CH₃} | 0 | Br |
| 42 | 2 | {3—CH₃, 5—t—butyl} | 0 | Br |

TABLE I-continued

Intermediate Halides represented by the formula

| No. | s | T | t | Hal |
|---|---|---|---|---|
| 43 | 2 | {3—CH₃, 4—Cl} | 0 | Br |
| 44 | 2 | {2—CH₃, 3—Br} | 0 | Br |
| 45 | 2 | {3—OCH₃, 4—OCH₃} | 0 | Cl |
| 46 | 2 | {3—OCH₃, 5—OCH₃} | 0 | Cl |
| 47 | 2 | {3—OCH₃, 5—OCH₃} | 0 | Br |
| 48 | 2 | {2—CH₃, 4—CH₃} | 1 | Cl |
| 49 | 2 | {2—CH₃, 4—CH₃} | 1 | Br |
| 50 | 2 | {3—CH₃, 4—CH₃} | 1 | Br |
| 51 | 2 | {3—OCH₃, 4—OCH₃} | 1 | Br |
| 52 | 2 | {3—OCH₃, 5—OCH₃} | 1 | Br |
| 53 | 2 | {3—OCH₃, 4—OCH₃} | 1 | I |
| 54 | 2 | {3—OCH₃, 4—OCH₃} | 2 | Br |
| 55 | 2 | {3—OCH₃, 5—OCH₃} | 2 | Br |
| 56 | 2 | {3—OCH₃, 5—OCH₃} | 4 | Br |
| 57 | 3 | {2—CH₃, 4—CH₃, 5—CH₃} | 0 | Cl |
| 58 | 3 | {2—CH₃, 4—CH₃, 6—CH₃} | 0 | Cl |
| 59 | 3 | {4—CH₃, 2—OCH₃, 5—OCH₃} | 0 | Cl |
| 60 | 3 | {2—CH₃, 3—CH₃, 6—CH₃} | 0 | Br |
| 61 | 3 | {2—CH₃, 4—CH₃, 6—CH₃} | 0 | Br |
| 62 | 3 | {2—CH₃, 3—OCH₃, 6—OCH₃} | 0 | Br |
| 63 | 3 | {2—CH₃, 4—CH₃, 5—CH₃} | 2 | Br |

\*-branched $\begin{matrix} -CH- \\ | \\ Et \end{matrix}$

Next, considering the intermediate halides for producing oxa-phenylene PGE-type compounds of formulas XIII to XVI wherein $R_2$ is alkyl of one to 4 carbon atoms, inclusive (A), and G is either of the two types (1) or (2) above, these organic chlorides and bromides, $$G-\overset{\underset{|}{R_1}}{C}H-Hal,$$

are known to the art or can be prepared by methods known in the art.

For type A-(1) above, i.e. wherein $R_2$ is alkyl and G is alkyl of one to 10 carbon atoms and 0-3 fluoro atoms, there are available such monohalofluorohydrocarbons as $CHF_2CHClCH_3$, $CF_3CHBrCH_3$, $CF_3CH_2CHBrCH_3$, $CH_3CF_2CHClCH_3$, $CF_3CHClC_2H_5$, and $C_2H_5CF_2CHClCH_3$, for example. Those not readily available are prepared from the corresponding secondary alcohol $$G-\overset{\underset{|}{R_2}}{C}HOH,$$

wherein $R_2$ is as defined above, with $PCl_3$, $PBr_3$, or any of the other halogenating agents known in the art to be useful for this purpose. Such alcohols include, for example, $CH_2FCH(OH)CH_2F$, $CF_3(CH_2)_2CH(OH)CH_3$, $CF_3CH(OH)(CH_2)CH_3$, $CF_3CH(OH)(CH_2)_3CH_3$, $CF_3CH(OH)C(CH_3)_3$, and $CF_3CH(OH)(CH_2)_5CH_3$. For those halides of the formula $G-CHR_2-Hal$, wherein G is $R_{27}-(CH_2)_h-$, using the definitions of Hal, $h$, $R_2$, and $R_{27}$ above, the intermediate alcohols are prepared as follows.

In the case of $R_{27}$ being isobutyl or tert-butyl, lower molecular weight primary alcohols are transformed to the corresponding longer-chain carboxylic acids and thence to the corresponding secondary alcohols by preparing the intermediate ketones,

by known procedures, for example $G-COCl + (R_2)_2Cd$, thereafter reducing the ketone to the secondary alcohol with sodium borohydride.

In the case of $R_{27}$ being 3,3-difluorobutyl, the procedure described above is applicable to converting $CH_3-CF_2-(CH_2)_2-COOCH_3$ described above to

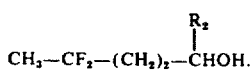

These alcohols are then transformed to the bromide or chloride by reaction with $PBr_3$ or $PCl_3$.

In the case of $R_{27}$ being 4,4-difluorobutyl, the corresponding secondary alcohols are prepared as described above, using intermediates prepared for the primary alcohols of this type above.

In the case of $R_{27}$ being 4,4,4-trifluorobutyl, corresponding secondary alcohols are prepared by transforming $CH_3OOC-(CH_2)_f-CHO$ to $CH_3OOC-(CH_2)_f-C(R_2)O$ by known methods and then proceeding with that ketone as described above for the corresponding aldehyde.

For type A-(2) halides, i.e. $R_2$ is alkyl and G is

some of the readily available halides are shown in Table II. Thus, compound No. 1 of Table II is represented by the formula wherein $s=0$, $R_2$=methyl, $t=0$, and Hal=Cl, i.e.

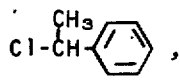

namely (1-chloroethyl)benzene; and compound No. 13 of Table II is represented by the formula wherein $s=2$, T=methyl, $R_2$=methyl, $t=1$, and Hal=Br, i.e.

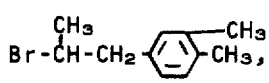

namely 4-(2-bromopropyl)-o-xylene or 1-(2-bromopropyl)3-methyl-4-methylbenzene.

TABLE II

Intermediate Halides represented by the Formula

| No. | s | T | $R_2$ | t | Hal |
|---|---|---|---|---|---|
| 1 | 0 | — | $CH_3$ | 0 | Cl |
| 2 | 0 | — | $C_2H_5$ | 0 | Cl |
| 3 | 0 | — | $C_2H_5$ | 0 | Br |
| 4 | 0 | — | $CH_3$ | 0 | I |
| 5 | 0 | — | $CH_3$ | 1 | Cl |
| 6 | 0 | — | n—$C_3H_7$ | 1 | Cl |
| 7 | 0 | — | $CH_3$ | 1 | Br |
| 8 | 0 | — | $C_2H_5$ | 2 | Cl |
| 9 | 1 | 4—$C_2H_5$ | $CH_3$ | 0 | Cl |
| 10 | 1 | 4—F | $CH_3$ | 0 | Cl |
| 11 | 1 | 4—Cl | $C_2H_5$ | 0 | Br |
| 12 | 1 | 4—F | $C_2H_5$ | 0 | Br |
| 13 | 2 | {3—$CH_3$, 4—$CH_3$} | $CH_3$ | 1 | Br |
| 14 | 2 | {3—$OCH_3$, 4—$OCH_3$} | $CH_3$ | 1 | Br |
| 15 | 2 | {2—$OCH_3$, 6—$OCH_3$} | $CH_3$ | 1 | Br |

Other intermediate halides of the general formula

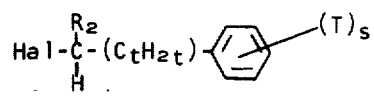

may be obtained from the secondary alcohols as discussed above. The secondary alcohols, wherein $R_2$ is alkyl, are prepared by transforming the —COOH of the corresponding carboxylic acid,

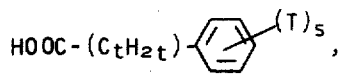

to a ketone by known procedures, e.g. by way of acyl chloride and a dialkylcadmium. Reduction of the ketone with sodium borohydride then yields the secondary alcohol,

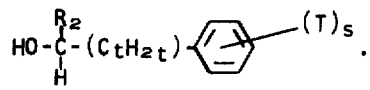

Hydroxyl groups on the aromatic ring are suitably protected during these reactions by first forming the corresponding tetrahydropyranyl ethers with dihydropyran; the hydroxyl groups are restored by mild acid hydrolysis as is well known in the art.

In the case of $C_tH_{2t}$ substituted with one or 2 fluoro atoms, there are a number of routes of the intermediate halides. The corresponding alcohols, for example $\beta$-fluorophenethyl alcohol, $\beta$-fluoro-$\alpha$-methyl-phenethyl alcohol, $\beta$-fluoro-$\alpha,\beta$-dimethyl-phenethyl alcohol and the like, are reacted with $PCl_3$, $PBr_3$or HBr to form the halide. Alternatively, the carboxylic acid having one less carbon atom in the chain than the desired intermediate halide, i.e.

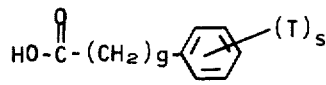

where $g = t-1$, is converted by a series of known methods to the 2,2-difluorohalide. Thus, the free carboxyl group is transformed first to the acid chloride with thionyl chloride and thence by way of the nitrile to the α-keto-acid. The carboxyl group is reduced to the alcohol with diborane and then converted to the α-keto halide. Finally, by reaction of the keto group with sulfur tetrafluoride, there is obtained

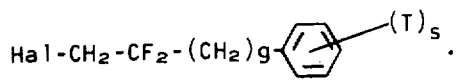

As mentioned above, formula XVI-to-XXXI compounds with an alpha-fluoro substituent in a straight chain 3-to-7-carbon G, i.e., G being —CHF—(CH$_2$)$_a$—CH$_3$ wherein $a$ is one, 2, 3, 4, or 5, represent embodiments among the novel oxa-phenylene compounds of this invention. Among those, for example, is 3-oxa-16-fluoro-3-7-inter-m-phenylene-4,5,6-trinor-PGE$_1$.

The formula-XLIII bicyclo-ketones necessary to produce those mono-fluoro compounds are advantageously prepared by reacting either of the above-mentioned bicyclo-aldehydes, exo or endo, with a Wittig reagent prepared from CH$_3$—CH$_2$) a—CO—CH$_2$—Br and triphenylphospine. The aldehyde group is thereby transformed to

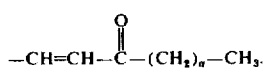

The resulting unsaturated ketone is reduced to the corresponding

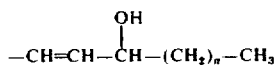

compound. Then —OH in that group is replaced with fluoro by known methods, for example, directly by reaction with 2-chloro-1,1,2-trifluorotriethylamine or indirectly, for example, by transforming the hydroxy to tosyloxy or mesyloxy, and reacting the resulting compound with anhydrous potassium fluoride in diethylene glycol. Similarly, the oxa-phenylene PG-type compounds wherein G is

having an alpha-fluoro substituent on the carbon adjacent to the hydroxy-substituted carbon (C-15 in PGE$_1$) represent preferred embodiments of this invention. In preparing the formula-XLIII bicyclo-ketone intermediates, there is used a Wittig reagent prepared from

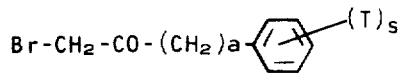

and triphenylphosphine. Following the steps above, the resulting unsaturated ketone containing the moiety

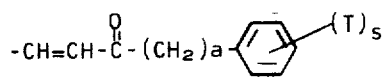

is reduced to the corresponding secondary alcohol. The —OH in that group is replaced by fluoro by known methods.

Another preference mentioned above is that the 1-position of G in the formula XVI-to-XXXI compounds be mono- or di-substituted with alkyl of one to 4 carbon atoms, particularly methyl or ethyl. In the steps of the synthesis shown in Charts D and E, G is then G'''—CR$_{21}$R$_{22}$— wherein R$_{21}$ and R$_{22}$ are methyl or ethyl and G''' is preferably alkyl of 2 to 6 carbon atoms or

wherein $k$ is zero, one, 2, or 3. Thus, in preparing the formula-XLIII intermediate olefin, a Wittig reagent is prepared from a halo compound of the general formula G'''—CR$_{21}$R$_{22}$—CR$_2$H—Hal wherein Hal is chloro or bromo. These compounds are known in the art or can be prepared by methods known in the art, including those methods described above.

For example, when G''' is CH$_3$(CH$_2$)$_3$—, R$_2$ and R$_{21}$ are hydrogen, and R$_{22}$ is methyl, there is employed 1-bromo(or -chloro)-2-methylhexane. If the halo compound is not available, the corresponding carboxylic acid is transformed to the alcohol and thence to the halide. Thus, 2,2-diethylvaleric acid yields 1-bromo-2,2-diethylpentane, wherein G''' is CH$_3$(CH$_2$)$_2$—, R$_2$ is hydrogen, and R$_{21}$ and R$_{22}$ are ethyl.

2-Ethylhexanoic acid yields 3-chloromethylheptane, wherein G''' is CH$_3$(CH$_2$)$_3$—, R$_2$ and R$_{21}$ are hydrogen, and R$_{22}$ is ethyl. 2-Ethyl-2-methylhexanoic acid yields 3-bromo-methyl-3-methylheptane, wherein G''' is CH$_3$(CH$_2$)$_3$—, R$_2$ is hydrogen, R$_{21}$ is methyl, and R$_{22}$ is ethyl. 2-Phenylpropionic acid yields 1-bromo-2-phenylpropane, wherein G''' is phenyl, R$_2$ and R$_{21}$ are hydrogen, and R$_{22}$ is methyl. 2-Methyl-2-phenylbutyric acid yields 1-bromo-2-methyl-2-phenylbutane, wherein G''' is phenyl, R$_2$ is hydrogen, R$_{21}$ is methyl, and R$_{22}$ is ethyl. 2-Methyl-4-(2,4,5-trimethoxyphenyl)butyric acid yields 1-chloro-2-methyl-4-(2,4,5-trimethoxyphenyl)butane, wherein G''' is (2,4,5-trimethoxyphenyl)ethyl, R$_2$ and R$_{21}$ are hydrogen, and R$_{22}$ is methyl.

Mono-alkyl substituted alkanoic acids useful for preparing the above halo intermediates are prepared by alkylation of an α-keto acid, G'''—CO—COOH, e.g.

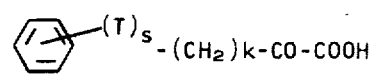

(prepared via the acid chloride and thence the nitrile) by means of a Grignard reagent, R$_{22}$MgHal for example.

The transformation of bicyclo-ketone-olefin XLIII to glycol LI is carried out by reacting olefin XLIII with a hydroxylation reagent. Hydroxylation reagents and procedures for this purpose are known in the art. See, for example, Gunstone, Advances in Organic Chemistry, Vol. 1, pp. 103–147, Interscience Publishers, New York, N.Y. (1960). Especially useful hydroxylation reagents for this purpose are osmium tetroxide and performic acid (formic acid plus hydrogen peroxide). Various isomeric glycols are obtained depending on such factors as whether olefin XLIII is cis or trans and endo or exo, and whether a cis or a trans hydroxylation reagent is used. These various glycol mixtures can be separated into individual isomers by silica gel chromatography. However, this separation is usually not necessary, since all isomers of particularly glycol are equally useful as intermediates according to this invention and the processes outlined in Chart D to produce final products of formulas XL and XLI, and then, according to Chart A, B, and C to produce the other final products of this invention.

The transformation of glycol LI to the cyclic ketal of formula XXXVI (Chart D) is carried out by reacting said glycol with a dialkyl ketone of the formula

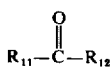

wherein $R_{11}$ and $R_{12}$ are alkyl of one to 4 carbon atoms, inclusive, in the presence of an acid catalyst, for example potassium bisulfate or 70% aqueous perchloric acid. A large excess of the ketone and the absence of water is desirable for this reaction. Examples of suitable dialkyl ketones are acetone, methyl ethyl ketone, diethyl ketone, methyl propyl ketone, and the like. Acetone is preferred as a reactant in this process.

Referring again to Chart D, cyclic ketal XXXVI is transformed to cyclic ketal XXXVII by alkylating with an alkylation agent of the formula

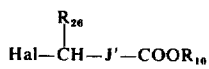

wherein $R_{10}$, $R_{26}$, and J' are as defined above, and Hal is chlorine, bromine, or iodine. Similarly, referring to Chart E, olefin XLIII is transformed to olefin XLIV by alkylating with an alkylation agent of the formula

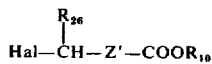

wherein $R_{10}$, $R_{26}$, Z', and Hal are as defined above.

Any of the alkylation procedures known in the art to be useful for alkylating cyclic ketones with alkyl halides and haloalkanoic esters are used for the transformations of XXXVI to XXXVII and of XLIII to XLIV. See, for example, the above-mentioned Belgian Pat. No. 702,477 for procedures useful here and used there to carry out similar alkylations, e.g., employing the bicyclo enamines.

For these alkylations, it is preferred that Hal be bromo of iodo. Any of the usual alkylation bases, e.g., alkali metal alkoxides, alkali metal amides, and alkali metal hydrides, are useful for this alkylation. Alkali metal alkoxides are preferred, especially tert-alkoxides. sodium and potassium are preferred alkali metals. Especially preferred is potassium tert-butoxide. Preferred diluents for this alkylation are tetrahydrofuran and 1,2-dimethoxyethane. Otherwise, procedures for producing and isolating the desired formula-XXXVII and -XLIV compounds are within the skill of the art.

These alkylation procedures produce mixtures of alpha and beta alkylation products, i.e. a mixture of formula XXXVII products wherein part has the $-CHR_{26}-J'-COOR_{10}$ moiety attached in alpha configuration, and wherein part has that moiety attached in beta configuration, or a mixture of the formula-XLIV products with the $-CHR_{26}-Z'-COOR_{10}$ moiety in both alpha and beta configurations. When about one equivalent of base per equivalent of formula-XXXVI or -XLIII ketone is used, the alpha configuration usually predominates. Use of an excess of base and longer reaction times usually result in production of larger amounts of beta products. These alpha-beta isomer mixtures are separated at this stage or at any subsequent stage in the multi-step processes shown in Charts D and E. Silica gel chromatography is preferred for this separation.

The necessary alkylating agents for the above-described alkylations, e.g. compounds of the formulas

are prepared by methods known in the art. There are four groups of compounds encompassed by these two genera of alkylating agents.

Alkylating agents of the formula

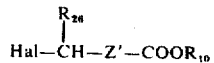

include compounds of the formulas:

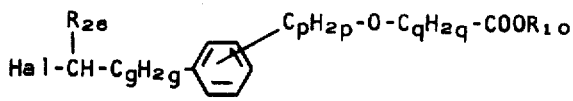

LIII

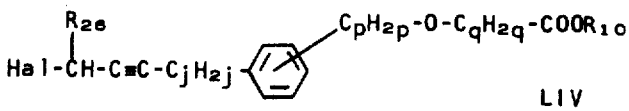

LIV

Alkylating agents of the formula

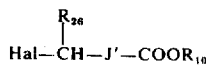

include the above-listed compounds of formuls LIII and LIV, and also compounds of the following formulas

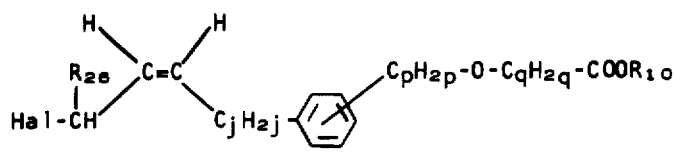

LV

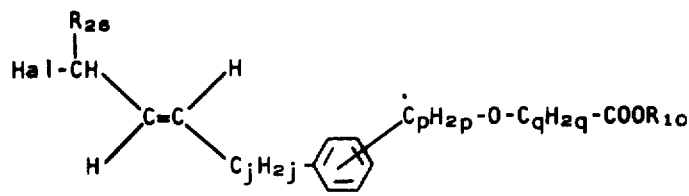

LVI

These alkylating agents of formulas LIII to LVI are accessible to those of ordinary skill in the art. In one route, the

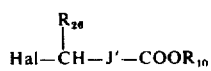

compounds are obtained from aldehyde or ketone reactants by a series of transformations as follows:

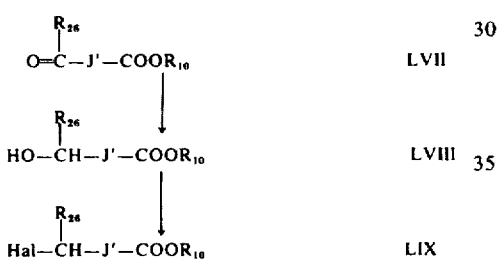

For example, methyl m-formylphenoxyacetate on reduction with sodium borohydride yields methyl m-(hydroxymethyl)-phenoxyacetate, which in turn is transformed to the formula-LIX compound, methyl m-(chloromethyl)phenoxyacetate, with thionyl chloride.

Those formula-LVII or formula-LVIII reactants which are not commercially available are advantageously prepared by adaptation of the Williamson ether syntheses, e.g. employing a hydroxy reactant and a halo-substituted acid or ester. Thus, the reaction

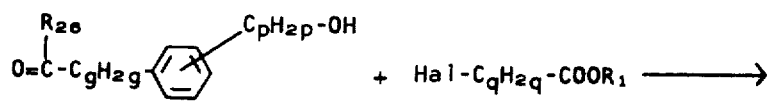

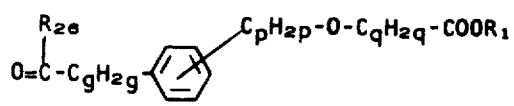

wherein Hal is chloro, bromo, or iodo, preferably iodo, proceeds in the presence of strong base, for example sodium hydride when $R_1$ is a carbon-containing group, and lithium diisopropyl amide when $R_1$ is hydrogen. within the definitions of $C_gH_{2g}$, $C_pH_{2p}$, and $C_qH_{2q}$, suitable reactants are readily available or are prepared by methods known to those skilled in the art.

Thus, when $R_{26}$ is hydrogen, and considering the variations of $C_gH_{2g}$ and $C_pH_{2p}$, the aldehyde reactants include (o, m, or p)-hydroxybenzaldehyde, (o, m, or p-hydroxyphenyl)acetaldehyde, (o or p)-hydroxyhydrocinnamaldehyde, 4-(o or p-hydroxyphenyl)-butyraldehyde, o-(2-hydroxyethyl)-benzaldehyde, and the like. Other aldehyde reactants are also accessible by methods known to those skilled in the art. For example, (o, m, or p-hydroxyethyl)benzaldehydes are obtained from (o, m, or p)-bromostyrene by the series of reactions:

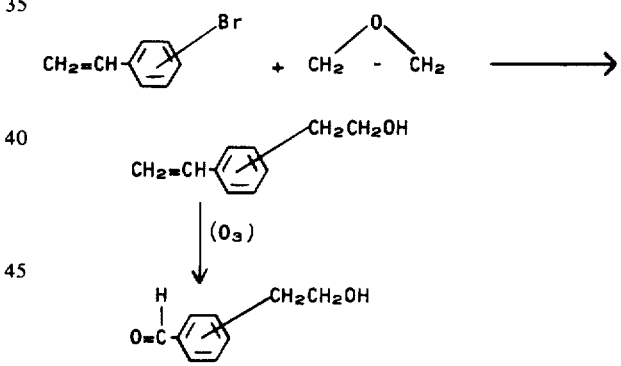

The reaction with ethylene oxide is carried out on a Grignard reagent prepared from the bromostyrene and magnesium. Substituted ethylene oxides are used to obtain substituted $C_pH_{2p}$ chains, e.g. propylene oxide, 1,2-epoxy-2-methylpropane, 1,2-epoxybutane, 1,2- epoxy-2,3-dimethylbutane, and the like. Instead of using ozone to form the aldehyde, hydroxylation and oxidation with osmium tetroxide and periodic acid are optional (see J. Org. Chem. 21, 478, 1956).

Compounds with $C_pH_{2o}$ chains are obtained by replacing

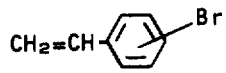

with

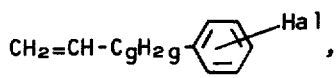

e.g. 1-allyl-4-bromobenzene 1-allyl-2-chlorobenzene. 4-(o, m, or p-chlorophenyl)-1-butene, and the like. Compounds with $C_pH_{2p}$ chains are obtained by replacing ethylene oxide with suitable alkylating agents, e.g. trimethylene oxide, 1,3-epoxybutane, 1,3-epoxy-3-methylbutane and the like, or suitable reactions steps.

Other variations of the above reactions and reactants will be apparent to those skilled in the art. Thus, an alkene-substituted phenol is condensed with a halo-substituted acid or ester and thereafter transformed as an aldehyde to the halo alkylating agent within the scope of formula LIX by the following steps:

Available for this series of reactions are (o, m, or p)-vinylphenol, p-allylphenol, 4-(o, m, or p-hydroxyphenyl)-1-butene, and the like.

Alternatively, a haloalkylphenol is condensed with a halo-substituted acid or ester by the reaction:

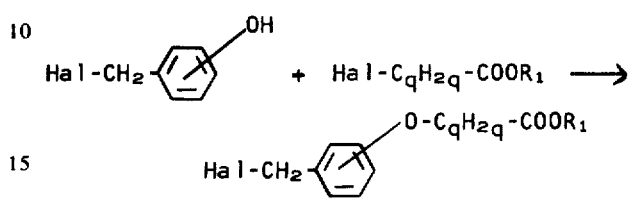

Available are p-(2-bromoethyl)phenol, p-(bromobutyl)-phenol, -bromo-butyl)-phenol, and the like.

Considering the halo-substituted acid or ester reactants in the above ether syntheses and the variations of $C_qH_{2q}$, there are a wide variety of reactants available, which will lead to the desired formula-LIX alkylating agent. For example:

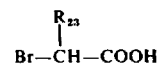

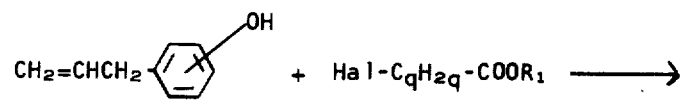

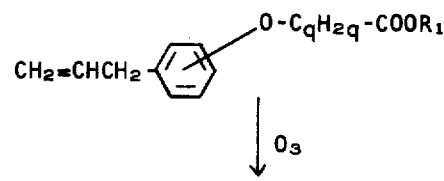

↓ $O_3$

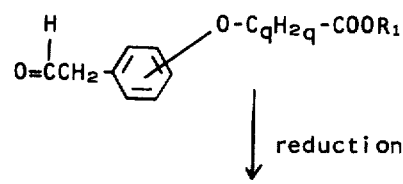

↓ reduction

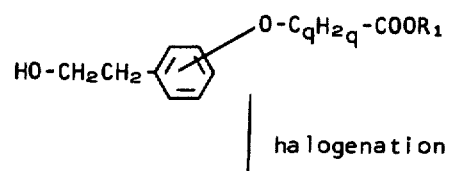

↓ halogenation

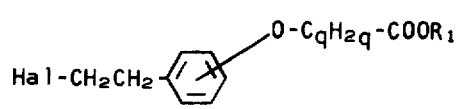

wherein $R_{23}$ is hydrogen or alkyl of one to 5 carbon atoms, inclusive; Br—$(CH_2)_2$—COOH, Br—$C(CH_3)_2$—COOH, Br—$C(C_2H_5)_2$—COOH, BrC$(CH_3)(C_2H_5)$—COOH, Br—CH$(CH_3)$—CH$_2$—COOH, Br—$(CH_2)_3$—COOCH$_3$, Cl—CH$(C_2H_5)$—CH$_2$—COOCH$_3$, Cl—CH$(n$—$C_3H_7)$—CH$_2$—COOCH$_3$, Br—CH$(CH_3)$—$(CH_2)_2$—COOC$_2H_5$, Br—CH$(CH_3)$—CH$_2$—CH$(CH_3)$—COOC$_2H_5$, Br—CH$(CH_3)$—CH$(CH_3)$—CH$_2$—COOC$_2H_5$, Br—C$(CH_3)_2$—CH$_2$—CH$(CH_3)$—COOC$_2H_5$, Cl—CH$(n$—$C_4H_9)$—CH$_2$—COOC$_2H_5$, Cl—C$(CH_3)_2$—CH$_2$—COOC$_2H_5$, Br—CH$(n$—$C_2H_7)$—$(CH_2)_2$—COOH, and Cl—CH$(C_2H_5)$—$(CH_2)_2$—COOH are available. The preferred iodo reactants are obtained by methods known to those skilled in the art.

When $C_qH_{2q}$ has two alkyl groups attached to the ω or ω-1 carbon atom of the halo-substituted acid or ester reactants, it is preferred that halo be replaced with mesyloxy or tosyloxy prior to the ether synthesis, and that relative mild bases and reaction conditions be used, for example, potassium tert-butoxide in dimethyl sulfoxide.

In another route to the formula-LIX alkylating agents, the Williamson ether synthesis employs hydroxy-esters or acids of the formula HO—$C_qH_{2q}$—COOR$_1$ for condensation with halo-substituted reactants as follows:

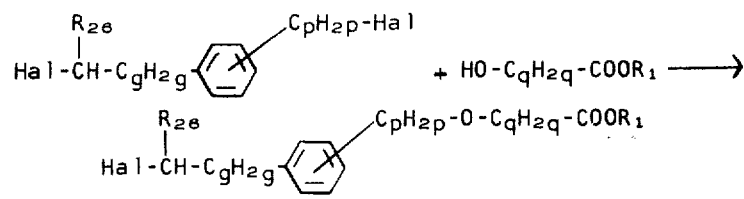

For example, α,α'-dibromo-o-xylene is contacted with ethyl glycolate in the presence of sodium hydride to yield ethyl O-(bromomethyl)-benzyloxyacetate.

Typical halo reactants which are useful for this reaction are α-bromo-(o, m, or p)-chlorotoluene, 1-bromo-(2 or 3)-(2-bromoethyl)benzene, 1-(3-bromopropyl)-(1 or 2)-chlorobenzene, and 1-(4-bromobutyl)-1-chlorobenzene.

When $C_pH_{2p}$ has two alkyl groups attached to the carbon atom to which Hal is attached, it is preferred that this Hal be replaced with mesyloxy or tosyloxy prior to the ether synthesis and that relatively mild bases and reaction conditions be used.

Considering the hydroxy acid or ester reactants, there are available a wide range of suitable compounds within the scope of HO—$C_qH_{2q}$—COOR$_1$ which will lead to the desired formula-LIX alkylating agent. For example: HOCH$(CH_3)$—COOCH$_3$, HOC$(CH_3)_2$—COOH, HOCH$(C_2H_5)$—COOH, HOC$(CH_3)(C_2H_5)$—COOH, HO$(CH_2)_2$—COOC$_2H_5$, HOCH$(CH_3)$—CH$_2$—COOH, HOCH$(n$—$C_3H_7)$—COOH, HOC$(n$—$C_3H_7)(CH_3)$—COOH, HOCH$(C_2H_5)$—CH$_2$—COOH, HOCH$(CH_3)$—$(CH_2)_2$—COOH, HOCH$(n$-C$_4H_9)$—COOH, HOC$(n$-C$_4H_9)(CH_3)$—COOH, HOCH$(n$-C$_3H_7)$—CH$_2$—COOCH$_3$, HOCH$(C_2H_5)$—$(CH_2)_2$—COOH, HOCH$(n$-C$_5H_{11})$—COOH, HOCH$(n$-C$_4H_9)$—CH$_2$—COOH, HOCH$(n$-C$_3H_7)$—$(CH_2)_2$—COOH are available.

When a formula-LIX alkylating agent is desired in which there are two alkyl substituents on both carbon atoms attached to the oxa —O—, it is preferred that, if the halo-acid route be used, the halo atom on the acid be chloro and that freshly precipitated wet magnesium hydroxide in an inert solvent suspension be used as the base; and if the hydroxy-acid route be used, the —$C_pH_{2p}$—Hal group is preferrably —$C_pH_{2p}$—Cl. If the hydroxy-acid route is used with —$C_pH_{2p}$—I, silver oxide is used as the base.

The alkylating agents of formulas LIII to LVI are esters. Any of the above acid forms are readily converted to esters. Variations in $R_{10}$ within the definition of $R_{10}$ herein are readily made by methods known in the art. The ester moiety is chosen according to the desired type of final oxa-phenylene PG-type product.

Formula-LVII aldehyde reactants which lead to the formula LIX alkylating agents are also obtained by reaction of halo-substituted aldehydes with hydroxy acids or ester reactants. Thus, there are employed o-(bromoethylbenzaldehyde, p-chlorohydratropaldehyde, and the like.

When $R_{26}$ is alkyl, the formula-LIX

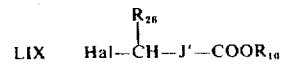

alkylating agents are prepared from the corresponding reactants wherein $R_{26}$ is methyl, ethyl, propyl, or butyl, or their isomers. For example m-bromo-α-methylstyrene reacts as follows:

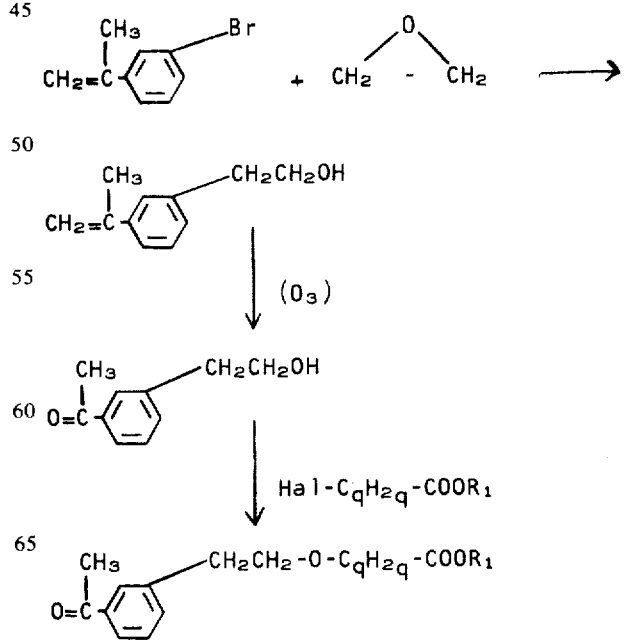

Typical halo-substituted ketones available for this purpose include (2', 3', or 4')-(bromo, chloro, or iodo)-acetophenone, (3' or 4')-bromopropiophenone, (3' or 4')-chlorobutyrophenone, and 4'-(bromo or chloro)-valerophenone. Other reactants leading to the $R_{26}$-(alkyl)-substituted formula-LIX alkylating agents are accessible to those skilled in the art.

Although the above methods are generally useful for preparing alkylating agents within the scope of formulas

above, there are preferred methods for preparing the formula-LIV compounds containing the $-C \equiv C-C_jH_{2j}-$ moiety.

Considering the compounds of the formula

there is employed as starting material (o, m, or p-)vinylanisole in the following series of transformations:

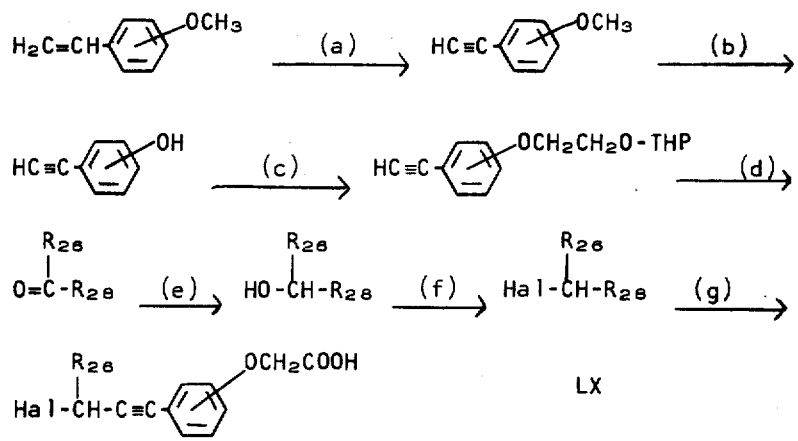

Herein, THP represents tetrahydropyranyl and $R_{28}$ represents

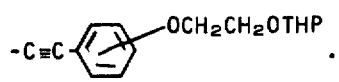

The reagents and conditions for bringing about these transformations are known to those skilled in the art. Thus, in step a, reacting first with bromine and then with sodium amide in liquid ammonia yields the acetylenic derivative (see J. Am. Chem. Soc. 56, 2064, 1934). Step b utilizes boron tribromide for example. Step c proceeds either with ethylene chlorohydrin and a strong base, e.g., NaOH or KOH, followed by dihydropyran in the presence of an acid catalyst, or with the tetrahydropyranyl ether of the chlorohydrin and a strong base. Step d utilizes $R_{26}COCl$ in the presence of a strong base, e.g., sodium amide, phenyllithium, or sodium triphenylmethane. Alternatively, if $R_{26}$ is desirably hydrogen, paraformaldehyde is employed (see J. Am. Chem. Soc. 92, 6314 (1970). The reaction in step e is done with a metal hydride, e.g., sodium borohydride. In step f thionyl chloride yields the formula-LX chloro compounds. Finally, in step g the THP moiety is selectively removed by mild hydrolysis in acid medium and the terminal $-CH_2OH$ moiety is oxidized to $-COOH$, e.g. with the Jones reagent. The alkylating agent is converted by known means to an ester, as defined by $R_{10}$, to yield the desired compounds.

Considering the compounds of the formula

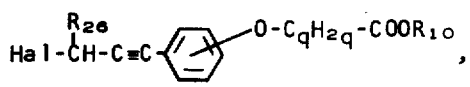

the above series of transformations are used, except that in step c $ClCH_2CH_2OH$ is replaced by $Cl-C_qH_{2q}-CH_2OH$. There are obtained in step f compounds of the formula

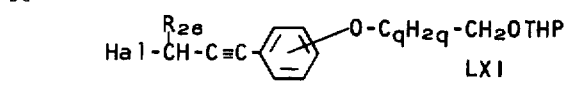

LXI wherein $C_qH_{2q}$, Hal, $R_{26}$ and THP are as defined above. Thereafter these formula-LXI compounds are transformed as in step g above to the desired compounds.

Considering the compounds of the formula

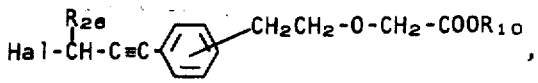

there are employed as starting materials the ar-halostyrenes. These are transformed by the following steps:

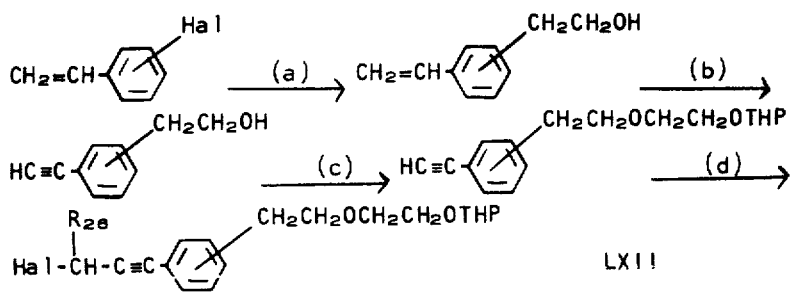

Thereafter, these formula-LXII compounds are transformed as in step g above to the desired compounds. In step a, the halo compounds are converted to a Grignard reagent with magnesium and thence reacted with ethylene oxide. In step b, the hydroxy group is converted to —OTHP with dihydropyran, the acetylenic moiety is formed as in step a leading to the formula-LX compounds above, and the THP moiety removed by mild acid hydrolysis. In step c, the chain is extended by reaction with Hal—CH$_2$CH$_2$OH, preferably the bromo or iodo derivatives, in the presence of strong base, e.g., phenyl lithium, sodium triphenylmethane, or sodium hydride. Thereafter, in step d the transformations follow the general scheme of steps d–f leading to the formula-LX compound to yield the formula-LXII compounds. Transformation as in step g above yields the desired compounds.

Considering the compounds of the formula

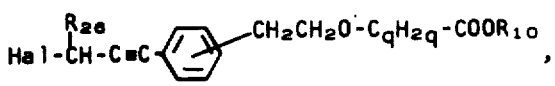

the series of transformations in the paragraph immediately preceeding are used, except that in step c Ha-1—CH$_2$CH$_2$OH is replaced by Hal—C$_q$H$_{2q}$—CH$_2$OH. There are obtained in step d compounds of the formula

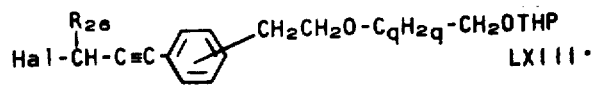

These formula-LXIII compounds are transformed as in step g above to the desired esters.

Considering the compounds of the formula

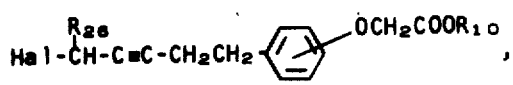

there are employed as starting materials anisolyl aliphatic acids, e.g., anisolylacetic acid, in the following steps:

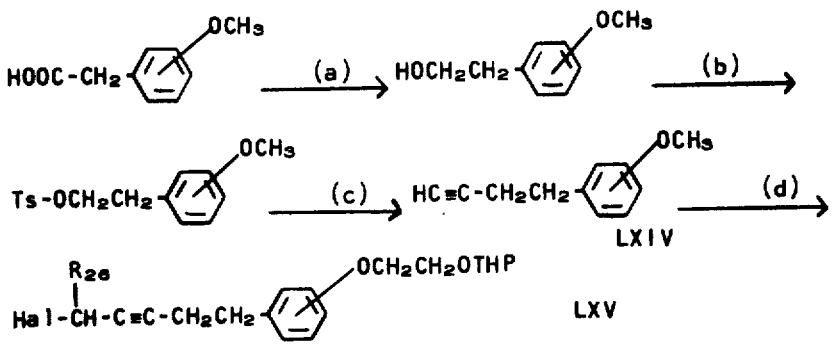

In step a, the carboxyl group is reduced with a metal hydride, e.g. lithium aluminum hydride. In step b, where Ts represents the toluenesulfonyl ("tosyl") moiety, the reaction is carried out with toluenesulfonyl chloride and pyridine. In step c, the acetylenic moiety is introduced with lithium acetylide (see J. Am. Chem. Soc. 80, 6626, 1958) to yield the formula-LXIV intermediates. Subsequent steps in d to form the formula-LXV compounds follow from steps b–f for the formula-LX compounds above. Finally, the formula-LXV compounds are transformed as in step g above to the desired esters.

Considering the compounds of the formula

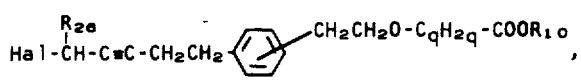

there are employed as starting materials benzenedialiphatic acids, e.g., benzenediacetic acid, in the following steps:

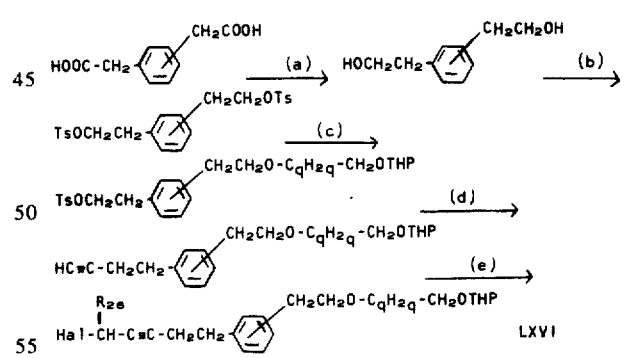

In step a, the carboxyl groups are reduced with a metal hydride, e.g. lithium aluminum hydride. In step b, reaction with toluenesulfonyl halide yields the bistosyl derivative. In step c c tosyloxy group is replaced by reaction with HO—$C_qH_{2q}$—$CH_2OTHP$ in the presence of sodium hydride in an inert solvent, e.g. dimethyl formamide. In step d, the acetylenic moiety is introduced as in forming the formula-LXIV compounds above. Subsequent steps in e to form the formula-LXVI compounds follow from steps b–f for the formula-LX compounds above. Finally, the formula-LXVI compounds are transformed as in step g above to the desired esters.

Variations in the above formula LX-to-LXVI compounds and their corresponding ester alkylating agents as to chain length or branching in the $C_gH_{2g}$, $C_jH_{2j}$, acetylenic compounds to cis-ethylenic compounds are bis(3-methyl-2-butyl)borane ("disiamylborane") and diisobutyl-aluminum hydride.

For trans reductions of the acetylenic bond, except for those compounds containing halogen, it is advantageous to use sodium or lithium in liquid ammonia or a liquid alkylamine, e.g., ethylamine. When the moiety HO—$CH_2$—C ≡ C— is present in the acetylenic compound being reduced, the use of lithium aluminum hydride gives trans reduction of the triple bond. Procedures for these trans reductions are known in the art. See, for example, Fieser et al., above cited, pp. 577, 592–594, and 603, and J. Am. Chem. Soc. 85, 622 (1963).

The alkylating agents of the formulas

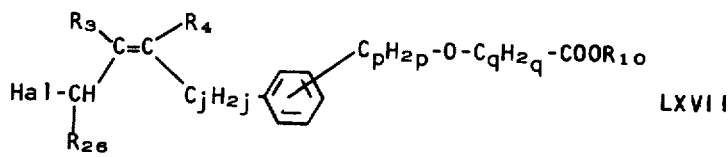

LXVII

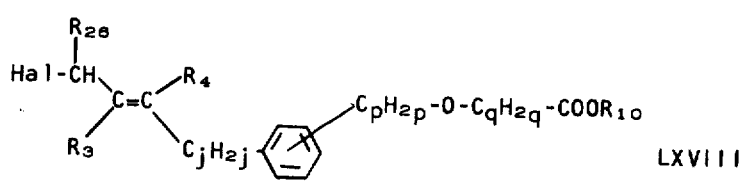

LXVIII $C_pH_{2p}$, and $C_qH_{2q}$ moieties and as to the identity of $R_1$ or $R_{26}$, within the scope of these terms as herein defined, are available to those skilled in the art making use of the principles disclosed herein.

Other modifications which are encompassed within this disclosure include the use of alkylating agents wherein Hal is replaced by hydrocarbonsulfonyl, e.g. tosyl or mesyl (methanesulfonyl) groups. Furthermore, the formula-LX, -LXI, -LXII, -LXIII, -LXV, and -LXVI compounds are alternatively employed as alkylating agents, instead of the corresponding esters, and the alkylated formula-XXXVI and -XLIII compounds subsequently converted to the desired formula-XXXVII and -XLIV compounds by mild hydrolysis to remove the THP moiety, oxidation to convert the —$CH_2OH$ moiety to —COOH, and, optionally, esterification to the desired $R_1$ identity.

The cis and trans ethylenic alkylating agents of formulas LV and LVI above are preferably prepared by cis or trans reduction of the corresponding formula-LIV acetylenic compounds prepared as above, or by cis or trans reduction of any earlier acetylenic intermediate in which both ends of the acetylenic bond are substituted, i.e., not hydrogen as in the moiety HC ≡ C—. Alternatively, this cis or trans reduction is carried out on any subsequent acetylenic reaction product leading up to and including the final acetylenic alkylating agent of formula LIV.

For these cis reductions of acetylenic bonds, it is advantageous to use hydrogen plus a catalyst which catalyzes hydrogenation of —C ≡ C— only to cis —CH=CH—. Such catalysts and procedures are well known to the art. See, for example, Fieser et al., "Reagents for Organic Syntheses", pp. 566–567; John Wiley and Sons, Inc., New York, N.Y. (1967). Palladium (5%) on barium sulfate, especially in the presence of pyridine as a diluent, is a suitable catalyst for this purpose. Alternative reagents useful to transform these are available by methods known to those skilled in the art.

Thus, the above-described intermediates within the scope of

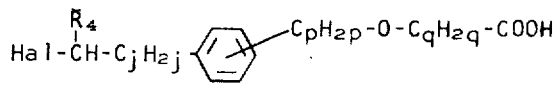

are transformed to the phosphoranes and condensed with halo-substituted ketones of the formula

wherein THP is tetrahydropyranyl, by the Wittig reaction (Organic Reactions, Vol. 14, p. 270, Wiley, 1965). Mixtures of the cis and trans isomers of formulas LXVII and LXVIII are usually obtained, which are separable by methods known in the art. Higher proportions of the cis isomers are obtained in the presence of Lewis bases; higher proportions of the trans isomers result by employing the phosphonate modification (D. H. Wadsworth et al., J. Org. Chem. 30, 680 (1965)). Thereafter, hydrogen on the terminal carboxyl group is replaced with $R_{10}$, THP is replaced with hydrogen, and the terminal hydroxyl group replaced with Hal, for example with $PBr_3$ or $PCl_3$.

Alternatively, an intermediate of the formula

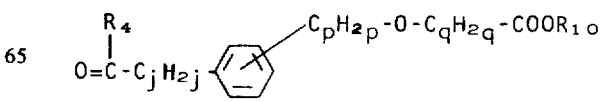

is condensed by the Wittig reaction with a phosphorane or phosphonate derived from

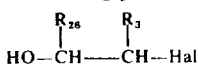

Subsequently, the terminal hydroxy group is replaced with Hal by suitable reagents, for example PBr₃ or PCl₃.

Concerning the alkylation of the cyclopentane ring, another useful alkylation procedure utilizes an intermediate enamine. That enamine is prepared by mixing either the formula-XXXVI ketal or the formula-XLIII olefin ketone with a secondary amine of the formula

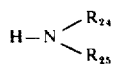

wherein $R_{24}$ and $R_{25}$ are alkyl or alkylene linked together through carbon or oxygen to form together with a nitrogen a 5 to 7-numbered heterocyclic ring. Examples of suitable amines are diethylamine, dipropylamine, dibutylamine, dihexylamine, dioctylamine, dicyclohexylamine, methylcyclohexylamine, pyrrolidine, 2-methylpyrrolidine, piperidine, 4-methylpiperidine, morpholine, hexamethylenimine, and the like.

The enamine is prepared by heating a mixture of the formula-XXXVI ketal or the formula-XLIII olefin ketone with an excess of the amine preferably in the presence of a strong acid catalyst such as an organic sulfonic acid, e.g., p-toluenesulfonic acid, or an inorganic acid, e.g., sulfuric acid. It is also advantageous to carry out this reaction in the presence of a water-immiscible diluent, e.g., benzene or toluene, and to remove water by azeotropic distillation as it is formed during the reaction. Then, after water formation ceases, the enamine is isolated by conventional methods.

The enamine is then reacted with a haloester,

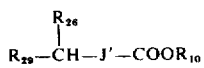

to give the desired formula-XXXVII or -XLIV product. This reaction of the enamine is carried out by the usual procedures. See "Advances in Organic Chemistry," Interscience Publishers, New York, N.Y., Vol. 4, pp. 25–47 (1963) and references cited therein. In addition to halogen, $R_{29}$ in

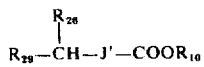

can also be tosylate, mesylate, and the like. It is especially preferred that $R_{29}$ be bromine or iodine. Dimethylsulfoxide is especially useful as a diluent in the reaction of the enamine with the haloester.

Referring again to Chart D, after alkylation as discussed above, cyclic ketal XXXVII is transformed to glycol XXXVIII by reacting the cyclic ketal with an acid with pK less than 5. Suitable acids and procedures for hydrolyzing cyclic ketals to glycols are known in the art. Suitable acids are formic acid, hydrochloric acid, and boric acid. Especially preferred as diluents for this reaction are tetrahydrofuran and β-methoxyethanol.

Referring again to Chart E, after alkylation as discussed above, olefin XLIV is hydroxylated to glycol XLV. As discussed above, the divalent moiety —Z'— includes the moieties

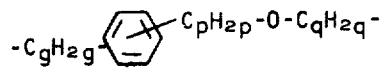

and

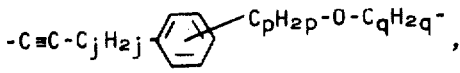

wherein $C_gH_{2g}$, $C_jH_{2j}$ and $C_qH_{2q}$ are as defined above. When Z' is

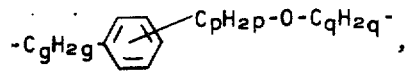

this hydroxylation of XLIV is carried out as described above for the hydroxylation of olefin XLIII to glycol LI, i.e., with any of the known reagents and procedures described in Gunstone, above cited. When Z' is

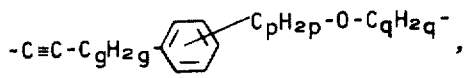

some of the reagents and procedures described by Gunstone tend to attack the acetylenic linkage as well as the ethylenic linkage of the formula-XLIV olefin. Therefore it is preferred to use a hydroxylation reagent and procedure which attacks the ethylenic linkage preferentially. For this, it is preferred to carry out hydroxylation of these acetylenic formula-XLIV olefins with organic peracids, e.g., performic acid, peracetic acid, perbenzoic acid, and m-chloro-perbenzoic acid, as described by Gunstone, above cited, pp. 124–130.

As discussed above regarding the hydroxylation of unalkylated olefin XLIII to unalkylated glycol LI, various isomeric glycols are obtained by hydroxylation of the formula-XLIV alkylated olefin. The particular formula-XLV glycol or glycol mixture obtained depends on such factors as whether the olefin XLIV is cis or trans and endo or exo, and whether a cis or a trans hydroxylation takes place. However, all of the isomeric formula-XLIV glycols and the various glycol mixtures are equally useful as intermediates according to this invention and the processes of Chart E to produce final products of formulas XLVII and XLVIII, and then according to Charts A, B, and C, to produce the other final products of this invention. Therefore, it is usually not necessary to separate individual formula-XLV glycol isomers before proceeding further in the synthesis, although that separation can be accomplished by silica gel chromatography.

It is preferred that glycols XXXVIII and XLV of Charts D and E, respectively, be free of phenolic hydroxyl substituents before the alkanesulfonation step. If any of the intermediate formula-XXXVIII or formula-XLV compounds have phenolic hydroxyls, these hydroxyls are readily converted to tetrahydropyranyloxy (OTHP) by reaction with dihydropyran, e.g. in the presence of a catalytic amount of POCl₃. The —OTHP group is subsequently replaced by OH under mildly acidic conditions.

Referring again to Charts D and E, bis(alkanesulfonic acid) esters XXXIX and XLVI are prepared by reacting glycols XXXVIII and XLV, respectively, with an alkanesulfonyl chloride or bromide, or with an alkanesulfonic acid anhydride, the alkyl in each containing one to 5 carbon atoms, inclusive. Alkanesulfonyl chlorides are preferred for this reaction. The reaction is carried out in the presence of a base to neutralize the byproduct acid. Especially suitable bases are tertiary amines, e.g., dimethylaniline or pyridine. It is usually sufficient merely to mix the two reactants and the base, and maintain the mixture in the range 0° to 25°C. for several hours. The formula-XXXIX and XLVI bis(sulfonic acid) esters are then isolated by procedures known to the art.

Referring now to Chart D, bis(sulfonic acid) esters XXXIX are transformed either to oxa-phenylene PGE-type compounds XL, or to oxa-phenylene PGA-type compounds XLI. Referring to Chart E, bis(sulfonic acid) esters XLVI are transformed either to oxa-phenylene PGE-type compounds XLVII, or to oxa-phenylene PGA-type compounds XLVIII.

The transformations of XXXIX and XLVI to the PGE-type compounds XL and XLVII, respectively, are carried out by reacting bis-esters XXXIX and XLVI with water in the range about 0° to about 60°C. In making the oxa-phenylene $PGE_1$ compounds, 25° C. is a suitable reaction temperature, the reaction then proceeding to completion in about 5 to 20 hours. It is advantageous to have a homogenous reaction mixture. This is accomplished by adding sufficient of a water-soluble organic diluent which does not enter into the reaction. Acetone is a suitable diluent. The desired product is isolated by evaporation of excess water and diluent if one is used. The residue contains a mixture of formula-XL or formula-XLVII C-15 epimers which differ in the configuration of the side chain hydroxy, that being either "natural" or "epi," i.e. $\alpha$ or $\beta$. These are separated from by-products and from each other by silica gel chromatography. A usual by-product is the mono-sulfonic acid ester of formula XLII (Chart D) or formula XLIX (Chart E). These mono-sulfonic acid esters are esterified to the formula-XXXIX or -XLVI bis(sulfonic acid) esters, respectively, in the same manner described above for the transformation of glycol XXXVIII or XLV to bis-ester XXXIX or XLVI and thus are recycled back to additional formula-XL or -XLVII final product.

The transformations of XXXIX and XLVI to the PGA type compounds XLI and XLVIII, respectively, are carried out by heating bis-esters XXXIX and XLVI in the range 40° to 100° C. with a combination of water, a base characterized by its water solution having a pH 8 to 12, and sufficient inert water-soluble organic diluent to form a basic and substantially homogenous reaction mixture. A reaction time of one to 10 hours is usually used. Preferred bases are the water-soluble salts of carbonic acid, especially alkali metal bicarbonates, e.g., sodium bicarbonate. A suitable diluent is acetone. The products are isolated and separated as described above for the transformation of bis-esters XXXIX and XLVI to PGE-type products XL and XLVII. The same mono-sulfonic acid esters XLII and XLIX observed as by-products in those transformations are also observed during preparation of PGA-type products XLI and XLVIII.

For the transformations of bis(sulfonic acid) esters XXXIX and XLVI to final products XL, XLI, XLVII, and XLVIII, it is preferred to use the bis-mesyl esters, i.e., compounds XXXIX and XLVI wherein $R_{13}$ is methyl.

Referring again to Charts D and E, the configuration of the

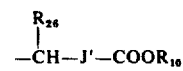

moiety in the formula-XXXIX bis-esters or the configuration of the

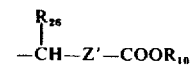

moiety in the formula-XLVI bis-esters does not change during these transformations of XXXIX to XL, XLI, and XLII and of XLVI to XLVII, XLVIII, and XLIX. Therefore, when in formula XXXIX for example, J' is

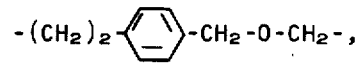

G' is $-(CH_2)_4-CH_3$, and $R_2$, $R_9$ and $R_{26}$ are hydrogen, natural- and epi-configuration 3-oxa-4,5-inter-o-phenylene-$PGE_1$ esters (XL) are obtained when

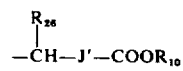

is attached initially (XXXIX) in alpha configuration, and natural- and epi-configuration 8-iso-3-oxa-4,5-inter-o-phenylene-$PGE_1$ esters (XL) are obtained when that moiety is attached in beta configuration. Similarly, when in formula XXXIX, J' is

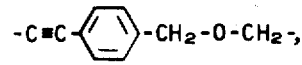

G' is $-(CH_2)_4-CH_3$, and $R_2$, $R_9$, and $R_{26}$ are hydrogen, natural- and epi-configuration 5,6-dehydro-3-oxa-4,5-inter-p-phenylene-$PGE_2$ esters are obtained when

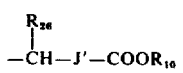

is attached initially in alpha configuration, and the corresponding 8-iso compounds are obtained when that moiety is attached in beta configuration. The same retention of

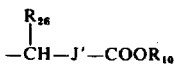

configuration occurs when formula-XLI and XLII compounds are produced, and a similar retention of

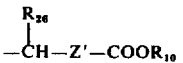

configuration occurs when formula-XLVII, XLVIII, and XLIX compounds are produced from formula-XLVI bis-esters.

The PGE$_3$-type oxa-phenylene compounds encompassed by formula XXXII are prepared by the transformations shown in Chart F, wherein $C_nH_{2n}$, M', Q, R$_2$, R$_5$, R$_9$R$_{10}$, R$_{13}$, THP, and ~ are as defined above.

Starting material, previously discussed, is converted to the formula-LXIX compound by several steps known in the art, employing first a Wittig reaction of a phosphonium salt of a haloalkyne of the formula BR—CHR$_2$—C$_n$H$_{2n}$—C ≡ C—R$_5$ wherein C$_n$H$_{2n}$, R$_2$, and R$_5$ are as defined above. See, for example, U. Axen et al., Chem. Comm. 1969, 303, and ibid. 1970, 602.

CHART F

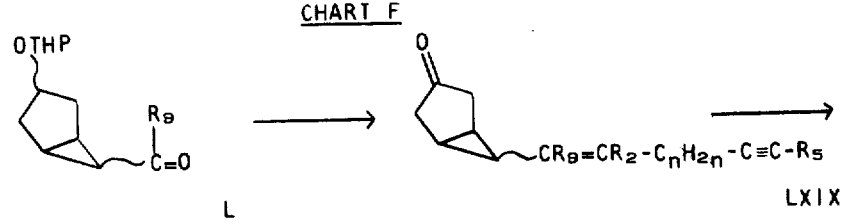

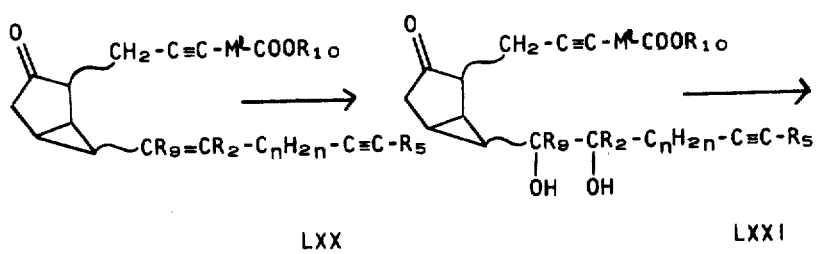

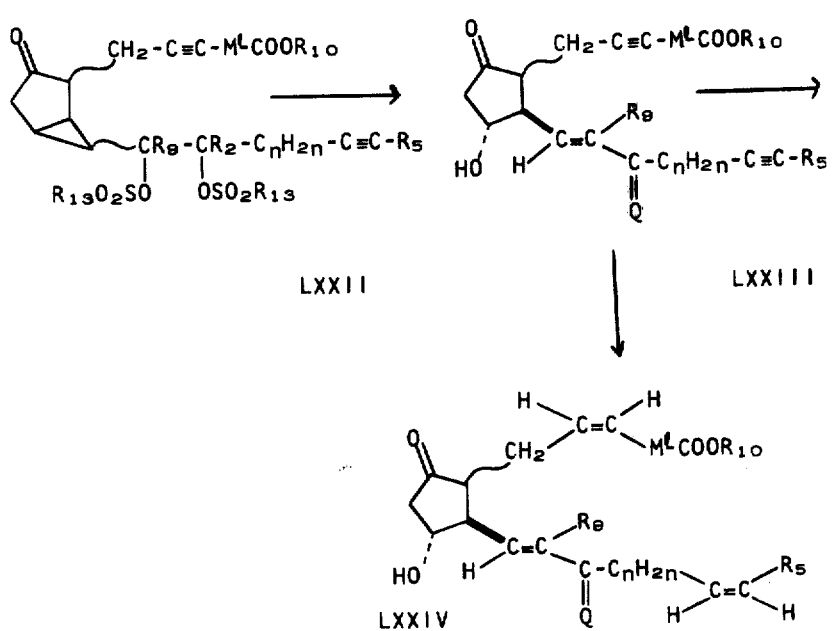

Compound LXIX is then alkylated with an alkylation agent of the formula Hal—CH$_2$—C≡C—M'—COOR$_{10}$ wherein M', R$_{10}$, and Hal are as defined above, i.e. M' is

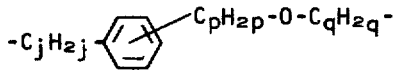

wherein C$_j$H$_{2j}$, C$_p$H$_{2p}$, and C$_q$H$_{2q}$ are as defined above, R$_{10}$ is the same as the definition of R$_1$ except that R$_{10}$ does not include hydrogen, and Hal is chloro, bromo, or iodo. These alkylating agents have been discussed above in connection with Charts D and E and the procedures for alkylation are similar to those employed in preparing the acetylenic compounds above. See also Axen et al., references cited.

Accordingly, for the preparation of 3-oxa-3,5-interm-phenylene-4-nor-PGE$_3$ compounds of formula XXXII wherein C$_j$H$_{2j}$ and C$_p$H$_{2p}$ are valence bonds, there is used an alkylating agent of the formula

prepare, for example, from compound LX as discussed above.

Referring again to Chart F, after alkylation, compound LXX is hydroxylated to glycol LXXI. Hydroxylation reagents and procedures for this purpose are known in the art. See also Axen et al., references cited.

Bis(alkanesulfonic acid) esters LXXII are prepared by reacting glycol LXXI with an alkanesulfonyl chloride or bromide, for example methanesulfonyl chloride in the presence of a tertiary amine, by methods known in the art.

Referring again to Chart F, bis(sulfonic acid) esters LXXII are transformed to oxa-phenylene bisdehydro PGE$_3$-type compounds LXXIII by reaction with water in the range about 0° to about 60° C., preferably in an acetone-water mixture, as known in the art and discussed hereinabove. See also Axen, references cited.

Transformation of LXXIII to the PGE$_3$-type compounds LXXIV is accomplished by hydrogenation of LXXIII using a catalyst which catalyzes hydrogenation of —C≡C— only to cis—CH=CH—, as known in the art and discussed hereinabove. Preferred is Lindlar catalyst in the presence of quinoline, see Axen, references cited.

The product is a mixture of formula-LXXIV C-15 epimers which are separated from by-products and from each other by silica gel chromatography.

The transformations of the formula-LXXIV PGE$_3$-type products to the corresponding PGF$_3$, PGA$_3$, and PGB$_3$ products are carried out by the steps shown in Chart A, discussed hereinabove.

The formula-LX and XLVII oxa-phenylene PGE-type compounds and the formula-XLI and XLVIII oxa-phenylene PGA-type compounds shown in Charts D and E and the formula-LXXIV oxa-phenylene PGE$_3$-type compounds shown in Chart F are all R$_{10}$ carboxylic acid esters, wherein R$_{10}$ is as defined above. Moreover when those PGE-type and PGA-type R$_{10}$ esters are used to prepare the other oxa-phenylene prostaglandin-like compounds according to Charts A, B, and C, corresponding R$_{10}$ esters are likely to be produced, especially in the case of the oxa-phenylene PGF-type compounds. For some of the uses described above, it is preferred that the novel formula XVI-to-XXXV oxa-phenylene prostaglandin-like compounds of this invention be in free acid form, or in salt form which requires the free acid as a starting material. Likewise, when a formula XVI-to-XXXV oxa-phenylene prostaglandin-like compound is available as an ester, say the methyl ester, and another ester is desired, it is usually necessary to convert the available ester to the free acid form and from it prepare the desired ester. Esters are prepared by methods known in the art or described herein, for example by reaction with diazohydrocarbons.

The PGF-type esters of formulas XX-XXIII and XXXIII and the PGB-type compounds of formulas XXVIII-XXXI and XXXV are easily hydrolyzed or saponified to the free acids by the usual known procedures, especially when R$_1$ (R$_{10}$) is alkyl of one to 4 carbons, inclusive, preferably methyl or ethyl.

On the other hand, the PGE type esters of formulas XVI-XIX and XXXII and the PGA type esters of formulas XXIV-XXVII and XXXIV are difficult to hydrolyze or saponify without causing unwanted structural changes in the desired acids. There are two other procedures to make the free acid forms of these PGE- and PGA-type compounds.

One of those procedures is applicable mainly in preparing the free acids by subjecting their alkyl esters to the acylase enzyme system of a microorganism species of Subphylum 2 of Phylum III, and thereafter isolating the acid. See West Germany Offenlegungsschrift No. 1,937,678; Derwent Farmdoc No. 6863R. This enzymatic hydrolysis is also applicable to the above PGF- and PGB-type alkyl esters. Another method using an esterase enzyme composition from P. homomalla is described in U.S. Pat. No. 3,761,356.

Another procedure for making the free acids of the above PGE- and PGA-type compounds involves treatment of certain haloethyl esters of those acids with zinc metal and an alkanoic acid of 2 to 6 carbon atoms, preferably acetic acid. Those haloethyl esters are the esters wherein R$_{10}$ is ethyl substituted in the β-position with 3 chloro, 2 or 3 bromo, or one, 2, or 3 iodo. Of those haloethyl moieties, β,β,β-trichloroethyl is preferred. Zinc dust is preferred as the physical form of the zinc. Mixing the haloethyl ester with the zinc dust at about 25° C. for several hours usually causes substantially complete replacement of the haloethyl moiety of the formula XVI-XIX, XXXII, XXIV-XXVII, and XXXIV ester with hydrogen. The free acid is then isolated from the reaction mixture by procedures known to the art. This procedure is also applicable to the production of PGF- and PGB-type free acids.

Formula-XXXVII cyclic ketals and formula XLIV olefins wherein R$_{10}$ is haloethyl as above defined are necessary as intermediates for this route to the final PGE, PGF, PGA, and PGB type free acids. These formula-XXXVII and -XLIV haloethyl ester intermediates can be prepared by alkylation of cyclic ketal XXXVI (Chart D) or olefin XLIII (Chart E), respectively, with the appropriate formula LIII-to-LVI or LXVII-LXVIII alkylating agent wherein R$_{10}$ is haloethyl as above defined. However, preferred routes of the formula-XXXVII and -XLIV haloethyl ester intermediates are shown in Charts G and H.

In Charts G and H, G, J', R$_2$, R$_9$, R$_{26}$, R$_{11}$, R$_{12}$, Z', and ~ are as defined above. Haloethyl represents ethyl substituted in the β-position with 3 chloro, or 2 or 3 bromo, or 1, 2, or 3 iodo, preferably —CH$_2$CCl$_3$. R$_{15}$ represents alkyl of one to 4 carbon atoms, inclusive, preferably methyl or ethyl.

CHART G
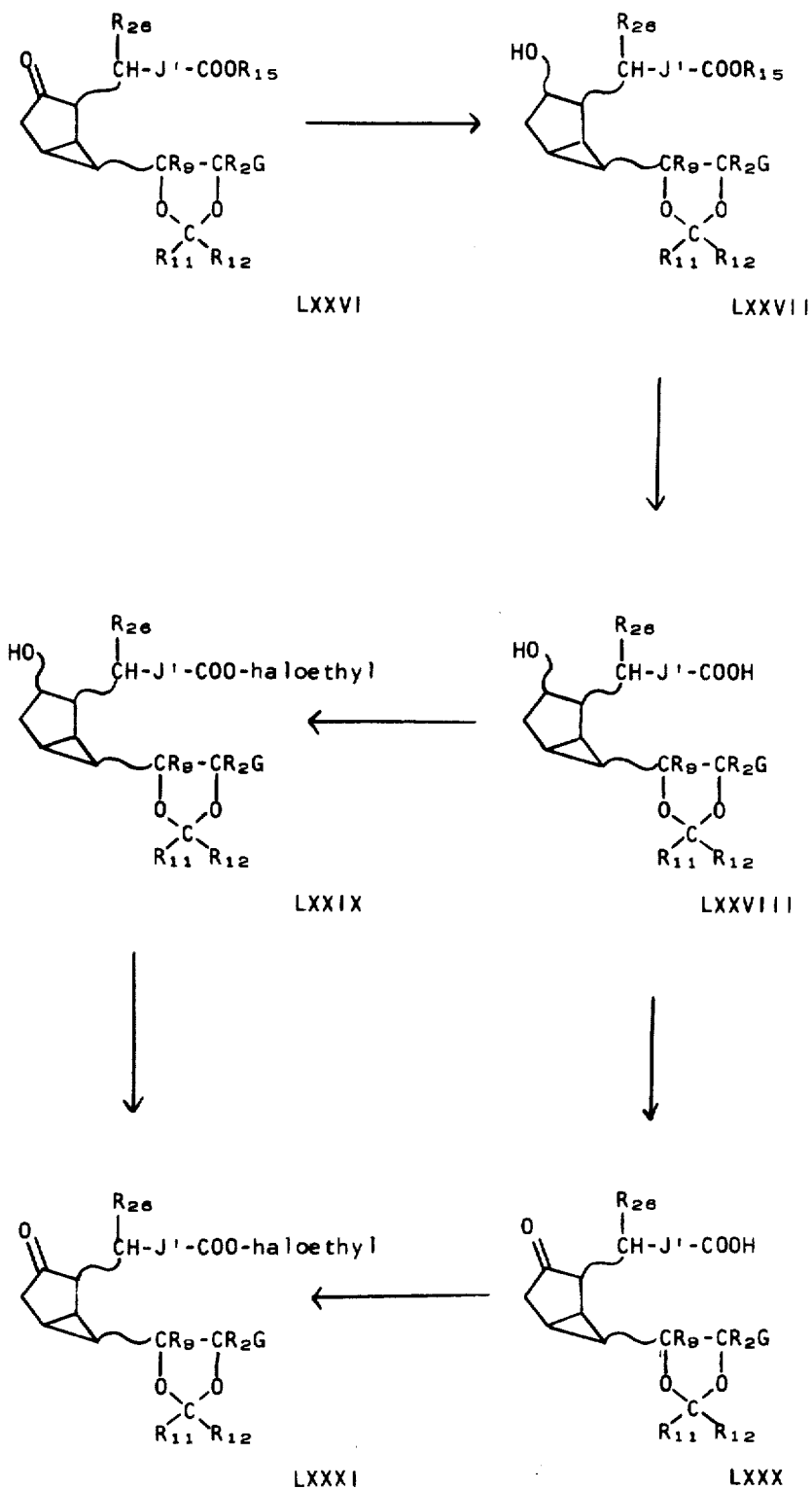

CHART H

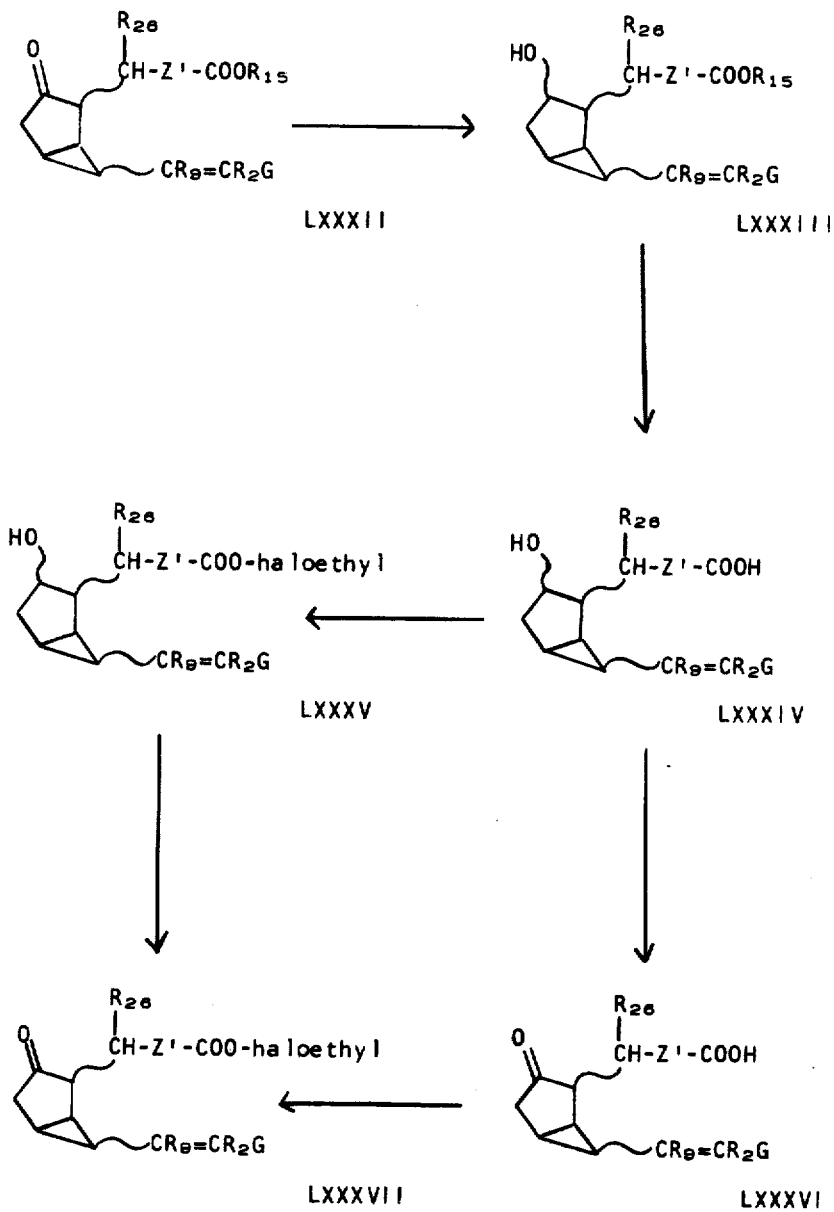

Compound LXXVI in Chart G is within the scope of compound XXXVII in Chart D. Compound LXXXII in Chart H is within the scope of compound XLIV in Chart E. These ketones LXXVI and LXXXII are reduced to corresponding hydroxy compounds LXXVII and LXXXIII, respectively, with a carbonyl reducing agent, e.g., sodium borohydride, as described above in discussion of Chart A. Then, hydroxy esters LXXVII and LXXXIII are saponified by known procedures to hydroxy acids LXXVIII and LXXXIV, respectively. These two hydroxy acids are transformed to keto haloethyl esters LXXXI and LXXXVI, respectively, by oxidation of the hydroxy group to keto and esterification of the carboxyl group to —COO-haloethyl. As shown in Charts G and H, these two reactions are carried out in either order. However, it is preferred to oxidize first and then esterify.

Hydroxy acids LXXVIII and LXXXIV are oxidized to keto acids LXXX and LXXXVI, respectively, and hydroxy haloesters LXXIX and LXXXV are oxidized to keto haloesters LXXXI and LXXXVII, respectively, by reaction with an oxidizing agent which does not attack other parts of these molecules, especially the cyclic ketal group of compounds LXXVIII and LXXIX or ethylenic linkage of compounds LXXIV and LXXXV. An especially useful reagent for this purpose is the Jones reagent, i.e., acidic chromic acid. Acetone is a suitable diluent for this purpose, and a slight excess of oxidant and temperatures at least as low as about 0° C., preferably about −10° to about −20° C. should be used. The oxidation proceeds rapidly and is usually complete in about 5 to about 30 minutes. Excess oxidant is destroyed, for example, by addition of a lower alkanol, advantageously isopropyl alcohol, and the aldehyde is isolated by conventional methods, for example, by extraction with a suitable solvent, e.g., diethyl ether. Other oxidizing agents can also be used. Examples are mixtures of chromium trioxide and pyridine or mixtures of dicyclohexylcarbodiimide and dimethyl sulfoxide. See, for example, J. Am. Chem. Soc. 87, 5661 (1965).

Haloethyl esters LXXIX, LXXXI, LXXXV, and LXXXVII are prepared by reacting agents LXXVIII, LXXX, LXXXIV, and LXXXVI respectively, with the appropriate haloethanol, e.g., β,β,β-trichloroethanol, in the presence of a carbodiimide, e.g., dicyclohexylcarbodiimide, and a base, e.g., pyridine, preferably in the presence of an inert liquid diluent, e.g., dichloromethane, for several hours at about 25° C.

As described above, the alkylations of cyclic ketal XXXVI to XXXVII (Chart D) and olefin XLIII and XLIV (Chart E) usually produce mixtures of alpha and beta alkylation products with respect to the

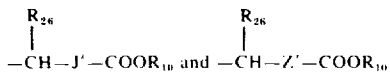

moieties. Also as described above, those two isomers lead to different final products, alpha leading to the PG-type series and beta leading to the 8-iso-PG-type series. If a compound in one or the other of those two series is preferred, there are two methods for favoring production of the preferred final product.

One of those methods involves isomerization of the final product of formulas XVI to XXXV. Either the alpha isomers of a formula XVI-to-XXXV compound, ester or free acid, or the corresponding beta isomer is maintained in a inert liquid diluent in the range 0° to 80° C. and in the presence of a base characterized by its water solution having a pH below about 10 until a substantial amount of the isomer has been isomerized to the other isomer, i.e., alpha to beta or beta to alpha. Preferred bases for this purpose are the alkali metal salts of carboxylic acids, especially alkanoic acids of 2 to 4 carbon atoms, e.g., sodium acetate. Examples of useful inert liquid diluents are alkanols of one to 4 carbon atoms, e.g., ethanol. This reaction at about 25° takes about one to about 20 days. Apparently an equilibrium is established. The mixtures of the two isomers, alpha and beta, are separated from the reaction mixture by known procedures, and then the two isomers are separated from each other by known procedures, for example, chromatography, recrystallization, or a combination of those. The less preferred isomer is then subjected to the same isomerization to produce more of the preferred isomer. In this manner by repeated isomerizations and separations, substantially all of the less preferred isomer of the formula XVI-to-XXXV compound is transformed to more preferred isomer.

The second method for favoring production of a preferred formula XVI-to-XXXV isomer involves any one of the keto intermediates of formulas XXXVII, XXXVIII, XLIV, XLV, LXX, or LXXI (Charts D, E, and F). Either the alpha form or the beta form of one of those intermediates is transformed to a mixture of both isomers by maintaining one or the other isomer, alpha or beta, in an inert liquid diluent in the presence of a base and in range 0°to 100° C. until a substantial amount of the starting isomer has been isomerized to the other isomer. Preferred bases for this isomerization are alkali metal amides, alkalie metal alkoxides, alkali metal hydrides, and triarylmethyl alkali metals. Especially preferred are alkali metal tert-alkoxides of 4 to 8 carbon atoms, e.g., potassium tert-butoxide. This reaction at about 25° C. proceeds rapidly (one minute to several hours). Apparently an equilibrium mixture of both isomers is formed, starting with either isomer. The isomer mixtures in the equilibrium mixture thus obtained are isolated by known procedures, and then the two isomers are separated from each other by known procedures, for example, chromatography. The less preferred isomer is then subjected to the same isomerization to produce more of the preferred isomer. In this manner, by repeated isomerizations and separations, substantially all of the less preferred isomer of any of these intermediates in transformed to the more preferred isomer. Cyclic ketalketone intermediates of formula XXXVII are preferred over the other intermediates for this isomerization procedure.

The novel oxa-phenylene PGE, PGF, PGA and PGB type compounds of formula XVI to XXXV wherein $R_2$ is alkyl of one to 4 carbon atoms, inclusive, preferably methyl or ehtyl, are preferred over the corresponding oxa-phenylene PGE, PGF, PGA, and PGB type compounds in which $R_2$ is hydrogen for the above-described pharmacological purposes.

These 15-alkyl prostaglandin analogs are suprisingly and unexpectedly more useful than the corresponding 15-hydrogen compounds for the reason that they are substantially more specific with regard to potency in causing prostaglandin-like biological responses, and have substantially longer duration of biological activity. For that reason, fewer and smaller doses of these 15-alkyl prostaglandin analogs are needed to attain the desired pharmacological results.

Although the above-mentioned 15-alkyl compounds are produced by the methods outlined above in Charts A–F, the preferred methods are set forth in Chart I and J as follows.

In Chart I is shown the transformation of 15-alkyl PGF-type acids and alkyl esters to the corresponding PGE-type acids and alkyl esters by oxidation. For this purpose, and oxidizing agent is used which selectively oxidizes secondary hydroxy groups to carbonyl groups in the presence of carbon-carbon double bonds. Formula LXXXVIII in Chart I includes optically active compounds as shown and racemic compounds of that formula and the mirror images thereof, and also the 15-epimers of both of those, i.e., wherein the configuration at C-15 is β rather than α as shown. Also in Chart I, E', G, J', $R_1$ and $R_{26}$ are as defined above, and $R_{16}$ is alkyl of one to 4 carbon atoms.

For the transformations of Chart I, the β-hydroxy isomers of reactant LXXXVIII are preferred starting materials when the carboxyl side chain is alpha, although the corresponding α-hydroxy isomers are also useful for this purpose.

Oxidation reagents useful for the transformation set forth in Chart I are known to the art. An especially useful reagent for this purpose is the Jones reagent, i.e., acidified chromic acid. See J. Chem. Soc. 39 (1946). A slight excess beyond the amount necessary to oxidize one of the secondary hydroxy groups of the formula-LXXXVIII reactant is used. Acetone is a suitable diluent for this purpose. Reaction temperatures at least as low as about 0° C. should be used.

CHART I
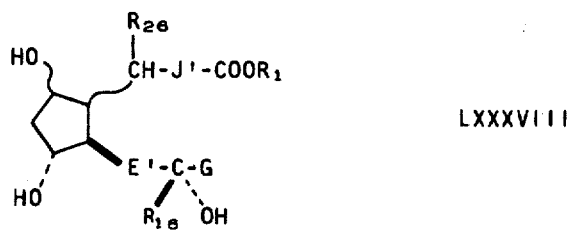
LXXXVIII
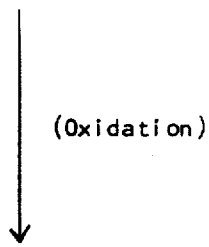  (Oxidation)
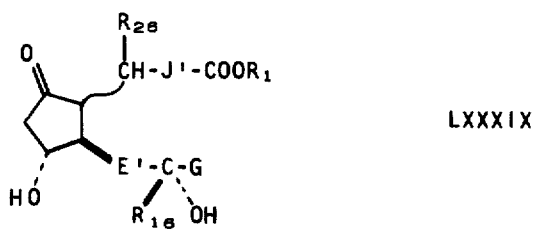
LXXXIX
CHART J
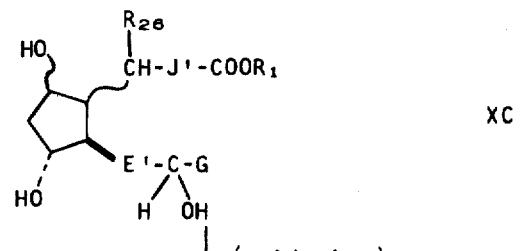
XC
 (oxidation)
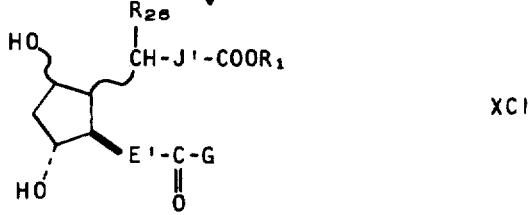
XCI
(silylation)
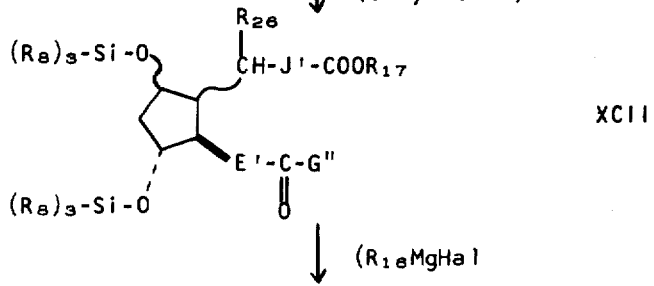
XCII
($R_{18}$MgHal)

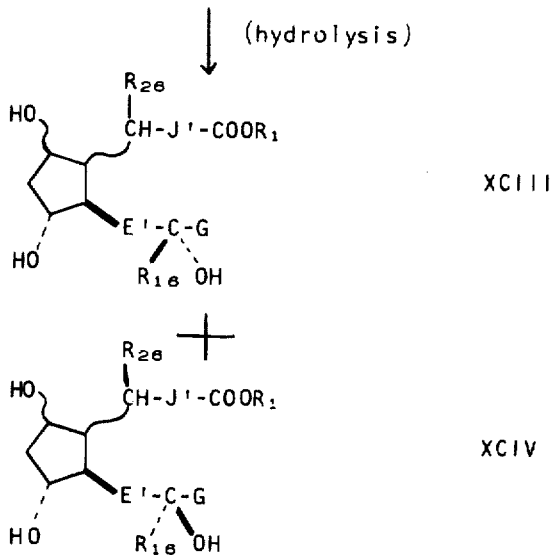

Preferred reaction temperatures are in the range −10° to −50° C. The oxidation proceeds rapidly and is usually complete in about 5 to 20 minutes. The excess oxidant is destroyed, for example by addition of a lower alkanol, advantageously, isopropyl alcohol, and the formula-LXXXIX PGE-type product is isolated by conventional methods.

Examples of other oxidation reagents useful for the Chart H transformations are silver carbonate on Celite (Chem. Commun. 1102 (1969)), mixtures of chromium trioxide and pyridine (Tetrahedron Letters 3363 (1968), J. Am. Chem. Soc. 75, 422 (1953), and Tetrahedron, 18, 1351 (1962)), mixtures of sulfur trioxide in pyridine and dimethyl sulfoxide (J. Am. Chem. Soc. 89, 5505 (1967)), and mixtures of dicyclohexylcarbodiimide and dimethyl sulfoxide (J. Am. Chem. Soc. 87, 5661 (1965)).

The novel 15-alkyl oxa-phenylene $PGF_\alpha$ - and $PGF_\beta$ -type acids and esters of formulas XX-XXIIII and XXXIII wherein $R_2$ is one to 4 carbon atoms, inclusive, are preferably prepared from the corresponding 15-hydrogen compounds by the sequence of transformations shown in Chart J, wherein formulas XC through XCIV, inclusive, include optically active and racemic natural- and epi-configuration compounds of those formulas and the mirror images thereof. Also in Chart J, $R_{16}$ is alkyl of one to 4 carbon atoms, inclusive, and E', G, Hal, J', $R_1$, $R_{26}$, and ∼ are as heretofore defined; G'' in formula XCII is the same as G except that T is replaced by T'', wherein T'' is the same as T above except that, in $R_6$, $-Si(R_8)_3$ replaces hydrogen. Also in Chart J, $R_8$ is alkyl of one to 4 carbon atoms, inclusive, aralkyl of 7 to 12 carbon atoms, inclusive, phenyl, or phenyl substituted with one or 2 fluoro, chloro, or alkyl of one to 4 carbon atoms inclusive, and $R_{17}$ is $R_1$ as defined above or silyl of the formula-$Si-(R_8)_3$ wherein $R_8$ is as defined above. The various $R_8$'s of a $-Si(R_8)_3$ moiety are alike or different. For example, a $-Si(R_8)_3$ can be trimethylsilyl, dimethylphenylsilyl, or methylphenylbenzylsilyl. Examples of alkyl of one to 4 carbon atoms, inclusive, are methyl, ethyl, propyl, isopropyl, butyl, isobutyl, sec-butyl, and tert-butyl. Examples of aralkyl of 7 to 12 carbon atoms, inclusive, are benzyl, phenethyl, α-phenylethyl, 3-phenylpropyl, α-naphthylmethyl, and 2-(β-naphthyl)ethyl. Examples of phenyl substituted with one or 2 fluoro, chloro, or alkyl of one to 4 carbon atoms, inclusive, are p-chlorophenyl, m-fluorophenyl, o-tolyl, 2,4-dichlorophenyl, p-tert-butylphenyl, 4-chloro-2-methylphenyl, and 2,4-dichloro-3- methylphenyl.

In Chart J, the final PGF and PGF -type products are those encompassed by formulas XCIII and XCIV, respectively.

The initial optically active or racemic reactants of formula XC in Chart J i.e., the oxa-phenylene $PGF_1$-, $PGF_2$-, 5,6-dehydro-$PGF_2$-, and dihydro-$PGF_1$-type compounds in their α and β forms, and their esters, are prepared by methods described herein. Thus, racemic oxa-phenylene dihydro-$PGF_1$ - and -$PGF_1$ -type compounds, and their esters are prepared by catalytic hydrogenation of the corresponding racemic oxa-phenylene $PGF_1$ or $PGF_2$, and $PGF_1$ or $PGF_2$ type compounds, respectively, e.g. in the presence of 5% palladium-on-charcoal catalyst in ethyl acetate solution at 25° C. and one atmosphere pressure of hydrogen.

The heretofore-described acids and esters of formula XC are transformed to the corresponding intermediate 15-dehydro acids and esters of formula XCI, by oxidation with reagents such as 2,3-dichloro-5,6-dicyano-1,4-benzoquinone, activated manganese dioxide, or nickel peroxide (see Fieser et al., "Reagents for Organic Syntheses," John Wiley & Sons, Inc., New York, N.Y. pp. 215, 637, and 731). Alternatively, and especially for the formula-XC reactants wherein E' is $-CH_2CH_2$ and J' is L as defined above, these oxidations are carried out by oxygenation in the presence of the 15-hydroxyprostaglandin dehydrogenase of swine lung (see Arkiv för Kemi 25, 293 (1966)). These reagents are used according to procedures known in the art. See, for example, J. Biol. Chem. 239, 4097 (1964).

Referring again to Chart J, intermediate compounds of formula XCI are transformed to silyl derivatives of formula XCII by procedures known in the art. See, for example, Pierce, "Silylation of Organic Compounds,"

Pierce Chemical Co., Rockford, Ill. (1968). Both hyroxy groups of the formula-XCI reactants are thereby transformed to —O—Si($R_8$)$_3$ moieties wherein $R_8$ is as defined above, and sufficient of the silylating agent is used for that purpose according to known procedures. When $R_1$ in the formula-XCI intermediate is hydrogen, the —COOH moiety thereby defined is simultaneously transformed to —COO—Si($R_8$)$_3$, additional silylating agent being used for this purpose. This latter transformation is aided by excess silylating agent and prolonged treatment. Likewise, when $R_6$ in T of the formula-XCI intermediate is hydrogen, the phenolic hydroxyl thereby defined is simultaneously transformed to —O—Si($R_8$)$_3$ in the silylation step. G'' in formula XCII, as defined above, therefore is the same as G except that T is replaced by T'', wherein T'' is the same as T above except that, in $R_6$, —Si($R_8$)$_3$ replaces hydrogen. When $R_1$ in formula XCI is alkyl, then $R_{17}$ in formula XCII will also be alkyl. The necessary silylating agents for these transformations are known in the art or are prepared by methods known in the art. See, for example, Post, "Silicones and Other Organic Silicon Compounds," Reinhold Publishing Corp., New York, N.Y. (1949).

Referring again to Chart J, the intermediate silyl compounds of formula XCII are transformed to the final compounds of formulas XCIII and XCIV by first reacting the silyl compound with a Grignard reagent of the formula $R_{16}$MgHal wherein $R_{16}$ is as defined above, and Hal is chloro, bromo, or iodo. For this purpose, it is preferred that Hal be bromo. This reaction is carried out by the usual procedure for Grignard reactions, using diethyl ether as a reaction solvent and saturated aqueous ammonium chloride solution to hydrolyze the Grignard complex. The resulting disilyl, trisilyl, or tetrasilyl tertiary alcohol is then hydrolyzed with water to remove the silyl groups. For this purpose, it is advantageous to use a mixture of water and sufficient of a water-miscible solvent, e.g., ethanol to give a homogeneous reaction mixture. The hydrolysis is usually complete in 2 to 6 hours at 25° C., and is preferably carried out in an atmosphere of an inert gas, e.g., nitrogen or argon.

The mixture of 15-$\alpha$ and 15-$\beta$ isomers obtained by this Grignard reaction and hydrolysis is separated by procedures known in the art for separating mixtures of prostanoic acid derivatives, for example, by chromatography on neutral silica gel. In some instances, the lower alkyl esters, especially the methyl esters of a pair of 15-$\alpha$ and 15-$\beta$ isomers are more readily separated by silica gel chromatography than are the corresponding acids. In those cases, it is advantageous to esterify the mixture of acids as described below, separate the two esters, and then, if desired, saponify the esters by procedures known in the art for saponification of prostaglandins F.

Although formula-XCIII and -XCIV compounds wherein E' is —CH$_2$CHR$_9$—and J' is L' as defined above may be produced according to the processes of Chart J, it is preferred to produce those novel dihydro-PGF$_1$ analogs by hydrogenation of one of the corresponding unsaturated compounds, i.e., a compound of formula XCIII or XCIV wherein E is trans —CH=CR$_9$- —and J' is either L', —CH=CH—M'—, —C ≡ C—M'- , M' being defined above. This hydrogenation is advantageously carried out catalytically, for example, in the presence of a 5% palladium-on-charcoal catalyst in ethyl acetate solution at 25° C. and one atmosphere pressure of hydrogen.

The novel 15-alkyl oxa-phenylene PGA-type and PGB-type acids and esters of formula XXIV-XXXI and XXXIV-XXXV are prepared from the 15-alkyl oxa-phenylene PGE compounds, heretofore described, by dehydrations and double bond migrations previously described, as shown in Chart A. Likewise the 15-alkyl PGB-type compounds are prepared by contacting the 15-alkyl PGA-type compounds with base. For the transformation of the 15-alkyl PGE-type compounds to the 15-alkyl PGA-type compounds of this invention (Chart K), it is preferred that a dehydrating agent be used which removes

CHART K

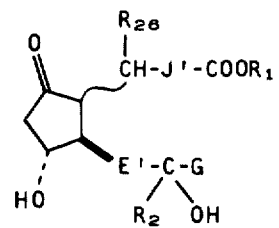

XCV

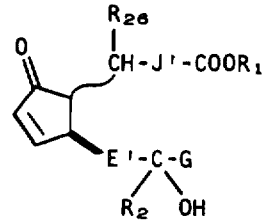

XCVI the hydroxy group from the alicyclic ring in the presence of a hydroxy group on a tertiary carbon atom. In Chart K, E', G, J', $R_1$, $R_2$, $R_{26}$, and ~ are as defined above. Formula XCV as shown includes optically active compounds and racemic compounds of that formula and the mirror images thereof, and also the 15-epimers of both of those. Any of the known substantially neutral dehydrating agents is used for these reactions. See Fieser et al., cited above. Preferred dehydrating agents are mixtures of at least an equivalent amount of a carbodiimide and a catalytic amount of a copper (II) salt. Especially preferred are mixtures of at least an equivalent amount of dicyclohexyl carbodiimide and a catalytic amount of copper (II) chloride. An equivalent amount of a carbodiimide means one mole of the carbodiimide for each mole of the formula-XCV reactant. To ensure completeness of the reaction, it is advantageous to use an excess of carbodiimide, i.e., 1.5 to 5 or even more equivalents of the carbodiimide.

The dehydration is advantageously carried out in the presence of an inert organic diluent which gives a homogeneous reaction mixture with respect to the formula-XCV reactant and the carbodiimide. Diethyl ether is a suitable diluent. It is advantageous to carry out the dehydration in an atmosphere of an inert gas, e.g., nitrogen, helium, or argon. The time required for the dehydration will depend in part on the reaction temperature. With the reaction temperature in the range 20° to 30°C., the dehydration usually takes place in about 40 to 60 hours. The formula-XCVI product is isolated by methods known in the art, e.g., filtration of the reaction mixture and evaporation of the filtrate. The product is then purified by methods known in the art, advantageously by chromatography on silica gel.

The final formula XVI-to-XXXV compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the formula XVI-to-XXXV acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the formula XVI-to-XXXV acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the formula XVI-to-XXXV acid with the stoichiometric amount of the corresponding quaternary ammonium hydroxide in water solution, followed by evaporation of the water.

The final formula XVI-to-XXXV acids or esters prepared by the processes of this invention are transformed to lower alkanoates by interaction of the formula XVI-to-XXXV hydroxy compound with a carboxyacylating agent, preferably the anhydride of a lower alkanoic acid, i.e., an alkanoic acid of one to 8 carbon atoms, inclusive. For example, use of acetic anhydride gives the corresponding diacetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent. An inert inorganic diluent, for example, dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography.

By this procedure, the formula XVI-XIX and XXXII PGE-type compounds are transformed to dialkanoates, the formula XX-XXIII and XXXIII PGF-type compounds are transformed to trialkanoates, and the formula XXIV-XXXI and XXXIV-XXXV PGA-type and PGB-type compounds are transformed to monoalkanoates.

When a PGE-type dialkanoate is transformed to a PGF-type compound by carbonyl reduction as shown in Chart A, a PGF-type dialkanoate is formed and is used for the above-described purposes as such or is transformed to a trialkanoate by the above-described procedure. In the latter case, the third alkanoyloxy group can be the same as or different from the two alkanoyloxy groups present before the carbonyl reduction.

Molecules of each of the compounds encompassed by formulas XVI to XXXV and, except for XLIII and L, of each intermediate formula each have at least one center of asymmetry, and each can exist in racemic form and in either enantiomeric form, i.e., d and l. A formula accurately defining the d form would be the mirror image of the formula which defined the l form. Both formulas are necessary to define accurately the corresponding racemic form. The various formulas XVI-to-XXXV as drawn each represents the optically active form with the same configuration as the naturally-occurring prostaglandins.

When an optically active (d or l) final compound is desired, that is made by resolution of the racemic compound or by resolution of one of the asymmetric racemic intermediates. These resolutions are carried out by procedures known in the art. For example, when final compound XVI to XXXV is a free acid, the dl form thereof is resolved into the d and l forms by reacting said free acid by known general procedures with an optically active base, e.g., brucine or strychnine, to give a mixture of two diastereoisomers which are separated by known general procedures, e.g., fractional crystallization, to give the separate diastereoisomeric salts. The optically active acid of formula XVI to XXXV is then obtained by treatment of the salt with an acid by known general procedures. Alternatively, the free acid form of cyclic ketal XXXVII, olefins XLIV or LXX, or glycols XXXVIII, XLV, or LXXI is resolved into separate $d$ and $l$ forms and then esterified and transformed further to the corresponding optically active form of the final product XVI to XXXV as described above.

In another method, bicyclo ketone reactants XXXVIII, XLV, or LXXI in exo or endo form, are transformed to ketals with an optically active 1,2-glycol, e.g., D-(—)-2,3-butanediol, by reaction of said 1,2-glycol with the formula-XXXVIII, XLV, or LXXI compound in the presence of a strong acid, e.g., p-toluenesulfonic acid. The resulting ketal is a mixture of diastereoisomers which is separated into the d and l diastereoisomers, each of which is then hydrolyzed with an acid, e.g., oxalic acid, to the original keto compound, now in optically active form. These reactions involving optically active glycols and ketals for resolution purposes are generally known in the art. See, for example, Chem. Ind. 1664 (1961) and J. Am. Chem. Soc. 84, 2938 (1962). Dithiols may be used instead of glycols.

Still another procedure for obtaining optically active oxa-phenylene PGF-type compounds is by stereoselective microbiological reduction of the racemic oxa-phenylene PGE compounds. For this purpose actively fermenting baker's yeast is employed. The PGE compound is contacted with a yeast-sugar-water mixture at about 25° C. for 24–48 hours. There is produced by reduction a mixture of the $PGF_\alpha$ compound and the enantiomeric $PGF_\beta$ compound, which are separable by silica gel chromatography for example. Accompanying this transformation, carboxylic ester groups are removed by hydrolysis. Accordingly, from dl-3-oxa-3,7-inter-m-phenylene-4,5,6-trinor-$PGE_1$ methyl ester, there are obtained natural configuration 3-oxa-3,7-inter-m-phenylene-4,5,6-trinor-$PGF_{1\alpha}$ and enantiomeric 3-oxa-3,7-inter-m-phenylene-4,5,6-trinor-$PGF_{1\beta}$.

An alternate method of synthesis is provided hereinafter for a group of oxa-phenylene analogs within the scope of formulas XVI and XX above, represented by the following formulas XCVII–CIV;

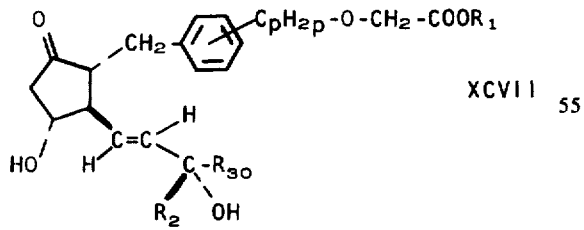

and the racemic mixtures of those compounds and their respective enantiomers represented by the mirror images of the above formulas. The terms $C_pH_{2p}$, $C_tH_{2t}$, $R_1$, $R_2$, T, and s are as defined above; $R_{30}$ is alkyl of 2 to 10 carbon atoms, inclusive, substituted with zero, one, 2, or 3 fluoro.

The alternate method of synthesis disclosed hereinafter is also useful for preparing oxa-phenylene 17,18-didehydro prostaglandin analogs within the scope of formulas CV–CVIII:

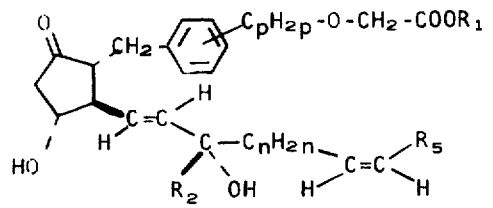
CV

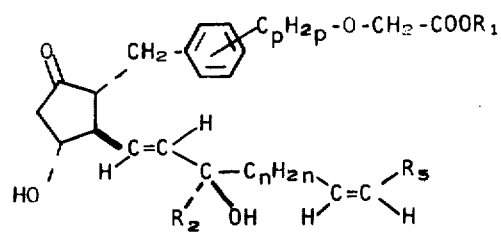
CVI

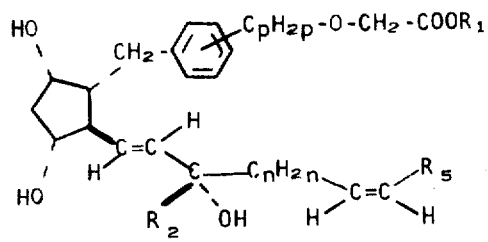
CVII

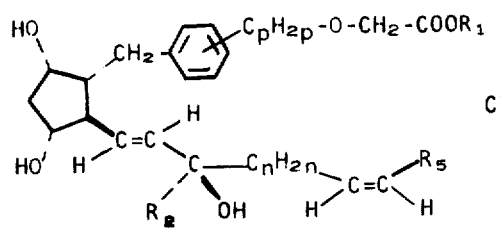
CVIII wherein $C_nH_{2n}$, $C_pH_{2p}$, $R_1$, $R_2$, and $R_5$ are as defined and used above.

These 17,18-didehydro analogs of formulas CV–CVIII together with compounds of formulas XXXII and XXXIII above are within the scope of 17,18-didehydro PGE- and PGF-type compounds represented by the formulas:

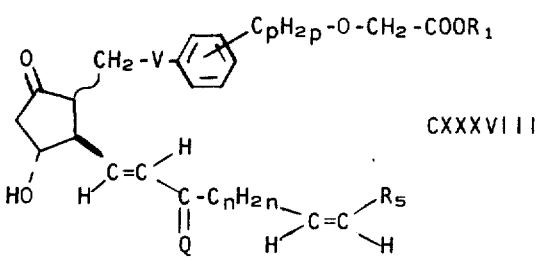
CXXXVIII

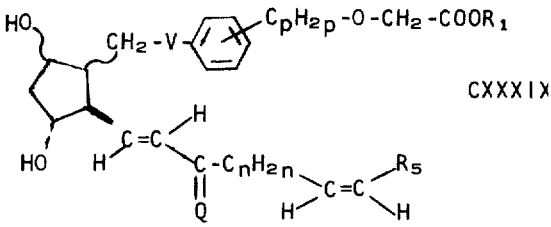
CXXXIX wherein ~ indicates attachment of the hydroxyl or the side chain to the cyclopentane ring in alpha or beta configuration; wherein V is (1) $C_gH_{2g}$ or (2) —CH=λCH—$C_jH_{2j}$—, wherein $C_gH_{2g}$ represents a valence bond or alkylene of one to 4 carbon atoms, inclusive, with one or 2 chain carbon atoms between —$CH_2$— and the phenylene ring, and wherein $C_jH_{2j}$ represents a valence bond or alkylene of one or 2 carbon atoms with one chain carbon atom between —CH=CH— and the phenylene ring; wherein $C_nH_{2n}$ is alkylene of one to 4 carbon atoms, inclusive; wherein $C_pH_{2p}$ represents a valence bond or alkylene of one to 4 carbon atoms, inclusive, with one or 2 chain carbon atoms between the ring and —O—; wherein $C_gH_{2g}$ and $C_pH_{2p}$ together represent zero to 8 carbon atoms, inclusive, with total chain lengths zero to 3 carbon atoms, inclusive; wherein Q is

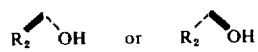

wherein $R_2$ is hydrogen or alkyl of one to 4 carbon atoms, inclusive; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive; and wherein $R_5$ is alkyl of one to 4 carbon atoms, inclusive, substituted with zero, one, 2, or 3 fluoro.

The corresponding 17,18-didehydro PGA- and PGB-type compounds are available by methods disclosed herein or known in the art, for example by acid or base dehydration of the formula-CXXXVII PGE-type compounds.

The alternate method of synthesis utilizes oxetane intermediates having the grouping

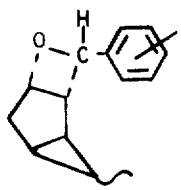

prepared from bicyclo hexene starting materials.

Reference to Chart L will make clear the steps by which starting material CIX is transformed to product CXVIII. The formula-CIX compound wherein $R_{31}$ and $R_{32}$ together are $-CH_2-C(CH_3)_2-CH_2-$ and $\sim$ is endo, i.e. bicyclo[3.1.0]hex-2-ene-6-endo-carboxaldehyde neopentyl glycol acetal, is available either in racemic or optically active form. See U.S. Pat. No. 3,711,515.

In Chart L the symbols used therein have the same meanings as defined above, as to $C_pH_{2p}$, G, Q, $R_1$, $R_2$, $R_{31}$, $R_{32}$, $R_{39}$, $R_{42}$, and $\sim$. $R_{43}$ represents hydrogen, carboxyacyl $R_{39}$, benzoyl, substituted benzoyl, monoesterified phthaloyl, and substituted naphthoyl. Furthermore, in Chart L and likewise in the other charts of this specification, the formulas as drawn represent specific optical isomers following the conventions applied herein to the end products. However, for purposes of convenience and brevity it is intended that such representations of the process steps for the optically active intermediates are applicable to those same process steps as used for the corresponding racemic intermediates.

Both the endo and exo forms of bicyclo hexene CIX are available or are made by methods known in the art, in either their racemic or optically active forms. See. U.S. Pat. No. 3,711,515.

CHART L

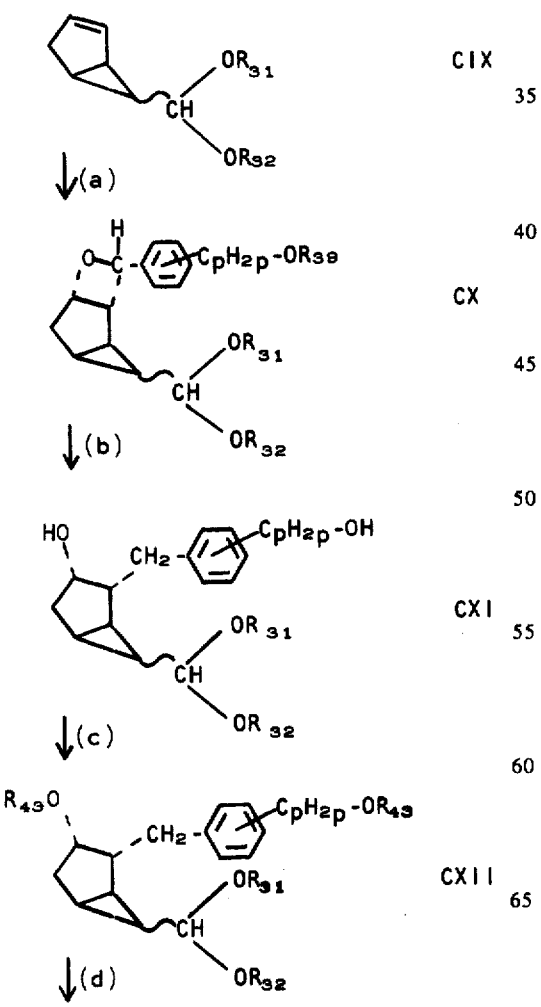

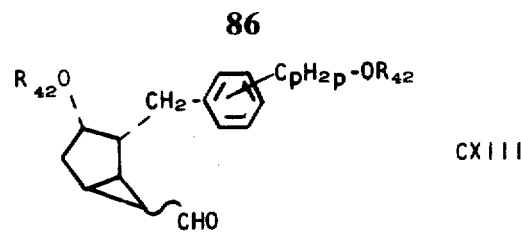

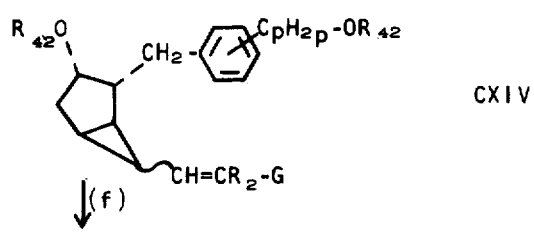

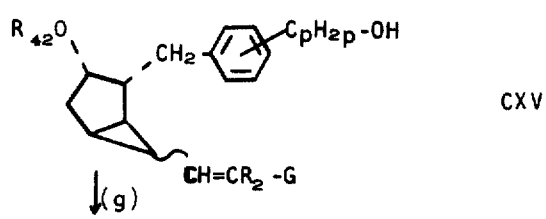

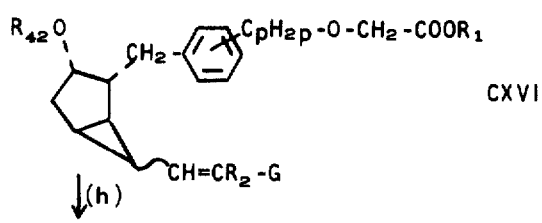

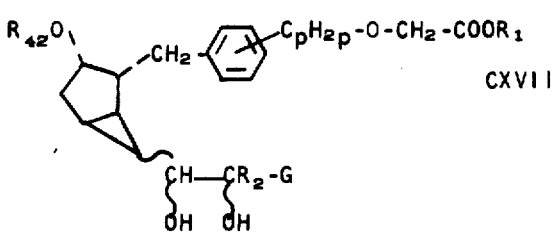

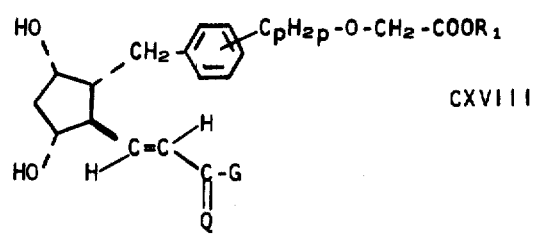

Either the endo or exo starting material will yield the ultimate analogs of formula CXVIII by the processes of Chart L.

In step (a) oxetane CX is obtained by reaction of the formula-CIX bicyclo hexene with an aldehyde of the formula

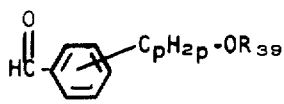 CXIX wherein $C_pH_{2p}$ represents a valence bond or alkylene of one to 4 carbon atoms, inclusive, with one or 2 carbon atoms in the chain between the phenylene ring and —O—, and wherein $R_{39}$ is carboxyacyl of the formula

wherein $R_{40}$ is hydrogen, alkyl of one to 19 carbon atoms, inclusive, or aralkyl of 7 to 12 carbon atoms, inclusive, wherein alkyl or aralkyl are substituted with zero to 3 halo atoms.

The formula-CXIX aldehydes are available or readily prepared by methods known in the art. Examples of such compounds within the scope of formula CXIX are:

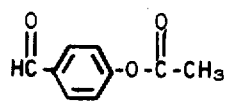

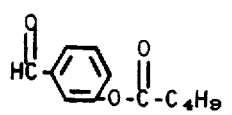

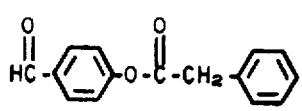

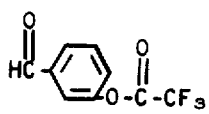

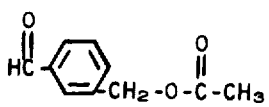

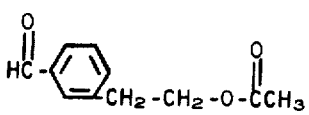

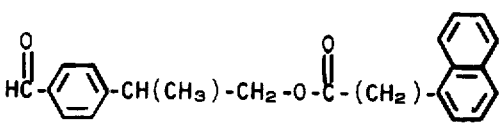

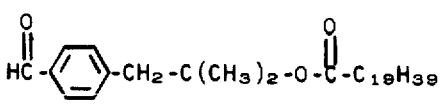

The formation of oxetane CX is accomplished by photolysis of a mixture of the bicyclo hexene and the aldehyde in a solvent. The bicyclo hexene is preferably used in excess over the molar equivalent, for example 2 to 4 times the theoretical equivalent amount. The solvent is a photochemically inert organic liquid, for example liquid hydrocarbons, including benzene or hexane, 1,4-dioxane, and diethyl ether. The reaction is conveniently done at ambient conditions, for example 25° C., but may be done over a wide range of temperature, from about −78°C. to the boiling point of the solvent. The irradiation is done with mercury vapor lamps of the low or medium pressure type, for example those peaking at 3500 A. Such sources are available from The Southern New England Ultraviolet Co., Middletown, Conn. Alternatively, those lamps which emit a broad spectrum of wavelengths and which may be filtered to transmit only light of λ~3000–3700 A may also be used. For a review of photolysis see D. R. Arnold in "Advances in Photochemistry," Vol. 6, W. A. Noyes et al., Wiley-Interscience, New York, 1968, pp. 301–423.

In step (b) the cleavage of the oxetane ring to yield the formula-CXI compounds is accomplished with an alkali metal in the presence of a primary amine or alcohol. Preferred is lithium in ethylamine, or sodium in ethyl alcohol. See L. J. Altman et al., Synthesis 129 (1974). The cleavage transformation may also be accomplished by catalytic hydrogenation over an inert metal catalyst, e.g. Pd on carbon, in ethyl acetate or ethanol.

In step (c) the formula CXI diol is prepared for step (d) by preferably blocking the two hydroxyl groups with carboxyacyl groups within the scope of $R_{39}$, i.e.

as defined above. For example, the diol is treated with an acid anhydride such as acetic anhydride, or with an acyl halide in a tertiary amine. Expecially preferred is pivaloyl chloride in pyridine.

Other carboxyacylating agents useful for this transformation are known in the art or readily obtainable by methods known in the art, and include carboxyacyl halides, preferably chlorides, bromides, or fluorides, i.e. $R_{40}C(O)Cl$, $R_{40}C(O)Br$, or $R_{40}C(O)F$, and carboxyacid anhydrides, $(R_{40}C—)_2O$, wherein $R_{40}$ is as defined above. The preferred reagent is an acid anhydride. Examples of acid anhydrides useful for this purpose are acetic anhydride, propionic anhydride, butyric anhydride, pentanoic anhydride, nonanoic anhydride, trideconoic anhydride, steric anhydride, (mono, di or tri) chloroacetic anhydride, 3-chlorovaleric anhydride, 3-(2-bromoethyl)-4,8-dimethylnonanoic anhydride, cyclopropaneacetic anhydride, 3-cycloheptanepropionic anhydride, 13-cyclopentanetridecanoic anhydride, phenylacetic anhydride, (2 or 3)-phenylpropionic anhydride, 13-phenyltridecanoic anhydride, phenoxyacetic anhydride, benzoic anhydride, (o, m, or p)-bromobenzoic anhydride, 2,4 (or 3,4)-dichlorobenzoic anhydride, p-trifluoromethylbenzoic anhydride, 2-chloro-3-nitrobenzoic anhydride, (o, m, or p)-nitrobenzoic anhydride, (o, m, or p)-toluic anhydride, 4-methyl-3-nitrobenzoic anhydride, 4-octylbenzoic anhydride, (2,3, or 4)-biphenylcarboxylic anhydride, 3-chloro-4-biphenylcarboxylic anhydride, 5-isopropyl-6-nitro-3-biphenylcarboxylic anhydride, and (1 or 2)-naphthoic anhydride. The choice of anhydride depends upon the identity of $R_{40}$ in the final acylated product, for example when $R_{40}$ is to be methyl, acetic anhydride is used; when $R_{40}$ is to be 2-chlorobutyl, 3-chlorovaleric anhydride is used.

When $R_{40}$ is hydrogen,

is formyl. Formylation is carried out by procedures known in the art, for example, by reaction of the hydroxy compound with the mixed anhydride of acetic and formic acids or with formylimidazole. See, for example, Fieser et al., Reagents for Organic Synthesis, John Wiley and Sons, Inc., pp. 4 and 407 (1967) and references cited therein. Alternatively, the formula CXI diol is reacted with two equivalents of sodium hydride and then with excess ethyl formate.

In formula CXII, $R_{43}$ may also represent a blocking group including benzoyl, substituted benzoyl, monoesterified phthaloyl and substituted naphthoyl. For introducing those blocking groups, methods known in the art are used. Thus, an aromatic acid of the formula $R_{39}OH$, wherein $R_{39}$ is as defined above, for example benzoic acid, is reacted with the formula-CXI compound in the presence of a dehydrating agent, e.g. sulfuric acid, zinc chloride, or phosphoryl chloride; or an anhydride of the aromatic acid of the formula $(R_{39})_2O$, for example benzoic anhydride, is used.

Preferably, however, an acyl halide, e.g. $R_{39}Cl$, for example benzoyl chloride, is reacted with the formula-CXI compound in the presence of a tertiary amine such as pyridine, triethylamine, and the like. The reaction is carried out under a variety of conditions using procedures generally known in the art. Generally, mild conditions are employed, e.g. 20°–60° C., contacting the reactants in a liquid medium, e.g. excess pyridine or an inert solvent such as benzene, toluene or chloroform. The acylating agent is used either in stoichiometric amount or in excess.

As examples of reagents providing $R_{39}$ for the purposes of this invention, the following are available as acids ($R_{39}OH$), anhydrides (($R_{39})_2O$), or acyl chlorides ($R_{39}Cl$): benzoyl; substituted benzoyl, e.g. (2-, 3-, or 4-)methylbenzoyl, (2-, 3-, or 4-)ethylbenzoyl, (2-, 3-, or 4-)isopropylbenzoyl, (2-, 3-, or 4-)tert-butylbenzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-, 3-, or 4-(toluyl, 2-, 3-, or 4-phenethylbenzoyl, 2-, 3-, or 4-nitrobenzoyl, (2,4-, 2,5-, or 3,5-)dinitrobenzoyl, 4,5-dimethyl-2-nitrobenzoyl, 2-nitro-6-phenethylbenzoyl, 3-nitro-2-phenethylbenzoyl; mono-esterified phthaloyl, e.g.

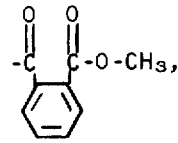

isophthaloyl, e.g.

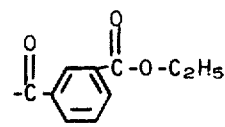

or terephthaloyl, e.g.

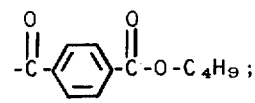

(1- or 2-)naphthoyl; and substituted naphthoyl, e.g. (2-, 3-, 4-, 5-, 6-, or 7-)methyl-1-naphthoyl, (2-or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, 8-benzyl-1-naphthoyl, (3-, 4-, 5-, or 8-)nitro-1-naphthoyl, 4,5-dinitro-1-naphthoyl, (3-, 4-, 6-, 7- or 8)-methyl-1-naphthoyl, 4-ethyl-2-naphthoyl, and (5- or 8-)-nitro-2-naphthoyl. There may be employed, therefore, benzoyl chloride, 4-nitrobenzoyl chloride, 3,5-dinitrobenzoyl chloride, and the like, i.e. $R_{39}Cl$ compounds corresponding to the above $R_{39}$ groups. If the acyl chloride is not available, it is made from the corresponding acid and phosphorus pentachloride as is known in the art.

In step (d), the formula -CXII acetal is converted to aldehyde CXIII by acid hydrolysis, known in the art, using dilute mineral acids, acetic or formic acids, and the like. Solvents such as acetone, dioxane, and tetrahydrofuran are used.

For steps (e) through (h) it is optional whether $R_{42}$ be hydrogen or a "blocking group" as defined below. For efficient utilization of the Wittig reagent it is preferred that $R_{42}$ be a blocking group. If the formula-CXII compound is used wherein $R_{43}$ is hydrogen, the formula-CXIII intermediates will have hydrogen at $R_{42}$. If $R_{42}$ is to be a blocking group, that may be readily provided prior to step (e) by reaction with suitable reagents as discussed below.

The blocking group, $R_{41}$, is any group which replaces hydrogen of the hydroxyl groups, which is not attacked by nor is reactive to the reagents used in the respective transformations to the extent that the hydroxyl group is, and which is subsequently replaceable by hydrogen at a later stage in the preparation of the prostaglandin-like products.

Several blocking groups are known in the art, e.g. tetrahydropyranyl, acetyl, and p-phenylbenzoyl (see Corey et al., J. Am. Chem. Soc. 93, 1491 (1971)).

Those which have been found useful include (a) carboxyacyl within the scope of $R_{39}$ above, i.e. acetyl, and also benzoyl, naphthoyl, and the like; (b) tetrahydropyranyl; (c) tetrahydrofuranyl; (d) a group of the formula

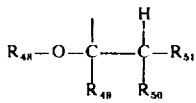

wherein $R_{48}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{49}$ and $R_{50}$ are the same or different, being hydrogen, alkyl of one to 4 carbon atoms, inclusive, phenyl or phenyl substituted with one, 2, or 3 alkyl of one to 4 carbon atoms, inclusive, or, when $R_{49}$ and $R_{50}$ are taken together, —(CH$_2$)$_u$— or —(CH$_2$)$_v$—O—(CH$_2$)$_w$—wherein $u$ is 3, 4, or 5, $v$ is one, 2, or 3, and $w$ is one, 2, or 3 with the proviso that $v$ plus $w$ is 2, 3, or 4, and wherein $R_{51}$ is hydrogen or phenyl; or (e) —Si(A)$_3$ wherein A is alkyl of one to four carbon atoms, inclusive, phenyl, phenyl substituted with one or 2 fluoro, chloro, or alkyl of one to four carbon atoms, inclusive, or aralkyl of 7 to 12 carbon atoms, inclusive.

In replacing the hydrogen atoms of the hydroxyl groups with a carboxyacyl blocking group, methods known in the art are used. The reagents and conditions are discussed above for $R_{43}$ on compound CXII.

When the blocking group is tetrahydropyranyl or tetrahydrofuranyl, the appropriate reagent, e.g. 2,3-dihydropyran or 2,3-dihydrofuran, is used in an inert solvent such as dichloromethane, in the presence of an acid condensing agent such as p-toluenesulfonic acid or pyridine hydrochloride. The reagent is used in slight excess, preferably 1.0 to 1.2 times theory. The reaction is carried out at about 20°–50° C.

When the blocking group is of the formula

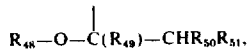

as defined above, the appropriate reagent is a vinyl ether, e.g. isobutyl vinyl ether or any vinyl ether of the formula $R_{48}$—O—C($R_{49}$)=C$R_{50}R_{51}$ wherein $R_{48}$, $R_{49}$, $R_{50}$, and $R_{51}$ are as defined above; or an unsaturated cyclic or heterocyclic compound, e.g. 1-cyclohex-1-yl methyl ether

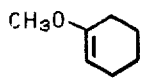

or 5,6-dihydro-4-methoxy-2H-pyran

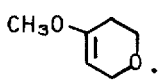

See C. B. Reese et al., J. Am. Chem. Soc. 89, 3366 (1967). The reaction conditions for such vinyl ethers and unsaturates are similar to those for dihydropyran above.

When the blocking group is silyl of the formula —Si(A)$_3$, the formula-CXIII compound is transformed to a silyl derivative of formula CXIII by procedures known in the art. See, for example, Pierce, "Silylation or Organic Compounds," Pierce Chemical Co., Rockford, Ill. (1968). The necessary silylating agents for these transformations are known in the art or are prepared by methods known in the art. See, for example, Post "Silicones and Other Organic Silicon Compounds," Reinhold Publishing Corp., New York, N.Y. (1949). These reagents are used in the presence of a tertiary base such as pyridine at temperatures in the range of about 0° to +50° C. Examples of trisubstituted mono-chlorosilanes suitable for this purpose include chlorotrimethylsilane, chlorotriisobutylsilane, chlorotriphenylsilane, chlorotris(p-chlorophenyl)silane, chlorotri-m-tolylsilane, and tribenzylchlorosilane. Alternately, a chlorosilane is used with a corresponding disilazane. Examples of other silylating agents suitable for forming the formula-CXIII intermediates include pentamethylsilylamine, pentaethylsilylamine, N-trimethylsilydiethylamine, 1,1,1-triethyl-N,N-dimethylsilylamine, N,N-diisopropyl-1,1,1,-trimethylsilylamine, 1,1,1-tributyl-N,N-dimethylsilylamine N,N-dibutyl-1,1,1-trimethylsilylamine, 1-isobutyl-N,N,1,1-tetramethylsilylamine, N-benzyl-N-ethyl-1,1,1-trimethylsilylamine, N,N,1,1-tetramethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilylamine, and 1-methyl-N,N,1,1-tetraphenylsilylamine.

In step (e) the aldehyde group is transformed by the Wittig reaction to a moiety of the formula —CH=CR$_2$G. For this purpose a phosphonium salt prepared from an organic chloride or bromide of the formula

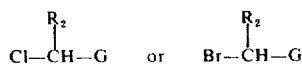

is employed, wherein G and $R_2$ are as defined above. These organic chlorides or bromides are known in the art or are readily prepared by methods known in the art. See for example the above-identified German Offenlegungsschrift No. 2,209,990. As to the Wittig reaction, see, for example, U.S. Pat. No. 3,776,941 and references cited therein.

In step (f) compound CXV is obtained by deblocking if necessary. When $C_pH_{2p}$ is a valence bond, and $R_{42}$ is a hindered carboxyacyl, e.g.

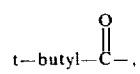

$R_{41}$ on the phenolic hydroxy is selectively replaced with hydrogen by hydrolysis with sodium or potassium hydroxide in ethanol-water. Instead of ethanol, other water-miscible solvents may be substituted, for example 1,4-dioxane, tetrahydrofuran, or 1,2-dimethoxyethane. The selective hydrolysis is preferably carried out at −15° to 25° C. Higher temperatures may be used but with some decrease in selectivity.

Total hydrolysis of $R_{42}$ blocking groups on compound CXIV is accomplished, when $R_{42}$ is carboxyacyl, with an alkali alkoxide in an alcoholic solvent, preferably sodium methoxide in methanol at a temperature from 25° C. to reflux. When $R_{42}$ is tetrahydropyranyl, aqueous acid, e.g. dilute acetic acid, is used at 25° to 50° C. When $R_{42}$ is trialkylsilyl, either aqueous acid or base are used at 25° to 50° C.

Continuing with Chart L, in step (g) a Williamson synthesis is employed to obtain compound CXVI. The formula-CXV alcohol or phenol is condensed with a haloacetate within the scope of $Hal-CH_2-COOR_1$ wherein Hal is chloro, bromo, or iodo and $R_1$ is as defined above. Normally the reaction is done in the presence of a base such as n-butyllithium, phenyllithium, triphenylmethyllithium, sodium hydride, potassium t-butoxide, sodium hydroxide, or potassium hydroxide.

The transformation from compound CXVI to product CXVIII may be accomplished by any of several routes known in the art. See U.S. Pat. No. 3,711,515. Thus, by step (h), the alkenene CXVI is hydroxylated to glycol CXVII. For this purpose osmium tetroxide is a suitable reagent, for example in conjunction with N-methylmorpholine oxide-hydrogen peroxide complex (see Fieser et al., "Reagents for Organic Synthesis," p. 690, John Wiley and Sons, Inc., New York (1967)). Thereafter, several methods are available for obtaining the formula-CXVIII product. In one method the glycol is converted to a bis(alkanesulfonic acid) ester and subsequently hydrolyzed to CXVIII by methods known in the art (see, for example German Offenlegungsschrift No. 1,937,676, Derwent Farmdoc No. 6862R). Another method is by way of a diformate by formolysis of the glycol (see U.S. Pat. No. 3,711,515).

Still another method is by way of a cyclic ortho ester. For this purpose, glycol CXVII is reacted with an ortho ester of the formula

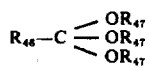

wherein $R_{46}$ is hydrogen, alkyl of one to 19 carbon atoms, inclusive, or aralkyl of 7 to 12 carbon atoms, inclusive, substituted with zero to 3 halo atoms; and $R_{47}$ is methyl or ethyl. There is then formed a cyclic ortho ester of the formula

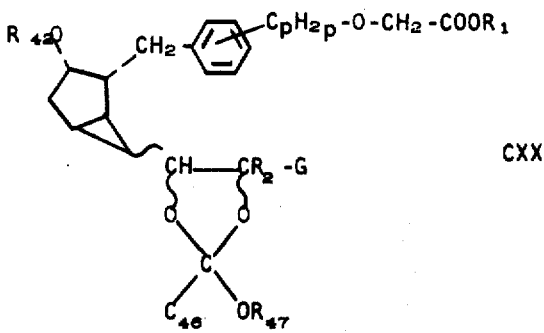

CXX wherein $C_pH_{2p}$, G, $R_1$, $R_2$, $R_{42}$, $R_{46}$, $R_{47}$, and ~ are as defined above. The reaction goes smoothly in a temperature range of $-50°C.$ to $+100°C.$, although for convenience $0°C.$ to $+50°C.$ is generally preferred. From 1.5 to 10 molar equivalents of the ortho ester are employed, together with an acid catalyst. The amount of the catalyst is usually a small fraction of the weight of the glycol, say 1%, and typical catalysts include pyridine hydrochloride, formic acid, hydrogen chloride, p-toluenesulfonic acid, trichloroacetic acid, or trifluoroacetic acid. The reaction is preferably run in a solvent, for example benzene, dichloromethane, ethyl acetate, or diethyl ether. It is generally completed within a few minutes and is conveniently followed by TLC (thin layer chromatography on basic silica gel plates).

The ortho ester reagents are known in the art or readily available by methods known in the art. See for example S. M. McElvain et al., J. Am. Chem. Soc. 64, 1925 (1942), starting with an appropriate nitrile. Examples of useful ortho esters include:
trimethyl orthoformate,
triethyl orthoacetate,
triethyl orthopropionate,
trimethyl orthobutyrate,
triethyl orthovalerate,
trimethyl orthooctanoate,
trimethyl orthophenylacetate, and
trimethyl ortho (2,4-dichlorophenyl)acetate.

Preferred are those ortho esters wherein $R_{46}$ is alkyl of one to 7 carbon atoms; especially preferred are those wherein $R_{46}$ is alkyl of one to 4.

Next, the cyclic orthoester CXX is reacted with anhydrous formic acid to yield a diol diester of the formula

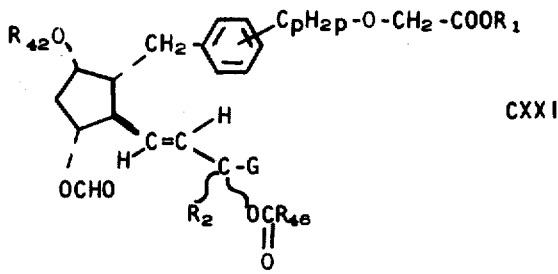

CXXI wherein $C_pH_{2p}$, G, $R_1$, $R_2$, $R_{42}$, $R_{46}$, and ~ are as defined above.

By "anhydrous formic acid" is meant that it contains not more than 0.5% water. The reaction is run with an excess of formic acid, which may itself serve as the solvent for the reaction. Solvents may be present, for example dichloromethane, benzene, or diethyl ether, usually not over 20% by volume of the formic acid. There may also be present organic acid anhydrides, for example acetic anhydride, or alkyl orthoesters, for example trimethyl orthoformate, which are useful as drying agents for the formic acid. Although the reaction proceeds over a wide range of temperatures, it is conveniently run at about 20°-30° C. and is usually completed within about 10 minutes.

Finally, the diol diester CXXI is converted to product CXVIII by methods known in the art, for example by hydrolysis in the presence of a base in an alcoholic medium. Examples of the base are sodium or potassium carbonate or sodium or potassium alkoxides including methoxides or ethoxides. The reaction is conveniently run in an excess of the solvolysis reagent, for example methanol or ethanol. The temperature range is from $-50°$ C. to 100° C. The time for completion of the reaction varies with the nature of $R_{46}$ and the base, proceeding in the case of alkali carbonates in a few minutes when $R_{46}$ is hydrogen but taking up to several hours when $R_{46}$ is ethyl, for example.

When the solvolysis proceeds too long or when conditions are too severe, ester groups at $R_1$ may be removed. They are, however, readily replaced by methods known in the art. For example, the alkyl, cycloalkyl, and aralkyl esters are prepared by interaction of the formula-CXVIII acids with the appropriate diazohydrocarbon. For example, when diazomethane is used, the methyl esters are produced. Similar use of diazoethane, diazobutane, 1-diazo-2-ethylhexane, diazocyclohexane, and phenyldiazomethane, for example, gives the ethyl, butyl, 2-ethylhexyl, cyclohexyl, and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example Organic Reactions, John Wiley & Sons, Inc., New York, N.Y., Vol. 8, pp. 389–394 (1954).

An alternative method for esterification of the carboxyl moiety comprises transformation of the free acid to the corresponding silver salt, followed by interaction of that salt with an alkyl iodide. Examples of suitable iodides are methyl iodide, ethyl iodide, butyl iodide, isobutyl iodide, tere-butyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The phenyl and substituted phenyl esters are prepared by silylating the acid to protect the hydroxy groups, for example, replacing each —OH with —O—Si—(CH$_3$)$_3$. Doing that may also change —COOH to —COO—Si—(CH$_3$)$_3$. A brief treatment of the silylated compound with water will change —COO—Si—(CH$_3$)$_3$ back to —COOH. Procedures for this silylation are known in the art. Then, treatment of the silylated compound with oxalyl chloride gives the acid chloride which is reacted with phenol or the appropriate substituted phenol to give a silylated phenyl or substituted phenyl ester. Then the silyl groups, e.g., —O—Si—(CH$_3$)$_3$ are changed back to —OH by treatment with dilute acetic acid. Procedures for these transformations are known in the art.

Referring to Chart M, there are shown process steps by which the formula-CIX bicyclo hexene is transformed first to an oxetane CXXII with a fully developed side chain.

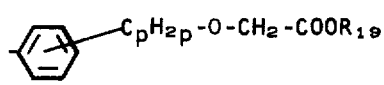

CHART M

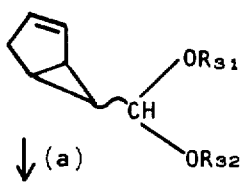
CIX

↓ (a)

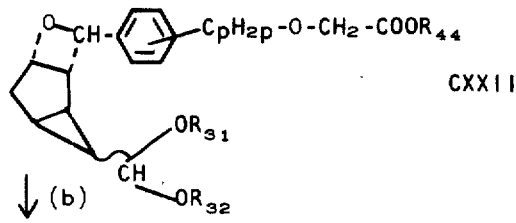
CXXII

↓ (b)

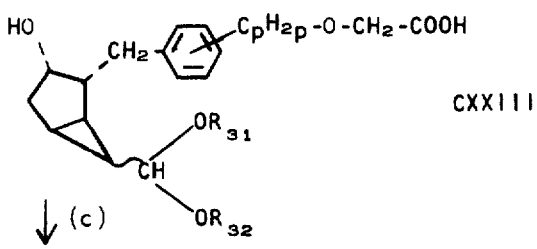
CXXIII

↓ (c)

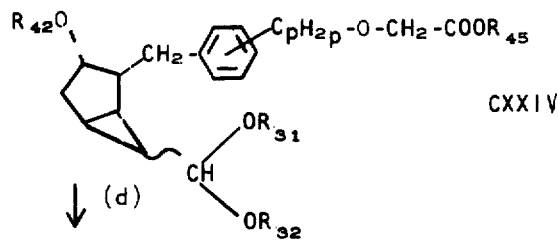
CXXIV

↓ (d)

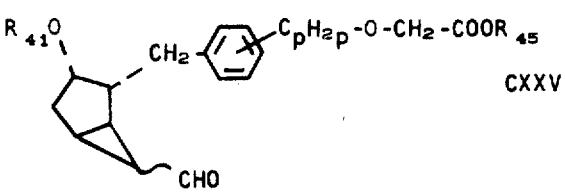
CXXV

↓ (e) continued

CHART M (continued)

↓(e)

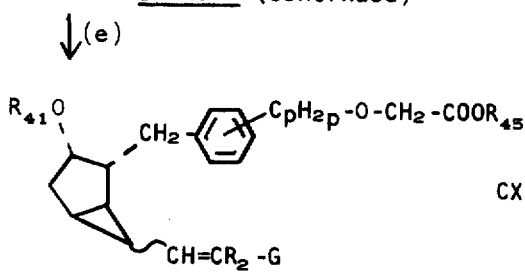

CXXVI

↓(f)

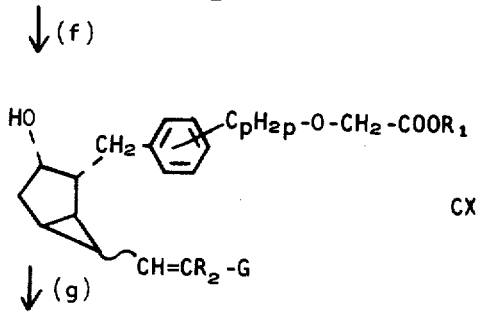

CXXVII

↓(g)

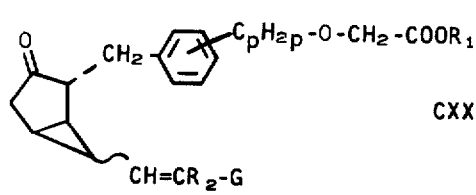

CXXVIII

↓(h)

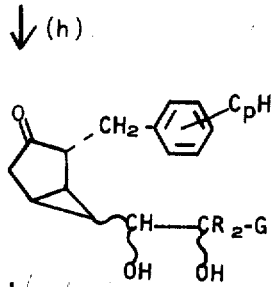

↓ via several steps

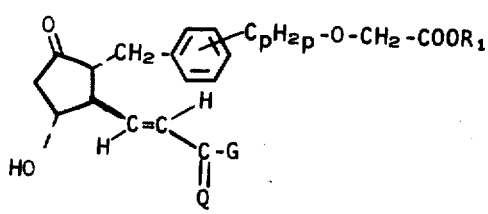

CXXX

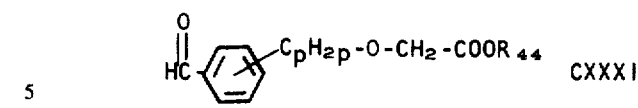

CXXXI wherein $C_pH_{2p}$ and $R_{44}$ are as defined above. Such aldehydes are available or readily prepared by methods known in the art. Examples of such compounds include:

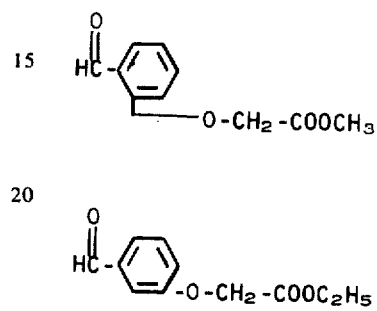

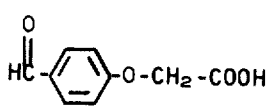

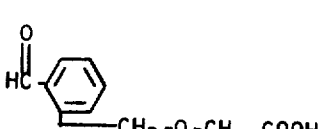

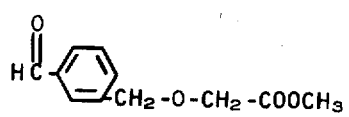

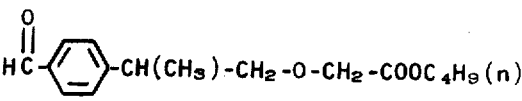

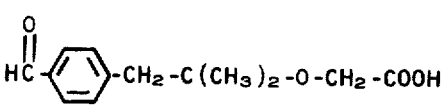

and ultimately to a PGE analog. In Chart M, $R_{44}$ is hydrogen or alkyl of one to 4 carbon atoms, inclusive, and $R_{45}$ is hydrogen, alkyl of one to 4 carbon atoms, inclusive, or silyl of the formula $(A)_3Si-$ wherein A is as defined herein above.

In step (a) of Chart M, there is employed an aldehyde of the formula

The conditions for step (a) of Chart M are essentially the same as for step (a) of Chart L. Thereafter, step (b) for cleavage of the oxetane ring, steps (c) and (d) leading to the formula-CXXV aldehyde, and the Wittig reaction of step (e) are similar to and employ the same conditions as the corresponding steps of Chart L discussed above.

Referring to step (g) of Chart M, the hydroxyl on the cyclopentane ring at the C-9 position is oxidized to an oxo group.

Oxidation reagents useful for this transformation are known in the art. A useful reagent for this purpose is the Jones reagent, i.e., acidified chromic acid. See J. Chem. Soc. 39 (1946). A slight excess beyond the amount necessary to oxidize the C-9 secondary hydroxy groups of the formula-CXXVII reactant is used. Acetone is a suitable diluent for this purpose. Reaction temperatures at least as low as about 0° C. should be used. Preferred reaction temperatures are in the range 0° to −50° C. An especially useful reagent for this purpose is the Collins reagent, i.e. chromium trioxide in pyridine. See J. C. Collins et al., Tetrahedron Lett., 3363 (1968). Dichloromethane is a suitable diluent for this purpose. Reaction temperatures of below 30° C. should be used. Preferred reaction temperatures are in the range 0° to +30° C. The oxidation proceeds rapidly and is usually complete in about 5 to 20 minutes.

Examples of other oxidation reagents useful for this transformation are silver carbonate on Celite (Chem. Commun. 1102 (1969)), mixtures of chromium trioxide and pyridine (J. Am. Chem. Soc. 75, 422 (1953), and Tetrahedron, 18, 1351 (1962)), t-butylchromate in pyridine (Biochem. J. 84, 195 (1962)), mixtures of sulfur trioxide in pyridine and dimethylsulfoxide (J. Am. Chem. Soc. 89, 5505 (1967)), and mixtures of dicyclohexylcarbodiimide and dimethyl sulfoxide (J. Am. Chem. Soc. 87, 5661 (1965)).

Step (h) of Chart M and subsequent steps by which the product CXXX is obtained are similar to and employ the same conditions as the corresponding steps of Chart L discussed above.

Referring next to Chart N the process steps are shown whereby aldehyde CXIII of Chart L is transformed to a 17,18-tetradehydro-PG analog CXXXVI and a 17,18-didehydro-PG analog CXXXVII.

In step (a) of Chart N, a Wittig reagent is employed which is prepared from a phosphonium salt of a haloalkyne of the formula

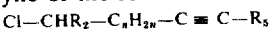

or

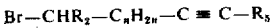

wherein $C_nH_{2n}$, $R_2$, and $R_5$ are as defined above. See, for example, U. Axen et al., Chem. Comm. 1969, 303, and ibid. 1970, 602.

Thereafter, in steps (b) to (d) and subsequent steps yielding the 17,18-tetradehydro compound CXXVI, the reagents

CHART N

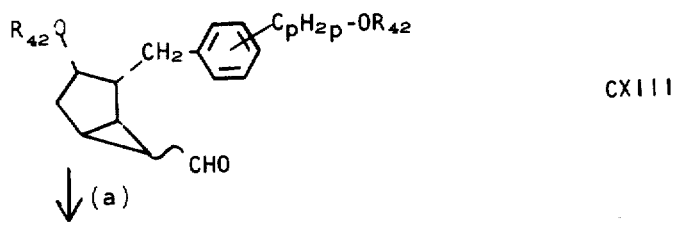

CXIII

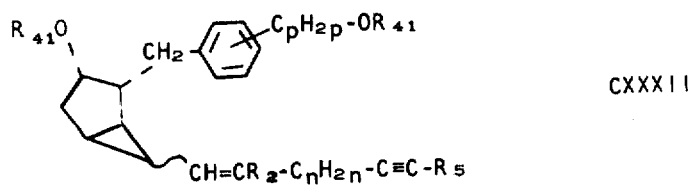

CXXXII

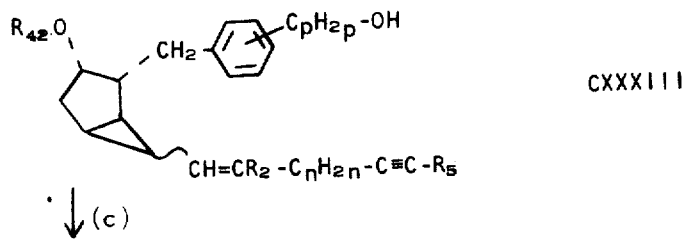

CXXXIII

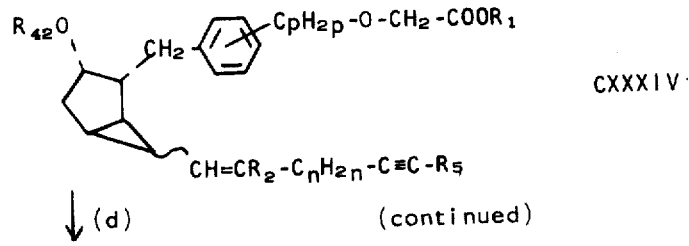

CXXXIV (continued)

CHART N (continued)

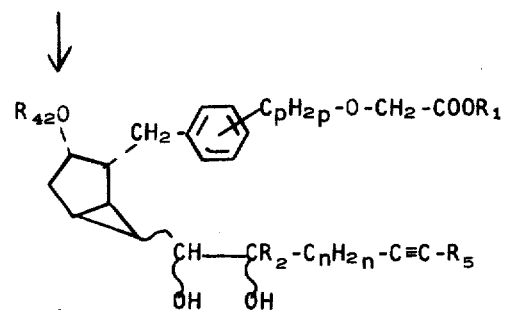

CXXXV via several steps

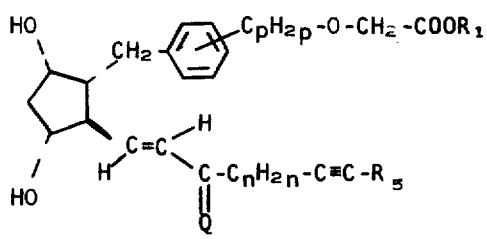

CXXXVI

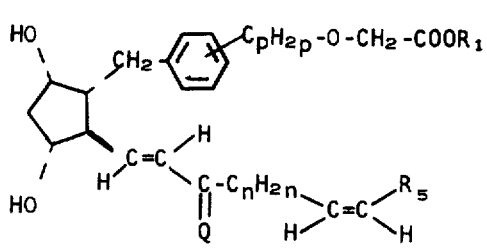

CXXXVII and conditions are similar to those employed for the corresponding reactions shown in Chart L.

Transformation of CXXXVI to the formula-CXXXVII compounds is accomplished by hydrogenation of CXXXVI using a catalyst which catalyzes hydrogenation of —C≡C— only to cis—CH=CH—, as known in the art. See, for example, Fieser et al., "Reagents for Organic Syntheses," pp. 566–567, John Wiley and Sons, Inc., New York (1967). Preferred is Lindlar catalyst in the presence of quinoline, see Axen, references cited.

The intermediates of Charts L, M, and N, including those compounds represented by formulas CX, CXI, CXII, CXIII, CXIV, CXV, CXVI, CXVII, CXXII, CXXIII, CXXIV, CXXV, CXXVI, CXXVII, CXXVIII, CXXIX, CXXXII, CXXXIII, CXXXIV, CXXXV, and CXXXVI are frequently not isolated but used directly for a subsequent process step. When they are isolated, they are purified by methods known in the art, for example partition extraction, fractional crystallization, and, preferably, silica gel column chromatography.

The products represented by formulas CXVIII, CXXX, and CXXXVII obtained from these intermediates are often a mixture of 15-$\alpha$ and 15-$\beta$ isomers.

These are separated by methods known in the art, for example, by chromatography on neutral silica gel. In some instances, particularly where $R_2$ is alkyl, the lower alkyl esters are more readily separated than are the corresponding acids. In those cases wherein $R_1$ is hydrogen, it is advantageous to esterify the mixture of acids, as with diazomethane, to form the methyl esters, separate the two epimers, and then, if desired, replace the carboxyl methyl with hydrogen by methods known in the art.

When an optically active intermediate or starting material is employed, subsequent steps yield optically active intermediates or products. That optical isomer of bicyclo hexene CIX is used which will yield product CXVIII for example, in the configuration corresponding to that of the naturally occurring prostaglandins. When the racemic form of the intermediate or starting material is employed, the subsequent intermediates or products are obtained in their racemic form.

DESCRIPTION OF THE PREFERRED EMBODIMENTS

The invention can be more fully understood by the following examples and preparations:

All temperatures are in degrees centigrade.

Infrared absorption spectra are recorded on a Perkin-Elmer Model 421 infrared spectrophotometer. Except when specified otherwise, undiluted (neat) samples are used.

Ultraviolet spectra are recorded on a Cary Model 15 spectrophotometer.

NMR spectra are recorded on a Varian A-60, A-60D, or T-60 spectrophotometer using deuterochloroform solutions with tetramethylsilane as an internal standard (downfield).

Mass spectra are recorded on a CEC Model 110B Double Focusing High Resolution Mass Spectrometer or an LKB Model 9,000 Gas Chromatograph-Mass Spectrometer (ionization voltage 70 ev).

Circular dichroism curves are recorded on a Cary 60 recording spectropolarimeter.

Specific rotations are determined for solutions of a compound in the specified solvent with a Perkin-Elmer Model 141 Automatic Polarimeter.

The collection of chromatographic eluate fractions starts when the eluant front reaches the bottom of the column.

"Brine," herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

"Skellysolve-B" refers to mixed isomeric hexanes.

Silica gel chromatography, as used herein, is understood to include elution, collection of fractions, and combination of those fractions shown by TLC (thin layer chromatography) to contain the desired product free of starting material and impurities.

PREPARATION 1 dl-Endo-6-(1-heptenyl)-3-(1-pyrrolidyl)-bicyclo[3.1.0]hex-2-ene.

A solution of formula-XLIII endo-6-(cis- and trans-1-heptenyl)bicyclo[3.1.0]hexan-3-one (see Example 29 of West Germany Offenlegungsschrift No. 1,937,912, cited above) (15 g.), 25 ml. of pyrrolidine, and 200 ml. of benzene is heated under reflux while removing the water formed by distillation. After 2 hrs. the benzene is replaced by 50 ml. of toluene which is then removed in vacuo to give the title compound. This material gives an infrared spectrum having absorption attributable to the enamine double bond at 1610 cm$^{-1}$ and free of carbonyl absorption.

PREPARATION 2

Methyl m-(Chloromethyl)phenoxyacetate (Formula LIII: $C_gH_{2g}$ and $C_pH_{2p}$ are valence bonds in meta relationship, $C_qH_{2q}$ is methylene, Hal is chloro, $R_{26}$ is hydrogen, and $R_{10}$ is methyl).

a. m-Formylphenoxyacetic Acid. To a solution of m-hydroxybenzaldehyde (48.8 g.) and sodium hydroxide (16.16 g.) in 500 ml. of water is added a solution prepared from chloroacetic acid (75 g.) and sodium hydroxide (32 g.) in 100 ml. of water. The mixture is heated under reflux for 2 hrs., cooled, and the pH is adjusted to pH 1 or 2. The mixture is extracted with dichloromethane-ether and the extract is dried and concentrated. The solid is taken up in saturated aqueous sodium bicarbonate, extracted with ether and the aqueous phase is made acidic. The aqueous phase is extracted with dichloromethane. The organic layer is concentrated and the residue is recrystallized from water to give m-formylphenoxyacetic acid (34.0 g.) m.p. 114°–117°.

b. Methyl M-Formylphenoxyacetate. A solution of the product of step a (30.0 g.) in 400 ml. of diethyl ethertetrahydrofuran is treated with an excess of ethereal diazomethane generated from N-methyl-N'-nitro-N-nitro-soguanidine (32.5 g.) and 200 ml. of 30% potassium hydroxide. The organic extract is washed with 5% sodium hydroxide, dried and concentrated to give methyl m-formylphenoxyacetate (17 g.), as a light yellow oil.

c. Methyl m-(Hydroxymethyl)phenoxyacetate. A solution of the product of step b (30.0 g.) in 200 ml. of methanol, cooled in an ice bath to 0°, is treated with sodium borohydride (1.55 g.) in 30 ml. of cold water. After the addition, stirring is continued for 20 min., the methanol is removed, and 60 ml. of brine is added. The aqueous phase is extracted with ether and the ether solution is washed, first with 5% aqueous hydrochloric acid, then brine, and dried. Removal of the solvent yields methyl m-(hydroxymethyl)phenoxyacetate(27.0 g.).

d. Methyl m-(Chloromethyl)phenoxyacetate. To the product of step c (27.0 g.) is added 20 ml. of thionyl chloride with stirring. Following the addition, the reaction mixture is stirred at 25° for 30 min. and at reflux for 30 min. After cooling the reaction mixture, it is dissolved in ether and washed carefully with water, saturated aqueous sodium bicarbonte and brine. The organic layer is dried, concentrated and distilled to give the title compound (11.0 g.) b.p. 98°–110°/0.03 mm.

Following the procedures of Preparation 2, but replacing chloroacetic acid with 3-chloropropionic acid, there is obtained, successively, 3-(m-formylphenoxy)-propionic acid and its methyl ester, methyl 3-[m-(hydroxymethyl)phenoxy]-propionate, and the formula-LIII compound, methyl 3-[m-(chloromethyl)phenoxy]-propionate.

Alternatively, Michael addition of m-hydroxy benzaldehyde to methyl acrylate, with base catalysis, and reduction of the product with sodium borohydride gives methyl 3-[m-(hydroxymethyl)phenoxy]propionate.

PREPARATION 3

Ethyl o-(Bromomethyl)benzyloxyacetate (Formula LIII: $C_gH_{2g}$ is a valence bond, $C_pH_{2p}$ and $C_qH_{2q}$ are methylene, $C_gH_{2g}$ and $C_pH_{2p}$ are in ortho relationship, Hal is bromo, $R_{26}$ is hydrogen, and $R_{10}$ is ethyl).

To a mixture of α,α'-dibromo-o-xylene (100 g.), ethyl glycolate (47 g.), and dimethylformamide (500 ml.) is added with stirring over a 1-hour period at 0°–5° C., 18 g. of 57% sodium hydride. The mixture is stirred for 16 hrs. at about 25° C. and is then concentrated on a rotating evaporator at 40°–50° C. under vacuum. The residue is diluted with one liter of a mixture of isomeric hexanes (Skellysolve B) and diethyl ether (1:2 by volume) and the organic solution is washed successively with dilute hydrochloric acid, dilute potassium hydroxide solution, water, and brine, and is finally dried and concentrated. The residue is chromatographed on a column prepared by wet-packing 3 kg. of silica gel (Brinkman) with 6 l. of 15% ethyl acetate in Skellysolve B and 30 ml. of absolute ethanol. Gradient elution of the column with 16 l. of 15–35% ethyl acetate in Skellysolve B gives fractions of 400 ml. each of which are combined on the basis of thin layer chromatography (TLC). From fractions 18–27 there is obtained 35 g. of the title compound. This material has $\lambda_{max}$ in ethanol at 231 m$\mu$ ($\epsilon$ 7550) with shoulders at 272 ($\epsilon$ 700) and 278 m$\mu$ ($\epsilon$ 462). It has key absorptions in its NMR spectrum at about 7.3 (apparent singlet), 4.7 (singlet), 4.64 (singlet), 4.06 (singlet), 4.0–4.35 (quartet), and 1.1–1.34 (triplet) $\delta$. It has mass spectral peaks at 206, 199, 201, 185, and 183.

PREPARATION 4

Endo-6-(cis-4-phenyl-1-butenyl)-bicyclo-[3.1.0]hexan-3-one (Formula XLIII: G is

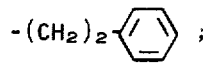

$R_3$ and $R_4$ are hydrogen; and ~ is endo).

a. There is first prepared (3-phenylpropyl)triphenylphosphonium bromide. A solution of 597.3 g. of 1-bromo-3-phenylpropane and 786 g. of triphenylphosphine in 1,500 ml. of toluene is heated at reflux under nitrogen for 16 hrs., then the mixture is cooled and the solid product is separated by filtration. The solid is then slurried with toluene in a Waring blender, separated by filtration, and dried for 18 hrs. at 70° C. under reduced pressure to give 1068 g. of (3-phenylpropyl)triphenylphosphonium bromide; m.p. 210.5°–211.5° C.

b. A suspension of 314 g. of the product of step a in 3 l. of benzene is stirred at room temperature (25° C.) under nitrogen, and 400 ml. of 1.6 M butyllithium in hexane is added over a 20 min. period. The mixture is heated at 35° C. for 30 minutes, then is cooled to −15° C. and a solution of 100 g. of endo-bicyclo[3.1.0]hexan-3-ol-6-carboxaldehyde 3-tetrahydropyranyl ether in 200 ml. of benzene is added over a 30-min. period. This mixture is heated at 70° C. for 2.5 hrs., cooled, and filtered. The filtrate is washed three times with water, dried over sodium sulfate, and concentrated to 170 g. of crude endo-6-(cis-4-phenyl-1-butenyl)-bicyclo[3.1.0]hexan-3-ol 3-tetrahydropyranyl ether.

A solution of 340 g. (two runs) of this crude endo-6-(cis-4-phenyl-1-butenyl)-bicyclo-[3.1.0]hexan-3-ol 3-tetrahydropyranyl ether and 20 g. of oxalic acid in 3600 ml. of methanol is heated at reflux for 3.5 hrs. The mixture is cooled and the methanol is evaporated under reduced pressure. The residue is mixed with dichloromethane, and the dichloromethane solution is washed with aqueous sodium bicarbonate, dried over sodium sulfate, and concentrated to 272 g. of the endo-6-(cis-4-phenyl-1-butenyl)bicyclo[3.1.0]-hexan-3-ol.

A solution of 93 g. of the above endo-6-(cis-4-phenyl-1-butenyl)bicyclo[3.1.0]hexan-3-ol in 2570 ml. of acetone is cooled to −5° C. and 160 ml. of Jones reagent (in the proportions 42 g. of chromic anhydride, 120 ml. of water, and 34 ml. of concentrated sulfuric acid) is added over a period of 30 min. while cooling to maintain a temperature of −5° C. The mixture is allowed to stand for 10 min. longer; then 100 ml. of isopropyl alcohol is added and the mixture is swirled for 5 min. The mixture is then diluted with 6 l. of water and extracted several times with dichloromethane. The organic layers are separated, washed with dilute hydrochloric acid, water, dilute aqueous sodium bicarbonate, and brine, then are dried over sodium sulfate, combined and concentrated to 83 g. of crude endo-6-(cis-4-phenyl-1-butenyl)-bicyclo[3.1.0]hexan-3-one.

Crude endo-6-(cis-4-phenyl-1-butenyl)-bicyclo[3.1.0]-hexan-3-one (162 g., two runs) is dissolved in isomeric hexanes (Skellysolve B) and chromatographed over 5 kg. of silica gel wet-packed with Skellysolve B, eluting successively with 11 l. of Skellysolve B, 62 l. of 2.5% ethyl acetate in Skellysolve B, and 32 l. of 5% ethyl acetate in Skellysolve B. The last 8 l. of the 2.5% ethyl acetate in Skellysolve B eluates and the 32 l. of 5% ethyl acetate in Skellysolve B eluates are combined and concentrated to 75.8 g. of the title compound; infrared absorption at 3000, 1750, 1610, 1500, 1455, 1405, 1265, 1150, 778, 750 and 702 cm$^{-1}$., N.M.R. peaks at 7.18 (singlet) and 4.75–6.0 (broad multiplet) $\delta$.

PREPARATION 5

Endo-6-(cis-5-phenyl-1-pentenyl)-bicyclo-[3.1.0]hexan-3-one. (Formula XLIII: G is

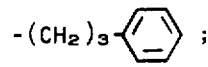

$R_2$ and $R_9$ are hydrogen; and ~ is endo).

a. There is first prepared (4-phenylbutyl)triphenylphosphonium bromide. A solution of 145 g. of 4-phenyl-1-bromobutane and 179 g. of triphenylphosphine in 350 ml. of toluene is heated at reflux under nitrogen for 16 hrs. The mixture is then cooled slowly and ether is added giving a precipitate of (4-phenylbutyl)triphenylphosphonium bromie which is washed throughly with benzene/ether and dried 18 hrs. at 50° C. under reduced pressure, 268 g., m.p. 139°–140° C.

b. A suspension of 242 g. of the product of step a in 2.3 l. of dry benzene at 25° C. is stirred and 300 ml. of 1.6 M butyllithium in hexane is added over a 15-min. period. The mixture is stirred at 30° C. for one hour, then is cooled to 10° C. and a solution of 75 g. of endobicyclo-[3.1.0]hexan-3-ol-6-carboxaldehyde 3-tetrahydropyranyl ether in 200 ml. of benzene is added over a 15-min. period. The mixture is heated at 65°–70° C. for 3 hours, cooled and filtered. The filtrate is washed with water and brine, dried over sodium sulfate, and concentrated under reduced pressure to give 117 g. of crude endo-6-(cis-5-phenyl-1-pentenyl)-bicyclo[3.1.0]hexan-3-ol tetrahydropyranyl ether showing a single spot, $R_f$ 0.75, on thin layer chromatography with silica gel plates developed with 20% ethyl acetate in cyclohexane.

A solution of 117 g. of the above crude endo-6-(cis-5-phenyl-1-pentenyl)-bicyclo[3.1.0]hexan-3-ol tetrahydropyranyl ether and 6 g. of oxalic acid in 2,500 ml. of methanol is heated under reflux for 2.5 hrs. The methanol is then removed by distillation under reduced pressure and the residue is diluted with water and extracted with dichloromethane. The dichloromethane extracts are combined, washed with aqueous sodium bicarbonate and brine, dried over sodium sulfate and concentrated under reduced pressure to give 95.7 g. of crude endo-6-(cis-5-phenyl-1-pentenyl)-bicyclo[3.1.0-]hexan-3-ol. The entire crude product is chromatographed over 1.5 kg. of silica gel wet-packed with Skellysolve B, eluting successively with 5 l. of Skelly-solve B, 4 l. of 2.5%, 6 l. of 5%, 9 l. of 7.5%, 12 l. of 10%, 8 l. of 15%, 10 l. of 20% and 10 l. of 30% ethyl acetate in Skellysolve B, taking 600 ml. fractions. The last fraction of 10% ethyl acetate in Skellysolve B, all the 15% and 20% ethyl acetate in Skellysolve B eluates, and the first 3 fractions of 30% ethyl acetate in Skellysolve B are concentrated to 60.5 g. of purified endo-6-(cis-5-phenyl-1-pentenyl)bicyclo[3.1.0]hexan-3-ol.

A solution of 60.5 g. of the above purified alcohol in 1,600 ml. of acetone is cooled to −10° C. and 103 ml. of Jones reagent is added dropwise. After addition is complete the mixture is stirred for 10 min. at 0° C. and 65 ml. of isopropyl alcohol is added. The mixture is poured into 8 l. of water and extracted several times with dichloromethane. The dichloromethane extracts are combined, washed with dilute hydrochloric acid, aqueous sodium bicarbonate and brine, dried over sodium sulfate and concentrated under reduced pressure to give 56 g. of crude endo-6-(cis-5-phenyl-1-pentenyl)bicyclo[3.1.0]hexan-3-one. The crude ketone is slurried in Skellysolve B and chromatographed over 2,300 g. of silica gel wet packed in Skellysolve B, eluting successively with 6 l. of Skellysolve B, 16 l. of 2.5% ethyl acetate in Skellysolve B, then gradient elution with 5 l. of 2.5% and 5 l. of 5% ethyl acetate in Skellysolve B and finally 16 l. of 5% ethyl acetate in Skellysolve B, taking 625 ml. fractions. The last fraction of the gradient eluates and the first 19 fractions of 5% ethyl acetate in Skellysolve B are concentrated to give 23.6 of the title compound; infrared absorption at 2980, 1745, 1600, 1490, 1450, 1260, 1145, 770, 750 and 702 cm$^{-1}$., N.M.R. peaks at 7.17 (singlet), 6.0–5.4 (multiplet), and 5.2–4.7 (broad multiplet) $\delta$.

PREPARATION 6

Endo-6-(1,2-dihydroxy-4-phenylbutyl)-bicyclo[3.1.0]hexan-3-one Acetonide (Formula XXXVI wherein G is

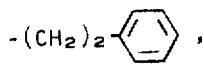

$R_2$ and $R_9$ are hydrogen, $R_{11}$ and $R_{12}$ are methyl, and ~ is endo).

a. There is first prepared the formula-LI dihydroxy compound. To a solution of endo-6-(cis-4-phenyl-1-butenyl)-bicyclo[3.1.0]hexan-3-one (10.0 g., Preparation 4) in about 100 ml. tetrahydrofuran is added, with stirring, a solution of potassium chlorate (10.0 g.) and osmium tetroxide (0.65 g.) in 250 ml. of water. The mixture is stirred vigorously for 5 hrs. at 50° C. Then, the cooled mixture is concentrated under reduced pressure. The residue is extracted repeatedly with dichloromethane, and the combined extracts are dried and concentrated to an oil. This oil is chromatographed on about 1000 g. of silica gel, and eluted successively with 3 l. of 10% ethyl acetate in a mixture of isomeric hexanes (Skellysolve B), with 5 l. of 25% ethyl acetate in Skellysolve B, and then with 50% ethyl acetate in Skellysolve B, collecting 500 ml. eluate fractions. Fractions 13-19 (50% ethyl acetate) are combined and evaporated to dryness to give dl-endo-6 (1,2-dihydroxy-4-phenylbutyl)-bicyclo[3.1.0]hexane-3-one (Formula LI).

b. A solution of the product of step a (about 8.0 g.) and 700 mg. of potassium bisulfate in 140 ml. of acetone is stirred at 25° C. for 64 hrs. Then, sodium carbonate monohydrate (710 mg.) is added, and the mixture is stirred 10 minutes. The acetone is evaporated at reduced pressure, and water is added. The aqueous solution is extracted repeatedly with dichloromethane, and the extracts are combined, washed with water, dried, and concentrated to about 9.3 g. of an oil. The oil is chromatographed on 400 g. of silica gel, being eluted with 2 l. of 10% ethyl acetate in Skellysolve B, and then with 4 l. of 15% ethyl acetate in Skellysolve B. The 15% ethyl acetate eluates are concentrated to about 7.4 g. of the formula-XXXVI compound, endo-6-(1,2-dihydroxy-4-phenylbutyl)-bicyclo[3.1.0]hexan-3-one acetonide.

PREPARATION 7

Methyl 9-Bromo-3-oxa-3,7-inter-m-phenylene-4,5,6-trinor-7-nonynoate. (Formula LIV: $C_jH_{2j}$ and $C_pH_{2p}$ are valence bonds in meta relationship, $C_qH_{2q}$ is methylene, Hal is bromo, $R_{26}$ is hydrogen and $R_{10}$ is methyl).

a. To a cold, stirred solution of m-vinylanisole (13.4 g.) in 40 ml. of diethyl ether is slowly added a solution of bromine (15.9 g.) in 60 ml. of diethyl ether. The ether solution is used directly in converting the product, m-(1,2-dibromoethyl)anisole to m-methoxyphenylacetylene by dehydrohalogenation (see T. H. Vaughn, J. Am. Chem. Soc. 56, 2064, 1934). The ether solution above is slowly added, with vigorous stirring, to a mixture of sodium amide prepared from sodium (4.6 g.) in about 200 ml. of liquid ammonia. When the reaction is complete, the volume is reduced about one-half, and an equal volume of water is cautiously added. A layer containing the product is separated, washed with dilute hydrochloric acid, dried, and distilled.

b. To a solution of the product of step a above in 250 ml. of dichloromethane, maintained at 0° C. under nitrogen, is added dropwise over about a 1-hour period with vigorous stirring a solution of about 15 ml. of boron tribromide in 200 ml. of dichloromethane. Cooling and stirring continue for one hour. When the reaction is complete as shown by TLC, there is added cautiously a solution of sodium carbonate in water to neutralize the mixture. Thereafter, the solution is saturated with sodium chloride (added as a solid), and the organic phase is separated and combined with additional ethyl acetate washings of the aqueous phase. The organic solutions are washed with brine, dried over sodium sulfate, and concentrated under reduced pressure to yield the acetylenic phenol.

c. To the product of step b (11.8 g.), is added gradually a solution of sodium ethoxide (prepared from sodium and absolute ethanol). Thereafter, ethylene chlorohydrin (8.0 g.) is added in small portions. When all has been added, the mixture is heated at reflux for about one hour or until completion, then filtered hot. The combined filtrate and ethanol washings are concentrated to remove alcohol, and the product distilled under reduced pressure.

To the hydroxyethyl ether (16.2 g.) as obtained above, cooled to 15°–20° C., is added 20 ml. of dihydropyran and 100 ml. of diethylether, and, with stirring, 1 ml. of anhydrous diethyl ether saturated with hydrogen chloride. After the exothermic reaction has diminished, the mixture is kept at 25° C. for 15 hours. The mixture is washed with aqueous sodium bicarbonate, water, and dried, then concentrated under reduced pressure to yield the tetrahydropyranyl ether.

d and e. To a solution of the product of step c (10 g.) in anhydrous tetrahydrofuran (180 ml.) at −78° C. under argon is added the equivalent molecular amount of n-butyllithium in hexane. The resulting solution is stirred at −78° C. for an additional 30 minutes. A suspension of dry paraformaldehyde (two equivalents)

in anhydrous tetrahydrofuran is added and the mixture warmed to room temperature over a 30-min. period. It is stirred an additional 1 hour and poured into brine, then extracted with ether, dried, and concentrated to yield the hydroxy compound.

f. The hydroxy compound of step e is converted to the bromo compound by first forming the mesyl derivative by reaction with methanesulfonyl chloride (4 ml.) in pyridine (80 ml.) at −20°C. The mixture is stirred 1 hour at −20° C., and then is poured into a stirred mixture of 3 normal hydrochloric acid (300 ml.) and ice water (500 ml.). This mixture is extracted with diethyl ether, the extract is washed with cold one normal hydrochloric acid and brine, then dried and concentrated. To a solution of the residue (mesyl derivative) in dry acetone (100 ml.) is added lithium bromide (5 g.) and the mixture stirred and heated at reflux one hour, then kept at 25° C. for 15 hours. The acetone is evaporated under reduced pressure, and the residue is extracted with diethyl ether. The extract is washed with water and brine, then dried and concentrated. The residue is chromatographed on silica gel, eluting with 10% ethyl acetate in Skellysolve B. Fractions shown by TLC to contain the product are combined and concentrated to give the formula-LX intermediate.

g. The product of step f above is converted to the corresponding carboxylic acid and its methyl ester as follows. The tetrahydropyranyloxy group is replaced by hydroxyl by contacting the product of f with a mixture of acetic acid/water/tetrahydrofuran (20/10/3) at 40° C. for 2 hours, thereafter removing solvents under reduced pressure.

The substituted glycol from above is oxidized to the acid in acetone solution, using a slight excess of Jones reagent (21 g. chromic anhydride/60 ml. water/17 ml. conc. sulfuric acid) while cooling to maintain a temperature of −5° to 0° C. After about 60 min., isopropyl alcohol is added, the mixture is stirred for 10 min., and then poured into ice water. The acid product is isolated by extraction with chloroform, drying over sodium sulfate, and concentration under reduced pressure.

The acid from above is converted to the methyl ester by reaction with diazomethane in diethyl ether at about 10°–25° C., followed by concentration to yield the desired title compound.

Following the procedures of Preparation 7, but replacing m-vinylanisole with methyl (o, m, or p-)vinylbenzyl ether, there are obtained, respectively, methyl 9-bromo-3-oxa-4,7-inter-o-phenylene-5,6-dinor-7-nonynoate, methyl 10-bromo-3-oxa-4,8-inter-m-phenylene-5,6,7-trinor-8-decynoate, and methyl 11-bromo-3-oxa-4,9-inter-p-phenylene-5,6,7,8-tetranor-9-undecynoate.

PREPARATION 8

Methyl 9-Bromo-3-oxa-3,7-inter-m-phenylene-4,5,6-trinor-cis-7-nonenoate (Formula LV: $C_jH_{2j}$ and $C_pH_{2p}$ are valence bonds in meta relationships. $C_qH_{2q}$ is methylene, Hal is bromo, $R_{26}$ is hydrogen and $R_{10}$ is methyl).

A solution of methyl 9-bromo-3-oxa-3,7-inter-m-phenylene-4,5,6-trinor-7-nonynoate (2.0 g., Preparation 7) in 10 ml. of pyridine is hydrogenated in the presence of a 5% palladium on barium sulfate catalyst (150 mg.) at 25° C. and one atmosphere. The resulting mixture is filtered and evaporated to about one-third the original volume. Four volumes of ethyl acetate is added, and the remaining pyridine is removed by addition of ice and one N hydrochloric acid. The ethyl acetate layer is separated, washed successively with one N hydrochloric acid and brine, dried, and evaporated. The residue is chromatographed on 250 g. of silica gel which has previously been acid-washed to pH 4 (Silicar CC₄, 100–200 mesh, Mallincrodt Co.), eluting with 3 l. of 25–75% ethyl acetate-Skellysolve B gradient, collecting 100-ml. fractions. The fractions shown to have the desired product free of starting material by TLC are combined and concentrated under reduced pressure to give the title compound containing the cis —CH=CH moiety.

Following the procedures of Preparation 8, but replacing methyl 9-bromo-3-oxa-3,7-inter-m-phenylene-4,5,6-trinor-7-nonynoate with methyl 9-bromo-3-oxa-4,7-inter-o-phenylene-5,6-dinor-7-nonynoate, methyl 10-bromo-3-oxa-4,8-inter-m-phenylene-5,6,7-trinor-8-decynoate, or methyl 11-bromo-3-oxa-4,9-inter-p-phenylene-5,6,7,8-tetra-nor-9-undecyanoate (from the paragraphs following Preparation 7), there is obtained the corresponding formula-LV enoate compounds in which cis—CH=CH— has replaced —C ≡ C—.

PREPARATION 9

Methyl 9-Bromo-3-oxa-3,7-inter-m-phenylene-4,5,6-trinor-trans-7-nonenoate. (Formula LVI: $C_jH_{2j}$ and $C_pH_{2p}$ are valence bonds in meta relationship, $C_qH_{2q}$ is methylene, Hal is bromo, $R_{26}$ is hydrogen and $R_{10}$ is methyl).

A solution of the compound represented by the formula

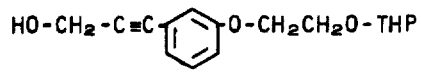

(1.0 g., Preparation 7, step e) in 20 ml. of tetrahydrofuran is cooled to −10° C. This solution is added to a fresh solution of lithium aluminum hydride (110% of theory) in tetrahydrofuran. The reaction mixture is stirred for 16 hours at 25° C. ambient temperature. Then, water (20 ml.) is added, and the resulting solution is acidified with one N hydrochloric acid, and then extracted with ethyl acetate. The extract is washed successively with aqueous sodium bicarbonate solution and brine, dried, and evaporated under reduced pressure. The residue is chromatographed on silica gel, eluting with a 25–75% ethyl acetate-Skellysolve B gradient, combining fractions shown to have the desired product by TLC, and removing solvent from those combined fractions under reduced pressure to yield a compound represented by the formula

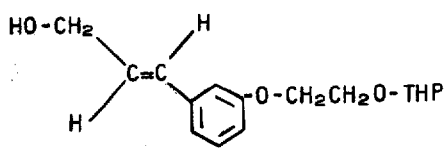

Thereafter, following the procedures of Preparation 7, steps f through g, there is obtained the title compound containing the trans—CH=CH— moiety.

Following the procedures of Preparation 9, but replacing that nonynoate with the compound having the formula

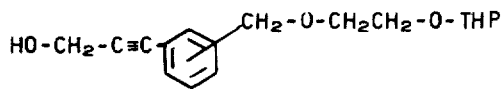

wherein the THP-terminated moiety is attached to the ring in ortho, meta, or para configuration, there is obtained the corresponding formula-LVI compound in which trans —CH=CH— has replaced — ≡C—.

PREPARATION 10

Optically Active Bicyclo[3.1.0]-hex-2-ene-6-endo-carboxaldehyde

Following the procedure of Preparation 1 of U.S. Pat. No. 3,711,515, racemic bicyclo[3.1.0]hex-2-ene-6-endo-carboxaldehyde is prepared from bicyclo[2.2.1-]hepta-2,5-diene and peracetic acid.

The racemic compound is resolved by the procedure of Example 13 of U.S. Pat. No. 3,711,515, forming an oxazolidine as follows.

Racemic bicyclo[3.1.0]hex-2-ene-6-endo-carboxaldehyde (12.3 g.) and l-ephedrine (16.5 g.) are dissolved in about 150 ml. of benzene. The benzene is removed under vacuum and the residue taken up in about 150 ml. of isopropyl ether. The solution is filtered, then cooled to −13° C. to yield crystals of 2-endo-bicyclo-[3.1.0]hex-2-en-6-yl-3,4-dimethyl-5-phenyl-oxazolidine, 11.1 g., m.p. 90°–92° C. Three recrystallizations from isopropyl ether, cooling each time to about −2° C., yield crystals of the oxazolidine, 2.2 g., m.p. 100°–103° C., now substantially a single isomeric form as shown by NMR.

The above re-crystallized oxazolidine (1.0 g.) is dissolved in a few ml. of dichloromethane, charged to a 20 g. silica gel column and eluted with dichloromethane. The silica gel is chromatography-grade (Merck), 0.05–0.2 mm. particle size, with about 4–5 g. of water per 100 g. Fractions of the eluate are collected, and those shown by thin layer chromatography (TLC) to contain the desired compound are combined and evaporated to an oil (360 mg.). This oil is shown by NMR to be the desired title compound, substantially free of the ephedrine, in substantially a single optically-active isomeric form. Points on the circular dichroism curve are ($\lambda$ in nm.,$\theta$): 350, 0; 322.5, −4,854; 312, −5,683; 302.5, −4,854; 269, 0; 250, 2,368; 240, 0; and 210, −34,600.

EXAMPLE 1 dl-Methyl 7-[Endo-6-(1-heptenyl)-3-oxobicyclo[3.1.0]hex-2α-yl] -3-oxa-3,7-inter-m-phenylene-4,5,6-trinor-heptanoate (Formula XLIV, Chart E: G is n-pentyl; $R_2$, $R_9$, and $R_{26}$ are hydrogen; $R_{10}$ is methyl; Z' is

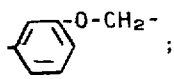

and ~ is alpha and endo).

A. A solution prepared from endo-6-(1-heptenyl)-3-(1-pyrrolidyl)-bicyclo[3.1.0]hex-2-ene (Preparation 1, 5.0 g.) and methyl m-(chloromethyl)-phenoxyacetate (Preparation 2, 4.4 g.) in 60 ml. of dioxane is stirred under a nitrogen atmosphere at about 25° C for 2 days and then heated under reflux for 7 hrs. To the reaction mixture is added water. The solution is heated on a steam bath, cooled and extracted with ether. The extract is washed, first with dilute (about 5% hydrochloric acid, then brine, and dried and concentrated. The residue is chromatographed on 700 g. of silica gel prepared with 20% ether-isomeric hexane mixture (Skellysolve B) and eluted with 1.5 l. of 20% ether-Skellysolve B, 1.5 l. of 25% ether-Skellysolve B, and 1.5 l. of 30% ether-Skellysolve B, collecting 100-ml. fractions. Fractions 25–31 give the title compound (1.7 g.).

B. Alternate synthesis. - A solution of potassium tert-butoxide (9.0 g.) in 500 ml. of nitrogen-purged tetrahydrofuran is added dropwise during 45 min. to a stirred solution of the formula-XLIII bicyclo olefin, endo-6-(1-heptenyl)bicyclo[3.1.0]hexan-3-one (see Example 9 of West Germany Offenlegungsschrift No. 1,937,912, cited above) (10.0 g.), and methyl m-(chloromethyl)phenoxyacetate (Preparation 2, 13 g.) in 250 ml. of tetrahydrofuran under nitrogen at 25° C. The resulting mixture is acidified at once with 120 ml. of 5% hydrochloric acid, and then is concentrated under reduced pressure below 40° C. to remove most of the tetrahydrofuran. Water (400 ml.) is added to the residue, and the mixture is extracted with three 400-ml. portions of ethyl acetate. The combined extracts are washed successively with aqueous sodium thiosulfate solution and brine, dried, and concentrated under reduced pressure. The residue is chromatographed over 4 kg. of silica gel wet-packed with 20% ether-isomeric hexane mixture (Skellysolve B) and eluted with ether-Skellysolve B mixtures having 20–30% ether. Fractions shown by TLC to contain the desired alkylation product are combined to yield the formula-XLIV (Chart E) alkylated olefin title compound.

Following the procedure of Example 1-B but replacing the formula-XLIII (Chart E) endo-6-(1-heptenyl)-bicyclo[3.1.0]hexan-3-one with the corresponding bicyclo olefins prepared by reaction of the -tetrahydropyranyl ether of endo-bicyclo[3.1.0]hexan-3-ol-6-carboxaldehyde with intermediate quaternary phosphonium halides (see above-cited West Germany Offenlegungsschrift No. 1,937,912) prepared from 1-bromobutane, 1-chloropentane, 1-bromoheptane, and 1-chlorooctane, there are obtained the corresponding formula-XLIV alkylated olefin compounds wherein G is straight chain alkyl of 3, 4, 6, and 7 carbon atoms, respectively.

Also following the procedure of Example 1-B but employing instead formula-XLIII bicyclo olefins prepared from 1-bromo-2-fluorobutane, 1-chloro-2-fluoro-pentane, 1-bromo-2-fluorohexane, 1-bromo-2-fluoroheptane, and 1-chloro-2-fluorooctane, there are obtained the corresponding formula-XLIV alkylated olefin compounds wherein G is straight chain alkyl of 3 to 7 carbon atoms, inclusive, with a fluoro substituent at the 1-position.

Also following the procedure of Example 1-B but employing, instead, formula-XLIII bicyclo olefins prepared from primary bromides of the formula $R_{27}$—$(CH_2)_b$—$CH_2Br$, wherein $b$ is one, 2, 3, or 4, and $R_{27}$ is isobutyl, tert-butyl, 3,3-difluorobutyl, 4,4-difluorobutyl, 4,4,4-trifluorobutyl, and 3,3,4,4,4-pentafluorobutyl, there are obtained compounds corresponding to the formula-XLIV product of Example 1-B with $R_{27}—(CH_2)_b—CH=CH—$ in place of the 1-heptenyl moiety.

Also following the procedure of Example 1-B but employing, instead, formula-XLIII bicyclo olefins prepared from primary bromides of the formula $CH_3—(CH_2)_c—CR_{21}R_{22}—CH_2Br$ wherein c is 2, 3, or 4, and $R_{21}$ and $R_{22}$ are methyl or ethyl, e.g. $CH_3—(CH_2)_2—C(C_2H_5)_2—CH_2—Br$, $CH_3—(CH_2)_3—CH(CH_3)—CH_2—Br$, $CH_3—(CH_2)_3—CH(C_2H_5)—CH_2Cl$, $CH_3—(CH_2)_3—C(CH_3)_2—CH_2—Br$, and $CH_3—(CH_2)_3—C(CH_3)(C_2H_5)—CH_2Br$, there are obtained the corresponding formula-XLIV alkylated olefin compounds wherein G is mono- or di-substituted at the 1-position with methyl or ethyl.

Also following the procedure with Example 1-B but employing, instead, formula-XLIII bicyclo olefins prepared from α-bromotoluene, (2-bromoethyl)benzene, (5-chloropentyl)-benzene, (6-bromohexyl)benzene, and (7-iodoheptyl)benzene; from (1-chloroethyl)-benzene, (1-bromopropyl)benzene, (2-bromopropyl)benzene, (3-chloropentyl)benzene, (4-bromopentyl)benzene, (6-bromononyl)benzene and (7-bromononyl)-benzene; from 1-bromo-2-phenylpropane, 1-bromo-2-methyl-2-phenylpropane, 1-chloro-2-ethyl-3-phenylpropane, 1-bromo-2-methyl-4-phenylbutane, and 1-bromo-2,2-dimethyl-5-phenylpentane; from α-bromo-m-xylene, α-chloro-p-ethyltoluene, α-bromo-p-chlorotoluene, α'-chloro-α,α,α-trifluoro-m-xylene, 1-(2-bromoethyl)-4-fluorobenzene, 1-(5-bromopentyl)-2-chlorobenzene, 4-(3-iodopropyl)-1,2-dimethoxybenzene, and 1-(3-bromohexyl)-2,4,6-trimethylbenzene; and from (2-bromo-1-fluoroethyl)benzene, (2-bromo-1-fluoropropyl)benzene, (2-chloro-fluoro-1-methylpropyl)benzene, (5-bromo-4-fluoropentyl)benzene, (7-iodo-6-fluoropentyl)benzene, (4-bromo-3,3-difluorobutyl)benzene, and (6-bromo-5,5-difluorohexyl)benzene, there are obtained the corresponding formula-XLIV alkylated olefin compounds wherein G is

including compounds wherein $C_tH_{2t}$ is substituted with one or 2 fluoro atoms.

Also following the procedure of Example 1-B, but using formula-XLIII bicyclo olefins obtained from the secondary bromides of the formula

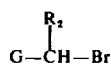

wherein G and $R_2$ are as defined above, $R_2$ being alkyl, there are obtained formula-XLIV alkylated olefins corresponding to the product of Example 1-B with

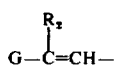

in place of the 1-heptenyl moiety.

Also following the procedure of Example 1-B, but using formula-XLIII bicyclo olefins obtained from bicyclo-[3.1.0]hexane reactants with

in place of

wherein $R_9$ is as defined above, there is obtained formula-XLIII alkylated olefins corresponding to the product of Example 1-B with

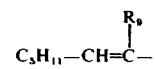

in place of the 1-heptenyl moiety.

Also following the procedure of Example 1-B, but using formula-XLIII bicyclo olefins obtained from bicyclo-[3.1.0]hexane reactants with

in place of

and primary and secondary bromides of the formula

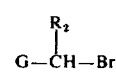

(as above defined), there are obtained formula-LIV alkylated olefins corresponding to the product of Example 1-B with

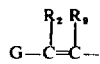

in place of the 1-heptenyl moiety.

Also following the procedure of Example 1-B but using a larger amount of potassium tert-butoxide (16 g.) and maintaining the reaction mixture for 8 hrs. at 25° C. before addition of hydrochloric acid, a product is obtained which contains substantial amounts of both the above described 2α-yl isomer and the corresponding 2β-yl isomer. These isomers are separated by the above-described silica gel chromatography.

Also following the procedure of Example 1-B but using exo formula-XLIII bicyclo olefins in place of the endo reactant of Example 1-B, there are obtained the corresponding exo formula-XLIV alkylated olefins.

Also following the procedure of Example 1-B but replacing the methyl m-(chloromethyl)phenoxyacetate alkylating agent with the formula-LIII and -LIV compounds, methyl 3-[m-(chloromethyl)phenoxy]propionate, methyl 9-bromo-3-oxa-3,7-inter-m-phenylene-4,5,6-trinor-7-nonynoate, and methyl 10-bromo-3-oxa-4,8-inter-m-phenylene-5,6,7-trinor-8-decynoate, there are obtained alpha and beta, exo and endo, formula-XLIV alkylated olefins corresponding to the product of Example 1-B with

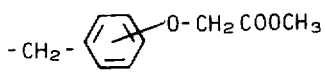

replaced with

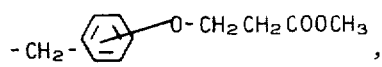

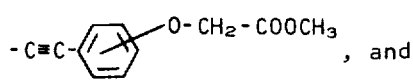, and

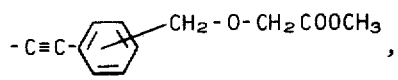

respectively. In the same manner, but using, according to Example 1-B, other esters of the above-described formula-LIII and -LIV alkylating agents within the scope of $R_{10}$ as above-defined, e.g., the isopropyl, tert-butyl, octyl, cyclohexyl, benzyl, and phenyl esters, there are obtained the corresponding formula-XLIV esters.

Also following the procedure of Example 1-B, but using in combination each of the above-described alternative formula-XLIII bicyclo olefins and each of the above-described alternative formula-LIII or -LIV omega-halo alkylation agents, there are obtained formula-XLIV alkylated olefins corresponding to the product of Example 1-B but different therefrom with respect to both the carboxylate-terminated side chain and the side chain attached to the cyclopropane ring in the product.

Also following the procedure of Example 1-B, but using in place of the formula-LIII halo alkylating agent of that Example, each of the other alkylating agents within the scope of

as above defined, i.e., alkylating agents of formulas LIII and LIV as above-described, there are obtained alpha and beta exo and endo formula-XLIV compounds corresponding to the product of Example 1-B with each of the other

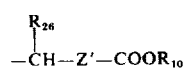

side chains in place of the

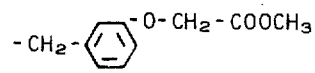

side chain of the Example 1-B product. For example, using as formula-LIII alkylating agents in the Example 1-B procedure, the following compounds wherein Et is ethyl;

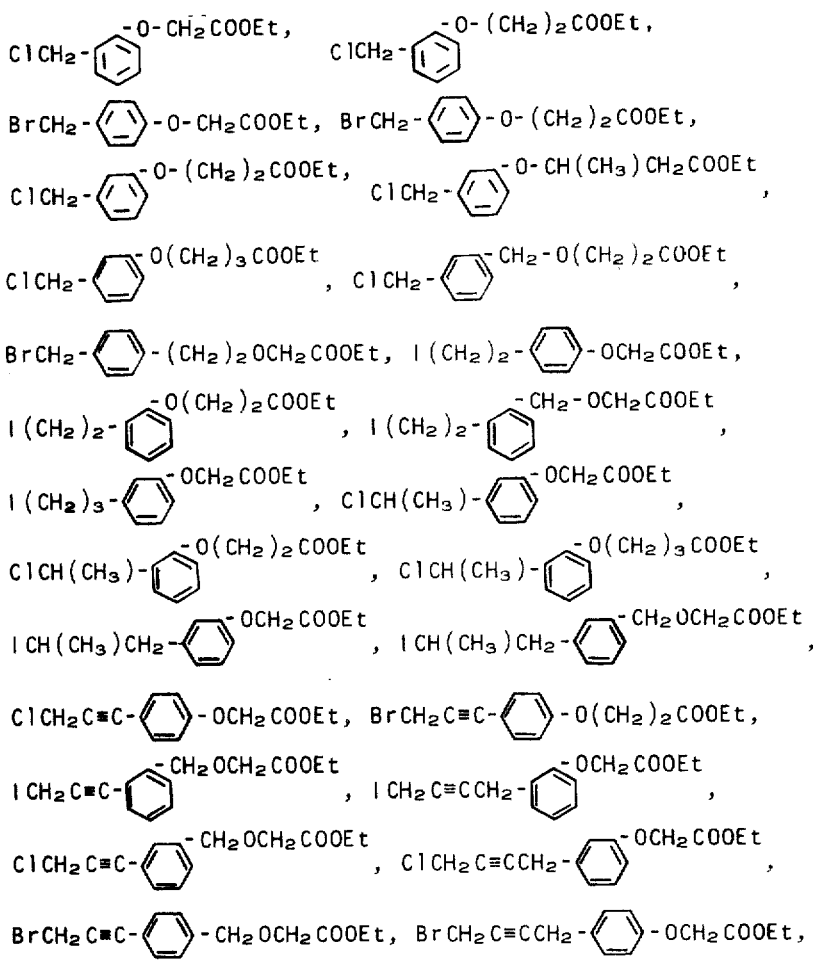

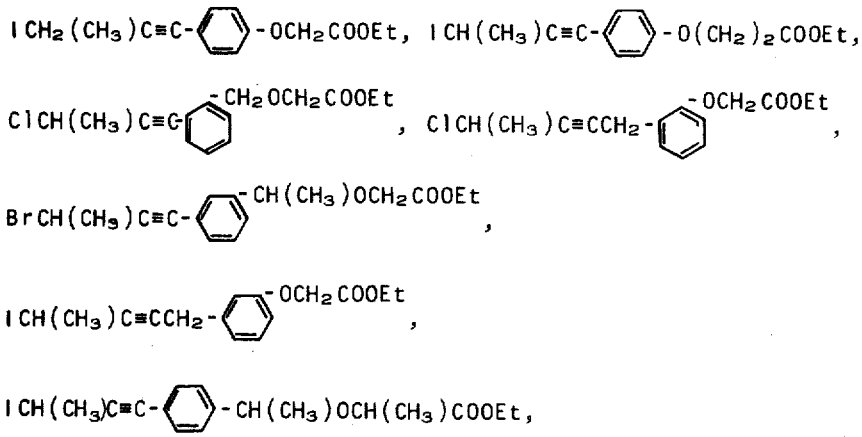

there are obtained exo and endo, alpha and beta, formula-XLIV alkylated bicyclo[3.1.0]hexanes each having a carboxylate-terminated side chain corresponding to one of the specific omega-halo alkylating agents. For example, the side chain will be alpha or beta

when the alkylating agent is

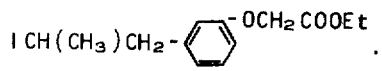

Also following the procedure of Example 1-B, but using in combination each of the alternative alkylating formula-LIII and -LIV agents within the scope of

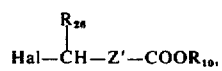

including the specific examples of those just mentioned, and each of the above-described formula-XLIII alternative bicyclo[3.1.0]hexane olefin reactants, there are obtained formula-XLIV exo and endo, alpha and beta, compounds corresponding to the products of Example 1-B, but different therefrom with respect to both the carboxylate-terminated side chain and the side chain attached to the cyclopropane ring of the product. In the same manner, alternative alkylating agents within the scope of

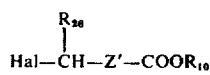

wherein $R_{10}$ is other than ethyl, e.g., methyl, isopropyl, tert-butyl, octyl, cyclohexyl, benzyl, phenyl, and $\beta,\beta,\beta$-trichloroethyl are used.

EXAMPLE 2 dl-Methyl 7-[Endo-6-(1,2-dihydroxyheptyl)-3-oxobicyclo[3.1.0]hex-2α-yl]-3-oxa-3,7-inter-m-phenylene-4,5,6-trinor-heptanoate (Formula XLV, Chart E: G' is n-pentyl; $R_2$, $R_9$, and $R_{26}$ are hydrogen; $R_{10}$ is methyl; Z' is

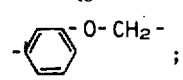

and ~ is alpha and endo).

Refer to Chart E. To a solution of dl-methyl 7-[endo-6-(1-heptenyl)-3-oxobicyclo[3.1.0]hex-2α-yl]-3-oxa-3,7-inter-m-phenylene-4,5,6-trinor-heptanoate (Example 1, 1.7 g.) in 30 ml. of tetrahydrofuran at 50° is added with stirring osmium tetroxide (200 mg.) followed by potassium chlorate (1.2 g.) and 15 ml. of water. The reaction mixture is maintained at 50° for 2 hrs., cooled, the tetrahydrofuran is removed, and the aqueous phase is extracted with dichloromethane. The organic layer is dried and concentrated and the residue is chromatographed on 200 g. of silica gel. The column is eluted with 1 l. of 35% ethyl acetate-benzene and 1 l. of 40% ethyl acetate-benzene, collecting 30-ml. fractions. Fractions 26–30 contain one isomer (faster moving, less polar) of the title compound (350 ml.). Fractions 32–37 contain the other slower-moving (more polar) isomer (450 mg.). These materials show infrared spectral absorption at 330 cm⁻¹.

Following the procedure of Example 2 but using the hex-2β-yl isomer in place of the hex-2α-yl isomer of the bicyclo reactant, dl-methyl 7-[endo-6-(1,2-dihydroxyheptyl)-3-oxobicyclo[3.1.0]hex-2β-yl]-3-oxa-3,7-inter-m-phenylene-4,5,6-trinor-heptanoate is obtained.

Also following the procedure of Example 2, each of the formula-XLIV exo and endo, alpha and beta, saturated and acetylenic bicyclo[3.1.0 hexane esters defined above after Example 1 is oxidized to mixtures of the corresponding isomeric formula-XLV dihydroxy compounds.

EXAMPLE 3 dl-3-Oxa-3,7-inter-m-phenylene-4,5,6-trinor-PGE$_1$ Methyl Ester (Formula XVI: C$_q$H$_{2q}$ and C$_p$H$_{2p}$ are valence bonds in metal relationship, G is n-pentyl, Q is

R$_1$ is methyl, and ~ is alpha) and dl-15-Beta-3-oxa-3,7-inter-m-phenylene-4,5,6-trinor-PGE$_1$ Methyl Ester

(Q is H OH).

Refer to Chart E. To a solution of the formula-XLV dihydroxy compound dl-methyl 7-[endo-6-(1,2-dihydroxyheptyl)-3-oxobicyclo[3.1.0]hex-2α-yl]-3-oxa-3,7-inter-m-phenylene-4,5,6-trinor-heptanoate (800 mg. of a mixture of the slower and faster moving isomers of Example 2) in 10 ml. of pyridine, cooled to 0°, is added 1.2 ml. of methane-sulfonyl chloride. The reaction mixture is stirred for 2 hrs. and 20 g. of ice is added. The mixture is extracted with ether-dichloromethane (1:1) and the organic layer is washed successively with dilute hydrochloride acid, water, saturated aqueous sodium bicarabonate, and brine, dried, and concentrated. The residue, containing the bismesylate, is treated with 15 ml. of acetone and 10 ml. of water and stirred for 8–16 hrs. at 25°. The acetone is removed in vacuo and the remaining solution is extracted with dichloromethane. The extract is dried and concentrated and the residue is chromatographed on 150 g. of silica gel using 500 ml. ethyl acetate followed by 3% methanol ethyl acetate as eluting solvent while collecting 30-ml. fractions. Fractions 15–24 are combined and concentrated to yield the 15-β PGE$_1$ title compound (50 mg.); mass spectral peak at 404; ultraviolet absorption at 216 ($\epsilon$ = 8100), 264 ($\epsilon$ = 1100), 272 ($\epsilon$ = 1600) and 278 ($\epsilon$ = 1500)mμ. Fractions 26–35 are combined and concentrated to yield a residue which is rechromatographed on 10 g. of silica gel using the same solvent system and collecting 1.5 ml. fractions. Fractions 22–29 are combined and concentrated to give the PGE$_1$ title compound (75 mg.); mass spectral peak at 404; ultraviolet absorption at 216 ($\epsilon$ = 7700), 254, 272 ($\epsilon$ = 1500), and 278 ($\epsilon$ = 1400) mμ.

Following the procedures of Example 3, each of the formula-XLV dl-endo-1,2-dihydroxy oxa-phenylene esters following Example 2 is transformed to the corresponding dl-endo-1,2-dimesyloxy oxa-phenylene ester, and thence to the corresponding PGE type compound or its isomers.

Also following the procedures of Example 3, each of the formula-XLV and dl-exo-1,2-dihydroxy-oxa-phenylene esters corresponding to the above dl-endo-1,2-dihydroxy esters is transformed to the corresponding dl-exo-1,2-dimesyloxy ester, and thence to the corresponding PGE type compound or its isomers.

By the above-outlined procedures, following the steps of Chart E, there are obtained the specific PGE-type esters represented by figures XVI and XVIII, e.g. the esters of the dl-oxa-phenylene PGE$_1$ compounds and 5,6-dehydro-PGE$_2$ compounds, including their 8-iso and 15-epi (β) forms. For example, dl-5,6-dehydro-3-oxa-3,7-inter-m-phenylene-18-phenyl-4,19,20-trinor-PGE$_2$ methyl ester and its 15-epimer are obtained from dl-methyl 7-[endo-6-(cis-4-phenyl-1-butenyl)-3-oxobicyclo[3.1.0]hex-2α-yl]-3-oxa-3,7-inter-m-phenylene-4,5,6-trinor-7-nonynoate (Example 10 hereinafter) by way of the dihydroxy and bis(mesylate) intermediates of Chart E, following Example 3, as represented by the following formulas:

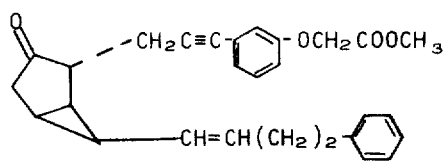

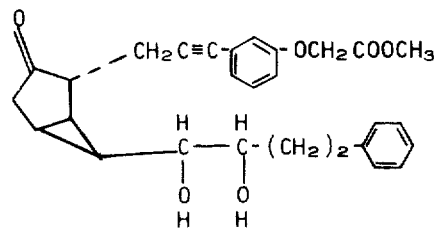

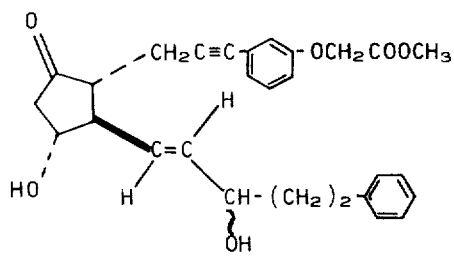

Also following the procedure of Example 3, but replacing methanesulfonyl chloride with an alkanesulfonyl chloride or bromide or with an alkanesulfonic acid anhydride, wherein the alkane moiety contains 2 to 5 carbon atoms, inclusive, there is obtained from each dihydroxy compound the corresponding bis(sulfonic acid) esters encompassed by formula XLVI.

In each of the above transformations in Example 3, the monosulfonic acid ester is also obtained as a by-product, which is reacted with additional alkanesulfonyl halide or alkanesulfonic acid anhydride to give the corresponding bis(sulfonic acid) ester and thence recycled back to additional formula-XLVII product.

For satisfactory yields of the bis-sulfonic acid ester, R$_{10}$ is not hydrogen. Those intermediate compounds in which R$_{10}$ is haloethyl, e.g., β,β,β-trichloroethyl, are especially useful in the sequence of reactions leading to the acid form of the prostaglandin-like products. Each of the exo and endo, alpha and beta, saturated and unsaturated oxa-phenylene bis(alkanesulfonic acid) esters is transformed to the corresponding oxa-phenylene PGE type compound encompassed by formula-XLVII.

EXAMPLE 4 dl-3-Oxa-3,7-inter-m-phenylene-4,5,6-trinor-PGF$_{1\alpha}$ Methyl Ester and
dl-3-Oxa-3,7-inter-m-phenylene-4,5,6-trinor-PGF$_{1\beta}$ Methyl Ester (Formula XX: C$_g$H$_{2g}$ and C$_p$H$_{2p}$ are valence bonds in meta relationship, G is n-pentyl, Q is

R$_1$ is methyl, and ~ is alpha for the carboxyl-containing moiety and either alpha or beta for the ring hydroxyl).

Refer to Chart A. A solution of dl-3-oxa-3,7-inter-m-phenylene-4,5,6-trinor-PGE$_1$ methyl ester (Example 3, 300 mg.), 20 ml. of tetrahydrofuran, 2.0 ml. of hexamethyldisilazane, and 0.15 ml. of trimethylsilyl chloride is stirred at 25° for 20 hrs. The reaction mixture is concentrated in vacuo, benzene is added, the solution concentrated and this procedure is repeated. The residue is dissolved in 10 ml. of methanol, cooled in an ice-methanol bath, and sodium borohydride (60 mg.) in 20 ml. of cold water is added dropwise. The methanol is removed and the aqueous phase is extracted with dichloromethane, and the resulting dichloromethane solution is dried and concentrated in vacuo. The residue is chromatographed on 45 g. of silica gel using 70 ml. of ethyl acetate and then a gradient of 0–8% methanol ethyl acetate as eluting solvent, collecting 10-ml. fractions. Fractions 22–36 are combined and concentrated to yield the PGF$_{1\alpha}$ -type title compound (100 mg.); mass spectral peak for tris-trimethylsilyl derivative at 622. Fractions 37–42 are combined and concentrated to yield a residue which is chromatographed on a preparative silica gel plate using 5% methanol-methylene chloride as eluting solvent. From the plate is obtained the PGF$_{1\beta}$ -type title compound (25 mg.); mass spectral peak for tris-trimethylsilyl derivative at 622.

Following the procedure of Example 4, dl-3-oxa-4,7-inter-o-phenylene-5,6-dinor-PGE$_1$ ethyl ester (Example 8 hereinafter) is transformed to dl-3-oxa-4,7-inter-o-phenylene-5,6-dinor-PGF$_{1\alpha}$ and -PGF$_{1\beta}$ ethyl esters.

Also following the procedure of Example 4, dl-5,6-dehydro-3-oxa-3,7-inter-m-phenylene-18-phenyl-4,19,20-trinor-PGE$_2$ methyl ester (following Example 3) is transformed to the corresponding PGF$_{2\alpha}$ and PGF$_{2\beta}$ type compounds.

Also following the procedure of Example 4, the alkyl ester and free acid forms of formula-XX to -XXIII oxa-phenylene PGF compounds in their various spatial configurations, e.g., the PGF$_{1\alpha}$, PGF$_{1\beta}$, PGF$_{2\alpha}$, PGF$_{2\beta}$, trans-5,6-dehydro-PGF$_{1\alpha}$ and -PGF$_{1\beta}$ type compounds and their 8-iso and 15-beta isomers, are prepared by reduction of the corresponding formula XVI-to -XIX PGE-type alkyl ester or free acid, including those described above after Example 3.

EXAMPLE 5 dl-3-Oxa-3,7-inter-m-phenylene-4,5,6-trinor-PGA$_1$
(Formula-XXIV: C$_g$H$_{2g}$ and C$_p$H$_{2p}$ are valence bonds in meta relationship, G is n-C$_5$H$_{11}$, Q is

R$_1$ is hydrogen; and ~ is alpha).

Refer to Chart A. A solution of dl-3-oxa-3,7-inter-m-phenylene-4,5,6-trinor-PGE$_1$ methyl ester (Example 3, 300 mg.), 4 ml. of tetrahydrofuran and 4 ml. of 0.5 N hydrochloric acid is left standing at 25° for five days. Brine solution and dichloromethane-ether (1:3) are added and the mixture is stirred. The organic layer is separated, dried and concentrated. The residue is dissolved in ether which is washed with saturated aqueous sodium bicarbonate, dried and concentrated. The aqueous phase is quickly acidified with hydrochloric acid and extracted with dichloromethane which in turn is dried and concentrated. The residue is again dissolved in ether, extracted with aqueous sodium bicarbonate, and the aqueous phase is worked up as reported above. This procedure is repeated one additional time to yield the title compound (120 mg.). This material has mass spectral peaks at 372, 354, 189, and 185; and λ max., in ethanol, 215 mμ (ε 12,400), 272 (ε 2250) and 278 (ε 2150).

Following the procedure of Example 5, the formula XIV-to -XIX PGE compounds in their various spatial configurations described after Example 3 are transformed to the corresponding formula XXIV-to -XXVII PGA compounds, either as esters or as free acids.

EXAMPLE 6 dl-Ethyl 7-[Endo-6-(1-heptenyl)-3-oxobicyclo[3.1.0]hex-2α-yl]-3-oxa-4,7-inter-o-phenylene-5,6-dinor-heptanoate (Formula-XLIV: G is n-pentyl; R$_2$, R$_9$, and R$_{26}$ are hydrogen; R$_{10}$ is ethyl; Z' is

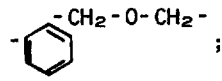

and ~ is alpha and endo).

The enamine of the formula-XLIII bicyclo-olefin is first prepared as follows. A mixture of endo-6-(cis- and trans-1-heptenyl)-bicyclo[3.1.0]hexan-3-one (10 g.), benzene (200 ml.), and pyrrolidine (15 ml.) is heated at reflux under a Dean-Stark water trap for 2 hrs. Thereafter about 140 ml. of distillate is taken off over a period of about 30 min. To the remaining liquid is added 100 ml. of toluene and the mixture is concentrated on a rotating evaporator under vacuum. A second portion of toluene (50 ml.) is added, and the mixture concentrated to give the enamine residue.

The above enamine, together with ethyl o-(bromomethyl)-benzyloxyacetate (Preparation 3 above, 15 g.), and dry tetrahydrofuran (200 ml.) is heated at reflux for 4 hrs. and thereafter stirred at about 25° C. for 16 hrs. Water (25 ml.) is added and the mixture heated for 20 min. on a steam bath. Thereafter the volatiles are removed under vacuum, the residue is diluted with ether, and the organic solution is washed successively with dilute acid, water, dilute base, water, and brine, and finally dried and concentrated under vacuum. The residue is chromatographed on a column prepared by wet-packing 1300 g. of silica gel (E. Merck) with 2.5 l. of 25% diethyl ether in Skellysolve B and 13 ml. of absolute ethanol. The column is eluted with 2 l. of 25% ether in Skellysolve B and then gradient-eluted with 8 l. of 25–50% ether-Skellysolve B. Fractions of about 200 ml. are combined on the basis of TLC data. From fractions 24–31 there is obtained 2.9 g. of the desired formula-XLIV title compound as a mixture of cis and trans forms. This material has key absorptions in its NMR spectrum at about 7.21 (apparent singlet), 5.38–5.8 (multiplet), 4.62 (singlet), 4.06 (singlet), and 4.0–4.35 (quartet) δ. It has mass spectral lines at 398 and 294.

EXAMPLE 7 dl-Ethyl 7-[endo-6-(1,2-dihydroxyheptyl)-3-oxobicyclo[3.1.0-]hex-2α-yl]-3-oxa-4,7-inter-o-phenylene-5,6-dinor heptanoate (Formula-XLV: G' is n-pentyl; $R_2$, $R_9$, and $R_{26}$ are hydrogen; $R_{10}$ is ethyl; Z' is

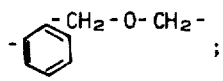

and ~ is alpha and endo).

Refer to Chart E. To a solution of dl-ethyl 7-[endo-6-(1-heptenyl)-3-oxobicyclo[3.1.0]hex-2α-yl]-3-oxa-4,7-inter-o-phenylene-5,6-dinor-heptanoate, as a mixture of its isomers (Example 6, 2.8 g.) in dry tetrahydrofuran (150 ml.) at 50° C. is added 0.15 g. of osmium tetroxide followed by 2.8 g. of potassium chlorate in 60 ml. of water. The mixture is stirred vigorously at 50° C. for about 1.5 hrs. and is then concentrated under vacuum. The residue is extracted with dichloromethane. The extract is washed with water and brine, and then finally dried and concentrated under vacuum. The residue is chromatographed on a column prepared by wet-packing 500 g. of silica gel (E. Merck) with 1 liter of 50% ethyl acetate in Skellysolve B and 5 ml. of absolute ethanol. The column is eluted with 1 l. of 50% ethyl acetate in Skellysolve B and then gradient eluted with 4 l. of 50–75% ethyl acetate in Skellysolve B. Fractions of 100 ml. each are combined on the basis of TLC data. From fractions 12–29 there is obtained 2.6 g. of the title compound.

EXAMPLE 8 dl-3-Oxa-4,7-inter-o-phenylen-5,6-dinor-PGE$_1$ Ethyl Ester (Formula-XIV: $C_pH_{2p}$ is a valence bond, $C_pH_{2p}$ are in ortho relationship, G is n-pentyl, Q is

$R_1$ is ethyl, and ~ is alpha) and dl-15-Beta-3-oxa-4,7-inter-o-pnenylene-5,6-dinor-PGE$_1$ Ethyl Ester

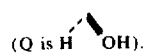

(Q is H OH).

Refer to Chart E. The formula-XLVI bismesylate is first prepared as follows. To a mixture of dl-ethyl 7-[endo-6-(1,2-dihydroxyhepthyl)-3-oxobicyclo[3.1.0]hex-2α-yl]-3-oxa-4,7-inter-o-phenylene-5,6-dinor-heptanoate (Example 7, 2.6 g.) and 30 ml. of dry pyridine at 0° C. is added, with stirring, 2.7 ml. of methanesulfonyl chloride over a one-minute period. The mixture is stirred at 0° C. for 2.5 hrs., then cooled to about −10° C. and diluted with 2 ml. of water added dropwise over a 5-minute period. Ice (20 g.) is added, and, after stirring the mixture for 5 min., about 150 ml. of ether-dichloromethane (3:1) is added. The organic solution was washed successively with dilute hydrochloric acid, water, dilute sodium bicarbonate solution, and brine, and finally dried and concentrated under vacuum to yield a mixture of the mesylates.

The residue of mesylates is converted to the PGE-type product by contacting with a mixture of acetone (100 ml.) and water (50 ml.) at about 25° C. for 16 hrs. Additional water (100 ml.) is added and the mixture concentrated under vacuum to remove acetone. The residue is extracted with a mixture of ether-dichloromethane (3:1) and the organic extract is washed with dilute sodium bicarbonate solution and brine, then dried and concentrated under vacuum. The residue (2.5 g.) is chromatographed on a column prepared by wet-packing 500 g. of silica gel (E. Merck) with one liter of ethyl acetate and 5 ml. of absolute ethanol. The column is eluted with 2.6 liters of ethyl acetate, then 400 ml. of 2% ethanol in ethyl acetate, then 500 ml. of 4% ethanol in ethyl acetate and finally with 2 liters of 10% ethanol in ethyl acetate, collecting fractions of 100 ml. Fractions are combined on the basis of TLC data.

From fractions 8–14 is obtained 350 mg. of the 15-β PGE$_1$ title compound. This material has $\lambda_{max}$. 279 mμ (ε 19,400) in alcoholic potassium hydroxide; key absorptions in the NMR spectrum at about 7.2 (apparent singlet), 5.25–5.48 (multiplet), 4.58 (singlet), 5.25–5.48 (multiplet), 4.58 (singlet), 4.06 singlet, and 4.0–4.35 (quartet) δ; and mass spectral peaks at 414, 396, 310, and 292.

From fractions 18–37 is obtained 496 mg. of the PGE$_1$ title compound. This material has $\lambda_{max}$. 279 mμ (ε 21,750) in alcoholic potassium hydroxide; key absorptions in the NMR spectrum at about 7.18 (apparent singlet), 5.25–5.41 (multiplet), 4.58 (singlet), 4.02 (singlet), and 3.99–4.34 (quartet) δ; and mass spectral peaks at 414, 396, 310, and 292.

EXAMPLE 9 dl-Methyl 9-[Endo-6-(1,2-dihydroxy-2-methylheptyl)-3-oxobicyclo[3.1.0]hex-2α-yl]-3-oxa-3,7-inter-m-phenylene-4,5,6-trinor-cis-7-nonenoate Acetonide (Formula-XXXVII, Chart D: G is n-pentyl; J' is cis-

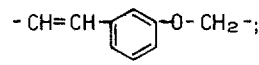

$R_9$ and $R_{26}$ are hydrogen; $R_2$, $R_{10}$, $R_{11}$, and $R_{12}$ are methyl; and ~ is endo and alpha).

Refer to the sequence of reactions from formula-L to formula XXVI, and to Chart D.

a. There is first prepared the formula-XLIII olefin. Following the procedure for the Wittig synthesis in Examples 27, 28, and 29 of West Germany Offlegungsschrift 1,937,912, cited above, but employing the tetrahydropyranyloxy ether of endo-bicyclo[3.1.0-]hexan-3-ol-6-carboxaldehyde and the Wittig ylide of 2-chloroheptane, there is obtained dl-endo-6-(2-methyl-1-heptenyl)-3-oxobicyclo[3.1.0]-hexan-3-one.

b. To a solution of the product of step a above (approximately 10.0 g.) in water is added a solution of potassium chlorate (10.0 g.) and osmium tetroxide (0.65 g.) in 250 ml. of water. The mixture is stirred vigorously for 5 hrs. at 50° C. Then, the cooled mixture is concentrated under reduced pressure, the residue is extracted repeatedly with dichloromethane, and the combined extracts are dried and evaporated. The residue is chromatographed on about 1000 g. of silica gel, and eluted successively with 3 l. of 10% ethyl acetate in a mixture of isomeric hexanes (Skellysolve B), with 5 l. of 25% ethyl acetate in Skellysolve B, and then with 50% ethyl acetate in Skellysolve B, collecting 500 ml. eluate fractions. Fractions shown by TLC to contain the desired product are combined and evaporated to dryness to give the formula-LI product, dl-endo-6-(1,2-dihydroxy-2-methylheptyl)bicyclo[3.1.0]hexan-3-one.

c. A solution of the product of step b above (about 8,0 g.) and 700 mg. of potassium bisulfate in 140 ml. of acetone is stirred at 25° C. for 64 hrs. Then, sodium carbonate monohydrate (710 mg.) is added, and the mixture is stirred 10 min. The acetone is evaporated at reduced pressure, and water is added. The aqueous solution is extracted respectedly with dichloromethane, and the extracts are combined, washed with water, dried, and evaporated. The residue is chromatographed on 400 g. of silica gel, being eluted with 2 l. of 10% ethyl acetate in Skellysolve B, and then with 4 l. of 15% ethyl acetate in Skellysolve B. The 15% ethyl acetate eluates are evaporated to give the formula-XXXVI ketal, dl-endo-6-(1,2-dihydroxy-2-methylheptyl)bicyclo[3.1.0]hexan-3-one acetonide.

d. To prepare the formula-XXXVII compound (Chart D), the ketal above is alkylated following the procedure of Example 1-B, but using the formula-XXXVI ketal above instead of the formula-XLIII bicyclo olefin, and, replacing methyl m-(chloromethyl)-phenoxyacetate with methyl 9-chloro-3-oxa-3,7-inter-m-phenylene-4,5,6-trinor-cis-7-nonenoate (Preparation 8, above), thereby yielding the desired formula-XXXVII title compound.

As shown in Chart D, the formula-XXXVII alkylated ketal is transformed via the formula-XXXVIII glycol, thence the mesylate, to a PGE-type compound. Concentrated hydrochloric acid (2.5 ml.) is added to a solution of the formula-XXXVII product above (about 2.0 g.) in a mixture of 50 ml. of tetrahydrofuran and 2.5 ml. of water. The mixture is stirred at 25° C. under nitrogen for 6 hrs. The resulting mixture is then concentrated under reduced pressure, and the residue is extracted with ethyl acetate. The extract is washed with brine, dried, and concentrated to dl-methyl-9[endo-6-(1,2-dihydroxy-2-methylheptyl)-3-oxobicyclo[3.1.0.-]hex-2a-yl]-3-oxa-3,7- inter-m-phenylene-4,5,6-trinor-cis-7-nonenoate (formula-XXXVIII). Thereafter, following the procedure of Example 3, there is obtained dl-15-methyl-3-oxa-3,5-inter-m-phenylene-4-nor-PGE$_2$ methyl ester.

Following the procedure of Example 9, but using formula-XLIII exo reactants in place of the endo reactant, there are obtained exo products in each corresponding intermediate of Example 9.

With excess base (e.g., 26 g.) and a longer reaction time (e.g., 24 hrs. at 25° C.) during the alkylation step, the production of a substantial amount of the beta isomer is assured.

Following the procedures of Example 9-d, but using the trans-7-nonenoate of Preparation 9, above, instead of the cis-7-nonenoate, there is obtained the corresponding formula-XXXVII alkylated ketal wherein the carboxy side chain is in trans configuration instead of cis.

Also following the procedures of Example 9, but replacing the formula-XLIII olefin with each of the endo and exo forms of the formula-XLIII bicyclo olefins described in the paragraphs following Example 1, there are obtained the corresponding alpha and beta, exo and endo, alkylated ketals within the scope of formula XXXVII.

Also following the procedures of Example 9-d, but replacing methyl 9-chloro-3-oxa-3,7-inter-m-phenylene-4,5,6,-trinor-cis-7-nonenoate with the formula-LV compounds of the paragraphs following Preparations 8 and 9, viz. cis or trans methyl 9-bromo-3-oxa-4,7-inter-o-phenylene-5,6-dinor-7-nonenoate, methyl 10-bromo-3-oxa-4,8-inter-m-phenylene-5,6,7-trinor-8-decenoate, and methyl 11-bromo-3-oxa-4,9-inter-p-phenylene-5,6,7,8-tetranor-9-undecenoate, there are obtained the corresponding formula-XXXVII compounds. Thereafter, these alkylated ketals are transformed following the steps of Chart D as described in Example 9 to the corresponding PGE$_2$ type compounds.

Also following the procedure of Example 9-d, but using in place of the nonenoate alkylating agent, methyl m-(chloromethyl)phenoxyacetate(Preparation 2), ethyl o-(bromoethyl)benzyloxyacetate (Preparation 3), methyl 9-bromo-3-oxa-3,7-inter-m-phenylene-4,5,6-trinor-7-nonynoate (Preparation 7), and methyl 11-bromo-3-oxa-4,9-inter-p-phenylene-5,6,7,8-tetranor-9-undecynoate (following Preparation 7), there are obtained alpha and beta, exo and endo, compounds corresponding to the product of Example 9 with

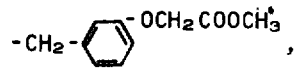

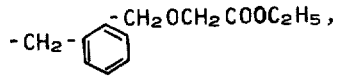

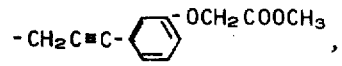

and

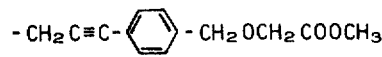

in place of the

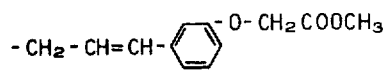

moiety of the Example-9 formula-XXXVII product. In the same manner, but using formula LIII-to -LVI alkylating agents within the scope of the formula

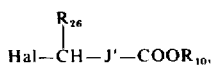

there are obtained the corresponding formula-XXXVII products.

Also following Example 9-d, other esters of the nonenoate alkylating agent and of the other above-mentioned alkylating agents within the scope of $R_{10}$ as above-defined, e.g., the methyl, isopropyl, tert-butyl, octyl, $\beta,\beta,\beta$-trichloroethyl, cyclohexyl, benzyl, and phenyl esters, there are obtained the corresponding esters of these alpha and beta, exo and endo, formula-XXXVII bicyclo[3.1.0]hexane cyclic ketal alkylation products.

Also following the procedure of Example 9 but using in combination each of the above-described alternative formula-XLIII bicyclo[3.1.0]hexane olefin reactants (e.g. following Example 1) and each of the above-described omega-halo alkylation reactants within the scope of

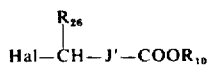

(e.g. following Example 1) there are obtained formula-XXXVII compounds corresponding to the product of Example 9 but different therefrom with respect to both the carboxylate-terminated side chain and the side chain attached to the cyclopropane ring of the product, and in their respective alpha or beta and exo or endo configuration.

Following the procedure of Example 9 but using in place of the acetonide each of the specific formula-XXXVII exo and endo, alpha and beta, saturated, cis and trans ethylenic, and acetylenic bicyclo[3.1.0]hexane cyclic ketal esters defined above, there are obtained the corresponding formula-XXXVIII dihydroxy compounds, and thence the corresponding PGE type compounds.

EXAMPLE 10 dl-Methyl 7-[Endo-6-(cis-4-phenyl-1-butenyl)-3-oxobicyclo[3.1.0]hex-2α-yl]-3-oxa-3,7-inter-m-phenylene-4,5,6-trinor-7-nonynoate (Formula-XLIV, Chart E; G is

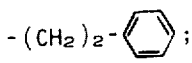

$R_2$, $R_9$, and $R_{26}$ are hydrogen; $R_{10}$ is methyl; Z' is

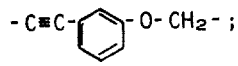

and ~ is endo and alpha).

Refer to Chart E. Following the procedures of Example 1-B, but replacing endo-6-(1-heptenyl)bicyclo[3.1.0]-hexan-3-one with endo-6-(cis-4-phenyl-1-butenyl)-bicyclo[3.1.0]hexan-3-one (Preparation 4), and replacing methyl m-(chloromethyl)phenoxyacetate with methyl 9-chloro-3-oxa-3,7-inter-m-phenylene-4,5,6-trinor-7-nonynoate (Preparation 7), there is obtained the title compound.

EXAMPLE 11 dl-Methyl 7-[Endo-6-(4-phenyl-1,2-dimesyloxy-butyl)-3-oxobicyclo[3.1.0.]hex-2α-yl]-3-oxa-3,7-inter-m-phenylene-4,5,6-trinor-7-nonynoate (Formula-XLVI, Chart E; G' is

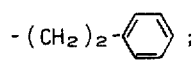

$R_2$, $R_9$, and $R_{26}$ are hydrogen; $R_{10}$ and $R_{13}$ are methyl; Z' is

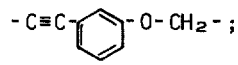

and ~ is alpha and endo).

a. There is first prepared the formula-XLV dihydroxy compound. Following the procedures of Example 2, but replacing dl-methyl 7-[endo-6-(1-heptenyl)-3-oxa-3,7-inter-m-phenylene-4,5,6-trinor-heptanoate with dl-methyl 7-[endo-6-(cis-4-phenyl-1-butenyl)-3-oxobicyclo[3.1.0]hex-2α-yl]-3-oxa-3,7-inter-m-phenylene-4,5,6-trinor-7-nonynoate (Example 10), there are obtained isomers of the desired formula-XLV compound, dl-methyl 7-[endo-6-(4-phenyl-1,2-dihydroxybutyl)-3-oxobicyclo[3.1.0]hex-2α-yl]-3-oxa-3,7-inter-m-phenylene-4,5,6-trinor-7nonynoate.

b. Following the procedures of Example 3, but replacing that formula-XLV dihydroxy heptanoate compound with the formula-XLV nonynoate compound of A above, there is obtained the desired formula-LXVI dimesyloxy title compound.

EXAMPLE 12 dl-Methyl 9-[Endo-6-(1,2-dihydroxy-4-phenyl-butyl)-3-oxobicyclo[3.1.0]hex-2α-yl]-3-oxa-3,7-inter-m-phenylene-4,5,6-trinor-trans-7-nonenoate Acetonide (Formula-XXVII, Chart D: G is

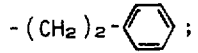

J' is trans

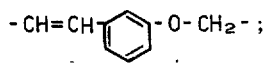

$R_2$, $R_9$, and $R_{26}$ are hydrogen; $R_{10}$, $R_{11}$, and $R_{12}$ are methyl; and ~ is endo and alpha)

Refer to the sequence of reactions from formula L to formula XXXVI, and to Chart D.

a. There is first prepared the formula-LI dihydroxy compound. To a solution of the formula-XLIII olefin (Preparation 4, above, approximately 10.0 g.) in water is added a solution of potassium chlorate (10.0 g.) and osmium tetroxide (0.65 g.) in 250 ml. of water. The mixture is stirred vigorously for 5 hrs. at 50° C. Then, the cooled mixture is concentrated under reduced pressure, the residue is extracted repeatedly with dichloromethane, and the combined extracts are dried and concentrated. The residue is chromatographed on about 1000 g. of silica gel, and eluted successively with 3 l. of 10% ethyl acetate in a mixture of isomeric hexanes (Skellysolve B), with 5 l. of 25% ethyl acetate in Skellysolve B, and then with 50% ethyl acetate in Skellysolve B, collecting 500 ml. eluate fractions. Fractions shown by TLC to contain the desired product are combined and evaporated to dryness to give dl-endo-6-(1,2-dihydroxy-4-phenylbutyl)-bicyclo[3.1.0]hexan-3-one formula-LI).

b. A solution of the product of step a above (about 8.0 g.) and 700 mg. of potassium bisulfate in 140 ml. of acetone is stirred at 25° C. for 64 hrs. Then, sodium carbonate monohydrate (710 mg.) is added, and the mixture is stirred 10 min. The acetone is concentrated at reduced pressure, and water is added. The aqueous solution is extracted repeatedly with dichloromethane, and the extracts are combined, washed with water, dried, and concentrated. The residue is chromatographed on 400 g. of silica gel, being eluted with 2 l. of 10% ethyl acetate in Skellysolve B, and then with 4 l. of 15% ethyl acetae in Skellysolve B. The 15% ethyl acetate eluates are concentrated to the formula-XXXVI ketal, dl-endo-6-(1,2-dihydroxy-4-phenylbutyl)-bicyclo[3.1.0]hexan-3-one acetonide.

c. To prepare the formula-XXXVII compound, the ketal above is alkylated following the procedure of Example 1-B, but replacing methyl m-(chloromethyl)-phenoxyacetate with methyl 9-chloro-3-oxa-3,7-inter-m-phenylene-4,5,6-trinor-trans-7-nonenoate (Preparation 9, above), thereby yielding the title compound.

Following the procedures of Example 9, the formula-XXXVII compound is transformed via the formula-XXXVIII and -XXXIX compounds to the corresponding formula-XL PGE-type compound.

EXAMPLE 13

9-[Endo-6-(1,2-dihydroxy-2-methylheptyl)-3-oxobicyclo[3.1.0]hex-2a-yl ] -3-oxa-3,7-inter-m-phenylene-4,5,6-trinor-cis-7-nonenoic Acid Acetonide (Formula-LXXX, Chart G: G is n-pentyl; J' is

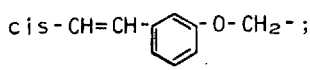

$R_9$ and $R_{26}$ are hydrogen; $R_2$, $R_{11}$, and $R_{12}$ are methyl; and ~ is alpha and endo.

Refer to Chart G. A solution of sodium borohydride (1.5 g.) in 10 ml. of water is added with stirring to a solution of formula-LXXVI dl-methyl 9-[endo-6-(1,2-dihydroxy-2-methylheptyl)-3-oxobicyclo[3.1.0]hex-2a-yl]-3-oxa-3,7-inter-m-phenylene-4,5,6-trinor-cis-7-nonenoate acetonide (5.0 g.) in 110 ml. of absolute ethanol at 0° C. The mixture is stirred for 2.5 hrs. at 0° to 5° C. Then, 40 ml. of acetone is added, and, after 5 min., the mixture is evaporated under reduced pressure. The residue is extracted with dichloromethane, and the extract is washed successively with dilute hydrochloric acid and brine, dried, and concentrated to the formula-LXXVII compound, dl-methyl 9-[endo-6-(1,2-dihydroxy-2-methylheptyl)-3-hydroxybicyclo-[3.1.0] ]hex-2a-yl ]-3-oxa-3,7-inter-m-phenylene-4,5,6-trinor-cis-7-nonenoate acetonide.

This formula-LXXVII cyclic ketal hydroxy ester is dissolved in a mixture of methanol (100 ml.) and 45% aqueous potassium hydroxide solution (30 ml.), and the solution is stirred under nitrogen at 25° C. for 15 hrs. Two volumes of water are then added, and the mixture is acidified with cold hydrochloric acid and then extracted with a mixture of dichloromethane and diethyl ether (1:3). The extract is washed with brine, dried, and concentrated to the formula-LXXVIII compound, dl-9-[endo-6-(1,2-dihydroxy-2-methylheptyl)-3-hydroxybicyclo[3.1.0 ]hex-2a-yl ]-there are obtained the corresponding formula-LXXVII, LXXVIII, and LXXX compounds.

EXAMPLE 14 dl-7-[Endo-6-(1-heptenyl)-3-oxobicyclo[3.1.0]-hex-2a-yl ] -3-oxa-4,7-inter-o-phenylene-5,6-dinor-heptanoic Acid (Formula-LXXXVI, Chart H: G is n-pentyl; Z' is

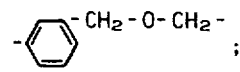

$R_2$, $R_9$, and $R_{26}$ are hydrogen; and ~ is alpha and endo).

Refer to Chart H. Following the procedure of Example 13, the formula-LXXXII compound, dl-ethyl 7-[endo-6-(1-heptenty)-3-oxobicyclo[3.1.0 ]hex-2a-yl ]-3-oxa-4,7-intero-phenylene-5,6-dinor-heptanoate is reduced with sodium borohydride to the formula-LXXXIII compound, dl-ethyl 7-[endo-6-(1-heptenyl)-3-hydroxybicyclo[3.1.0] hex-2a-yl ] -3-oxa-4,7-inter-o-phenylene-5,6-dinor-heptanoate. That hydroxy ester is then saponified as described in Example 13 to the formula-LXXXIV compound, dl-7-[endo-6-(1-heptenyl)-3-hydroxybicyclo[3.1.0 ] hex-2a-yl ] -3-oxa-4,7-intero-phenylene-5,6-dinor-heptanoic acid. That hydroxy acid is then oxidized as described in Example 13 to the title compound.

Following the procedure of Example 14 but substituting for that formula-LXXXII compound, the formula-LXXXII compound of Example 10, viz. dl-methyl 7-

[endo-6-(cis-4-phenyl-1-butenyl)-3-oxobicyclo[3.1.0-]hex-2α-yl] -3-oxa-3,7inter-m-phenylene-4,5,6-trinor-7-nonynoate, there is obtained on reduction the corresponding formula-LXXXIII compound, dl-methyl-7-[endo-6-(cis-4-phenyl-1-butenyl)-3-hydroxybicyclo[3.1.0]hex-2α-yl] -3-oxa-3,7-inter-m-phenylene-4,5,6-trinor-7-nonynoate; there is likewise obtained on saponification the corresponding formula-LXXXIV compound, dl-7-[endo-6-(cis-4-phenyl-1-butenyl)-3-hydroxybicy-3.1.0 ] hex-2α-yl] -3-oxa-3,7-inter-m-phenylene-4,5,6-trinor-7-nonynoic acid; and there is likewise obtained on oxidation the corresponding formula-LXXXVI compound, dl-7-endo-6-(cis-4-phenyl-1-butenyl)-3-oxabicyclo-[3.1.0]hex-2α-yl ] - 3-oxa-3,7-inter-m-phenylene-4,5,6-trinor-7-nonynoic acid.

Following the procedure of Example 14, but using in place of the formula-LXXXII 3-oxobicyclo[3.1.0]hexane ester, each of the specific formula-LXXXII endo and exo, alpha and beta, saturated and acetylenic esters described in and following the Examples 1, 6, and 10 is reduced with sodium borohydride to give the corresponding formula-LXXXIII 3-hydroxy-bicyclo[3.1.0-]hexane ester. That hydroxy ester is then saponified as described in Example 13 to the corresponding formula-LXXXIV 3-hydroxybicyclo-[3.1.0]hexane acid. That hydroxy acid is then oxidized as described in Example 13 to the corresponding formula-LXXXVI 3-oxobicyclo[3.1.0]hexane acid.

EXAMPLE 15 dl-15-Dehydro-3-oxa-3,7-inter-m-phenylene-4,5,6-trinor-PGF$_{1\alpha}$ Methyl Ester (Formula-XCI, Chart J: E' is trans —CH=CH—, G is n-pentyl, J' is

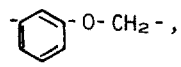

R$_1$ is methyl, R$_{26}$ is hydrogen, and ~ is alpha).

Refer to Chart J. A solution of dl-3-oxa-3,7-inter-m-phenylene-4,5,6-trinor-PGF$_1$ α methyl ester (Example 4, about 0.5 g.) in 24 ml. of dioxane is stirred at 50° C. under nitrogen and 2,3-dichloro-5,6-dicyano-1,4-benzoquinone (0.37 g.) is added. The mixture is stirred at 50° C. for 24 hrs., cooled to room temperature, and filtered. The filter cake is washed with tetrahydrofuran, and the filtrate and wash are combined and concentrated under reduced pressure. The residue is taken up in dichloromethane and washed with brine, then dried over sodium sulfate and concentrated under reduced pressure. The residue is chromatographed over 90 g. of silica gel wet-packed in 8% ethanol in dichloromethane, eluting with 300 ml. of 2%, 300 ml. of 3%, 225 ml. of 7.5% and 245 ml. of 10% ethanol in dichloromethane, taking 15-ml. fractions. Fractions shown by TLC to contain the desired product are combined and concentrated to the title compound.

EXAMPLE 16 dl-15-Methyl-3-oxa-3,7-inter-m-phenylene-4,5,6-trinor-PGF$_{1\alpha}$ Methyl Ester (Formula-XX: C$_q$H$_{2q}$ and C$_p$H$_{2p}$ are valence bonds in meta relationship, G is n-pentyl, Q is

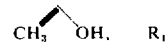

R$_1$ is methyl, and ~ is alpha).

Refer to Chart J. A solution of 0.413 g. of dl-15 dehydro-3-oxa-3,7-inter-m-phenylene-4,5,6-trinor-PGF$_{1\alpha}$ methyl ester (Example 15, about 0.4 g.), hexamethyldisilazane (3 ml.) and trimethylchlorosilane (0.5 ml.) in 20 ml. of tetrahydrofuran is allowed to stand at about 25° C. for 20 hrs. The mixture is filtered and the filtrate is concentrated under reduced pressure. Xylene (10 ml.) is added to the residue and removed by concentration under reduced pressure. The residue is dissolved in anhydrous ether and 110% of the theoretical amount of 3 M methyl magnesium bromide in ether is added. The mixture is allowed to stand 20 min. at about 25° C. and poured into 100 ml. of saturated aqueous ammonium chloride. The ether layer is separated, the aqueous layer is extracted with ether, and the ether extracts are combined and washed with brine, dried over sodium sulfate, and concentrated under reduced pressure. The residue is dissolved in 300 ml. of ethanol and 30 ml. of water containing 3 drops of glacial acetic acid, and the mixture is stirred for 2 hrs. at about 25° C. The mixture is concentrated under reduced pressure to an aqueous residue and the residue is extracted with dichloromethane. The dichloromethane extract is concentrated under reduced pressure to give a residue which is chromatographed over 60 g. of silica gel wet-packed in 8% ethanol in dichloromethane, eluting with 200 ml. of 5% and 800 ml. of 10% ethanol in dichloromethane and taking 10-ml. fractions. Fractions shown by TLC to contain the desired product are combined and concentrated to yield the title compound. Other fractions yield the 15-epimer.

Likewise, using the corresponding 3-oxa-4,7-inter-o-phenylene-5,6-dinor-PGF$_{1\alpha}$ or PGF$_{1\beta}$ compound instead of the above oxa-phenylene compounds, there are obtained the corresponding 15-dehydro PGF$_1$ α or PGF$_1$ β -type compounds, and finally the dl-15-methyl-3-oxa-4,7-inter-o-phenylene-5,6-dinor-PGF$_1$ α or -PGF$_{1\beta}$ ethyl esters and their 15-epimers.

EXAMPLE 17 dl-13,14-Dihydro-3-oxa-3,7-inter-m-phenylene-4,5,6-trinor-PGE$_1$ Methyl Ester (Formula XIX C$_q$H$_{2q}$ and C$_p$H$_{2p}$ are valence bonds in meta relationship, G is n-pentyl, Q is

R$_1$ is methyl, and ~ is alpha).

Refer to Chart B. A solution of dl-3-oxa-3,7-inter-m-phenylene-4,5,6-trinor-PGE$_1$ methyl ester (Example 3, 100 mg.) in 10 mg. of ethyl acetate is shaken with hydrogen at about one atmosphere pressure at 25° C. in the presence of 5% rhodium on charcoal (15 mg.). After approximately one equivalent of hydrogen is absorbed, the hydrogenation is stopped, and the catalyst is removed by filtration. The filtrate is concentrated, aand the residue is chromatographed on 25 g. of silica gel, eluting with 50–100% ethyl acetate gradient in Skellysolve B. Those fractions shown by TLC to contain the desired product free of the starting product and hydrogenolysis products are combined and concentrated to the title compound.

Following the procedure of Example 17, dl-3-oxa-3,7-m-phenylene-4,5,6-trinor-PGE$_1$ methyl ester is reduced to dl-13,14-dihydro-3-oxa-3,7-m-phenylene-4,5,6-trinor-PGE$_1$ ethyl ester. Likewise, dl-3-oxa-4,7-o-phenylene-5,6-dinor-PGE$_1$ methyl ester is reduced to dl-13,14-dihydro-3-oxa-4,7-o-phenylene-5,6-dinor-PGE$_1$ methyl ester.

Also following the procedure of Example 17, dl-3-oxa-3,7-m-phenylene-4,5,6-trinor-PGE$_2$, -trans-5,6-dehydro-PGE$_1$, and -5,6-dehydro-PGE$_2$ are each reduced to dl-13,14-dihydro-3-oxa-3,7-m-phenylene-4,5,6-trinor-PGE$_1$, using two equivalents of hydrogen for the first two reactions, and three equivalents of hydrogen for the third. Likewise, the corresponding dl-3-oxa-4,7-o-phenylene-5,6-dinor- compounds are reduced to dl-13,-14,-dihydro-3-oxa-4,7-o-phenylene-5,6-dinor-PGE$_1$.

Also following the procedure of Example 17, the ethyl ester and the free acid form of the formula XVI-to -XVIII PGE compounds in their various spatial configurations are transformed to the corresponding 13,14-dihydro PGE$_1$ compound by catalytic hydrogenation, using equivalents of hydrogen appropriate to the degree of unsaturation of the reactant, i.e., one equivalent for the PGE$_1$ type, two equivalents for the PGE$_2$ type and trans-5,6-dehydro-PGE$_1$ type, and three equivalents for the 5,6-dehydro-PGE$_2$ type.

Also following the procedure of Example 17, dl-3-oxa-3,7-m-phenylene-4,5,6-trinor-PGF$_{1\alpha}$ and its ethyl ester are reduced to dl-13,14-dihydro-3-oxa-3,7-m-phenylene-4,5,6-PGF$_{1\alpha}$ and its ethyl ester, respectively.

Also following the procedure of Example 17, the ethyl ester and the free acid form of the formula-XX to -XXII PGF compounds in their various spatial configurations are transformed to the corresponding 13,14-dihydro PGF$_{1\alpha}$ or PGF$_{1\beta}$ compound by catalytic hydrogenation, using equivalents of hydrogen appropriate to the degree of unsaturation of the reactant.

EXAMPLE 18 dl-13,14-Dihydro-3-oxa-3,7-inter-m-phenylene-4,5,6-trinor-PGF$_1$ (Formula-XXVII: C$_o$H$_{2o}$ and C$_p$H$_{2p}$ are valence bonds in meta relationship, G is n-pentyl, Q is

R$_1$ is hydrogen, and $\sim$ is alpha).

Refer to Chart B. A suspension of disodium azodiformate (50 mg.) in 5 ml. of absolute ethanol is added to a stirred solution of 3-oxa-3,7-inter-m-phenylene-4,5,6-trinor-PGA$_1$ (Example 5, 50 mg.) in 10 ml. of absolute ethanol under nitrogen at 25° C. The mixture is made acid with glacial acetic acid, and then is stirred under nitrogen at 25° C. for 8 hrs. The resulting mixture is concentrated under reduced pressure, and the residue is mixed with a mixture of diethyl ether and water (1:1). The diethyl ether layer is separated, dried, and concentrated to the title product.

Following the procedure of Example 18, dl-3-oxa-3,7-inter-m-phenylene-4,5,6-trinor-PGA$_1$ methyl ester is reduced to dl-13,14-dihydro-3-oxa-3,7-inter-m-phenylene-4,5,6-trinor-PGA$_1$ methyl ester.

Also following the procedure of Example 18, dl-3-oxa-3,7-inter-m-phenylene-PGA$_2$, -trans-5,6-dehydro-PGA$_1$, and 5,6-dehydro-PGA$_2$ are each reduced to dl-13,14-dihydro-3-oxa-3,7-inter-m-phenylene-4,5,6-trinor-PGA$_1$, using amounts of the disodium azodiformate reactant appropriate to the degree of unsaturation of the reactant.

Also following the procedure of Example 18, the methyl ester and the free acid form of the formula-XVI to -XVIII PGE type compounds, the formula-XX to -XXII PGF type compounds, the formula-XXIV to -XXVI PGA type compounds, and the formula-XXVIII to -XXX PGB type compounds are transformed to the corresponding 13,14-dihydro PGE$_1$, PGF$_1$, PGA$_1$, or PGB$_1$ type compound by diimide reduction, using amounts of disodium azodiformate reactant appropriate to the degree of unsaturation of the PGE, PGF, PGA, or PGB type reactant.

EXAMPLE 19 dl-3-oxa-3,7-inter-m-phenylene-4,5,6-trinor-PGA$_1$ Methyl Ester (Formula-XXIV: C$_o$H$_{2o}$ and C$_p$H$_{2p}$ are valence bonds in meta relationship, G is n-pentyl, Q is

R$_1$ is methyl, and $\sim$ is alpha).

Refer to Chart D. A solution of the formula-XXXIX bismesylate, dl-methyl 7-[endo-6-(1,2-dimesyloxyheptyl)-3-oxobicyclo[3.1.0] hex-2$\alpha$-yl] -3-oxa-3,7-inter-m-phenylene-4,5,6-trinor-heptanoate (Example 3, about 10 g.) in 75 ml. of acetone is mixed with 10 ml. of water and 20 ml. of saturated aqueous sodium bicarbonate solution. The mixture is refluxed under nitrogen for 4 hrs. Then, the mixture is cooled, acidified with 5% hydrochloric acid, and extracted with ethyl acetate. The extract is washed with brine, dried, and concentrated to give the title product.

Following the procedure of Example 19, each of the bismesylates defined in Example 3 is transformed to the corresponding PGA-type ester, including the $\beta,\beta,\beta$-trichloroethyl esters. Thereafter, each of the $\beta,\beta,\beta$-trichloroethyl esters is transformed to the corresponding PGA-type free acid by the procedure of Example 23, below.

EXAMPLE 20 dl-3-oxa-3,7-inter-m-phenylene-4,5,6-trinor-PGB$_1$(Formula-XXVIII: C$_o$H$_{2o}$ and C$_p$H$_{2p}$ are valence bonds in meta relationship, G is n-pentyl, Q is

R$_1$ is hydrogen, and $\sim$ is alpha).

Refer to Chart A. A solution of dl-3-oxa-3,7-inter-m-phenylene-4,5,6-trinor-PGE$_1$ (200 mg.) in 100 ml. of 50% aqueous ethanol containing about one gram of potassium hydroxide is kept at 25° C. for 10 hrs. under nitrogen. Then, the solution is cooled to 10° C. and neutralized by addition of 3 N. hydrochloric acid at 10° C. The resulting solution extracted repeatedly with ethyl acetate, and the combined ethyl acetate extracts are washed with water and then with brine, dried, and concentrated to give the title compound.

Following the procedure of Example 20, dl-3-oxa-3,7-inter-m-phenylene-4,5,6-trinor-PGA$_1$ is also transformed to the PGB$_1$-type title compound.

Following the procedure of Example 20, each of the formula XVI-to -XIX PGE compounds and formula XXIV-to -XXVII PGA compounds are transformed to the corresponding PGB compounds.

EXAMPLE 21 dl-15-Methyl-3-oxa-3,7-inter-m-phenylene-4,5,6-trinor-PGE$_1$ Methyl Ester (Formula XVI: C$_q$H$_{2q}$ and C$_p$H$_{2p}$ are valence bonds in meta relationship, G is n-pentyl; Q is

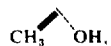

R$_1$ is methyl, and ~ is alpha).

Refer to Chart I. A solution of dl-15-methyl-3-oxa3,7-inter-m-phenylene-4,5,6-trinor-PGF$_1$ $\alpha$ methyl ester (95 mg.) in 40 ml. of acetone is cooled to −10° C. To it is added 110% of the theoretical amount of Jones reagent (in the proportions of 21 g. of chromic anhydride, 60 ml. of water, and 17 ml. of concentrated sulfuric acid), precooled to 0° C., with vigorous stirring. After about 10 min., isopropyl alcohol (1 ml.) is added to the cold reaction mixture. After 5 min., the mixture is filtered and the filtrate is concentrated at reduced pressure, and the residue is mixed with 5 ml. of brine. The mixture is extracted repeatedly with ethyl acetate, and the combined extracts are washed with brine, dried with anhydrous sodium sulfate, and concentrated at reduced pressure. The residue is chromatographed on 20 g. of neutral silica gel, eluting with 50% ethyl acetate in Skellysolve B. Concentration of the eluates gives the title product.

Following the procedure of Example 21, there is substituted for the dl-15-methyl-3-oxa-3,7-inter-m-phenylene-4,5,6-trinor-PGF$_1$ $\alpha$ methyl ester, the free acid, the propyl ester, the octyl ester, the cyclopentyl ester, the benzyl ester, the phenyl ester, the 2,4-dichlorophenyl ester, the 2-tolyl ester, of the $\beta,\beta,\beta$-trichloroethyl ester, there is obtained the corresponding dl-15-methyl-3-oxa-3,7-inter-m-phenylene-4,5,6-trinor-PGE$_1$ compound.

Following the procedure of Example 21, but substituting for the 15-methyl-3-oxa-3,7-inter-m-phenylene-4,5,6-trinor-PGF$_1$ $\alpha$ methyl ester, the methyl ester of each of the 15-methyl-3-oxa-3,7-inter-m-phenylene-4,5,6-trinor-PGF$_1$ $\beta$ , -PGF$_2$ $\alpha$ , -PGF$_2$ $\beta$ , -5,6-dehydro-PGF$_2$ $\alpha$ , -5,6-dehydro-PGF$_2$ $\beta$ , -dihydro-PGF$_1$ $\alpha$ , and -dihydro-PGF$_1$ $\beta$ compounds in their various natural or 15-epi configurations and optical isomers is transformed to the corresponding PGE-type compound.

Following the procedure of Example 21, each of the various 15-alkyl-3-oxa-3,7-inter-m-phenylene-4,5,6-trinor-PGF$_1$ $\alpha$ methyl ester compounds, including the 15-ethyl, 15 propyl, 15-butyl, and 15-substituted isomeric forms of propyl and butyl, is transformed to the corresponding PGE type compound.

Also following the procedure of Example 21, each of the 15-alkyl PGF-type acids and esters within the scope of formula-LXXXVIII (Chart I) is transferred to a 15-alkyl PGE-type acid or ester encompassed by formula-LXXXIX.

EXAMPLE 22 dl-15-Methyl-3-oxa-4,7-inter-o-phenylene-5,6dinor-PGA$_1$ Methyl Ester (Formula XXIV: C$_q$H$_{2q}$ is a valence bond, C$_p$H$_{2p}$ is methylene, C$_q$H$_{2q}$ and C$_p$H$_{2p}$ are in ortho relationship, G is n-pentyl, Q is

R$_1$ is methyl, and ~ is alpha).

Refer to Chart K. A mixture of the formula-XCV 15-methyl-3-oxa-4,7-inter-o-phenylene-5,6-dinor-PGE$_1$ methyl ester (Example 21, 6 mg.), dicyclohexylcarbodiimide (20 mg.), copper (II) chloride dihydrate (2 mg.), and diethyl ether (2 ml.) is stirred under nitrogen at 25° C. for 16 hrs. Then, additional dicyclohexylcarbodiimide (20 mg.) is added, and the mixture is stirred an additional 32 hrs. at 25° C. under nitrogen. The resulting mixture is filtered, and the filtrate is concentrated under reduced pressure. The residue is chromatographed by preparative thin layer chromatography with the A-IX system to give the title compound.

Following the procedure of Example 22, but substituting for the oxa-phenylene PGE$_1$ compound, the methyl esters of dl-15-methyl-3-oxa-4,7-inter-o-phenylene-5,6-dinor-PGE$_2$, -5,6-dehydro-PGE$_2$, and -dihydro-PGE$_1$, there are obtained the corresponding formula-XCVI compounds, viz., the methyl esters of dl-15-methyl 3-oxa-4,7-inter-o-phenylene-5,6-dinor-PGA$_2$, -5,6-dehydro-PGA$_2$, and -dihydro-PGA$_1$.

Also following the procedure of Example 22, but substituting for the phenyl-substituted PGE$_1$ compound, the methyl esters of dl-15-methyl-3-oxa-3,7-inter-m-phenylene-4,5,6-trinor-PGE$_1$, -PGE$_2$, -5,6-dehydro-PGE$_2$, and -dihydro-PGE$_1$, there are obtained the corresponding formula-XCVI compounds, viz., the methyl esters of dl-15-methyl-3-oxa-3,7-inter-m-phenylene-4,5,6-trinor-PGA$_1$, -PGA$_2$, -5,6-dehydro-PGA$_2$, and -dihydro-PGA$_1$.

Also following the procedure of Example 22, each of the formula-XCV (Chart K) compounds defined above in Example 21 is transformed to the corresponding formula-XCVI compound.

EXAMPLE 23 dl-3-Oxa-3,7-inter-m-phenylene-4,5,6-trinor-PGE$_1$ (Formula XVI: C$_q$H$_{2q}$ and C$_p$H$_{2p}$ are valence bonds in metal relationship, G is n-pentyl, Q is

R$_1$ is hydrogen, and ~ is alpha).

Zinc dust (420 mg.) is added to a solution containing dl-3-oxa-3,7-inter-m-phenylene-4,5,6-trinor-PGE$_1$ $\beta,\beta,\beta$-trichloroethyl ester (100 mg.) in 5 ml. of a mixture of acetic acid and water (9:1 v/v). This mixture is stirred under nitrogen 2 hrs. at 25° C. Ethyl acetate (4 volumes) is then added, followed by addition of 1 N. hydrochloric acid (one volume). The ethyl acetate later is separated, washed with water and then with brine, dried, and evaporated. The residue is chromatographed on 15 g. of acidwashed silica gel (Silicar CC4), being eluted with 100 ml. of 50%, 100 ml. of 80%, and 200 ml. of 100% ethyl acetate in Skellysolve B, collecting 20-ml. fractions. The fractions containing the desired product and no starting material or dehydration products as shown by TLC are combined and concentrated to the title compound.

Following the procedure of Example 23, each of the $\beta,\beta,\beta$-tribromoethyl, -triiodoethyl, $\beta,\beta$-dibromoethyl, -diiodoethyl, and the $\beta$-iodoethyl esters of dl-3-oxa-3,7-inter-m-phenylene-4,5,6-trinor-PGE$_1$ is converted to the free acid of dl-3-oxa-3,7-inter-m-phenylene-4,5,6-trinor-PGE$_1$ by reaction with zinc dust and acetic acid.

Following the procedure of Example 23, the $\beta,\beta,\beta$trichloroethyl ester of dl-15-methyl-3-oxa-3,5-inter-m-phenylene-4-nor-PGE$_2$ following Example 9 above is converted to the respective free acid compound using zinc dust with either propionic, butyric, pentanoic, or hexanoic acid instead of acetic acid.

Following the procedure of Example 23, the $\beta,\beta,\beta$-trichloroethyl ester of each of the PGE, PGF, PGA, and PGF type compounds represented by formulas XVI-XXXV in their various structural configurations and optical isomers is treated with zinc dust and acetic acid to obtain the corresponding free acid form of the compound. The esters are prepared by the procedures disclosed herein, using as intermediates formula-XXXVII cyclic ketals or formula-XLIV or -LXX olefins wherein R$_{10}$ is haloethyl, e.g., $\beta,\beta,\beta$-trichloroethyl. These intermediates are prepared either by alkylation of the respective formula-XXXVI cyclic ketal (Chart D) or formula-XLIII or -LXIX olefin (Charts E and F) with the appropriate alkylating agent wherein R$_{10}$ is haloethyl, or by the transformation of the alkylated cyclic ketal or olefin by the steps shown in Charts G and H using procedures disclosed herein, yielding intermediates LXXIX, LXXXI, LXXXV, or LXXXVII.

EXAMPLE 24 dl-3-Oxa-3,7-inter-m-phenylene-4,5,6-trinor-PGF$_1$ $\alpha$ and -PGF$_1$ $\beta$ (Formula XX; C$_o$H$_{2o}$ and C$_p$H$_{2p}$ are valence bonds in meta relationship, G is n-pentyl, Q is

R$_1$ is hydrogen, and $\sim$ is alpha or beta).

A solution of 146 mg. of dl-3-oxa-3,7-inter-m-phenylene-4,5,6-trinor-PGF$_1$ $\alpha$ ethyl ester in a mixture of 4.5 ml. of methanol and 1.5 ml. of water is cooled to 5° C. and 0.6 ml. of 45% aqueous potassium hydroxide is added. The mixture is allowed to stand 3.5 hrs. at 25° C., then is diluted with 75 ml. of water and extracted once with ethyl acetate to remove any neutral material. The aqueous layer is separated, made acid with dilute hydrochloric acid and extracted 4 times with ethyl acetate. The extracts are combined and washed 3 times with water, once with brine, dried over sodium sulfate, and concentrated to give the PGF$_1$ $\alpha$ -type title compound.

Following the procedure of Example 24, the methyl ester of dl-3-oxa-3,7-inter-m-phenylene-4,5,6-trinorPGF$_1$ $\beta$ is transformed to the free acid, i.e. the formula-XX PGF$_1$ $\beta$ -type title compound.

Following the procedure of Example 24, the methyl or ethyl esters of the various oxa-phenylene PGF-type compounds and their isomers are transformed to the corresponding free-acid oxa-phenylene PGF-type compounds.

EXAMPLE 25 dl-3-Oxa-3,5-inter-m-phenylene-4-nor-PGF$_2$ $\alpha$ Methyl Ester (Formula XXI: C$_j$H$_{2j}$ and C$_p$H$_{2p}$ are valence bonds in meta relationship, G is n-pentyl, Q is

R$_1$ is methyl, R$_3$ and R$_4$ are hydrogen, and $\sim$ is alpha).

Refer to Chart C. dl-5,6-Dehydro-3-oxa-3,5-inter-m-phenylene-4-nor-PGF$_2$ $\alpha$ methyl ester (200 mg.) in pyridine (4 ml.) and methanol (10 ml.) is hydrogenated in the presence of a 5%-palladium-on-barium sulfate catalyst (200 mg.) at 25° and atmospheric pressure. The reaction is terminated when slightly more than one equivalent of hydrogen is absorbed. The mixture is filtered and evaporated. Ethyl acetate is added and residual pyridine is removed by addition of ice and 3 N. hydrochloric acid. The ethyl acetate layer is washed with 1 N. hydrochloric acid and then with brine, dried, and concentrated to yield the title product.

Following the procedure of Example 25, the 5,6-dehydro oxa-phenylene PGF$_2$ compounds following Example 4 are reduced to the corresponding PGF$_2$ compounds. Likewise, the 5,6-dehydro oxa-phenylene PGE, PGA, and PGB compounds disclosed herein are reduced to the corresponding PGE$_2$, PGA$_2$, and PGB$_2$ compounds.

EXAMPLE 26 dl-$\beta,\beta,\beta$-Trichloroethyl 9-[endo-6-(1,2-dihydroxy-2-methylheptyl)-3-hydroxybicyclo[3.1.0]-hex-2$\alpha$-yl]-3-oxa-3,7-inter-m-phenylene-4,5,6trinor-cis-7-nonenoate Acetonide (Formula LXXIX, Chart G: G is n-pentyl, J' is cis

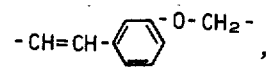

haloethyl is $\beta,\beta,\beta$-trichloroethyl, R$_2$, R$_{11}$, and R$_{12}$ are methyl, R$_9$ and R$_{26}$ are hydrogen, and $\sim$ is alpha and endo).

Refer to chart G. Successively, $\beta,\beta,\beta$-trichloroethanol (25 ml.), pyridine (15 ml.), and dicyclohexylcarbodiimide (4.0 g.) are added to a solution of formula-LXXVIII compound dl-9-[endo-6-(1,2-dihydroxy-2-methylheptyl)-3-hydroxybicyclo[3.1.0]hex-2$\alpha$-yl]-3-oxa-3,7-inter-m-phenylene-4,5,6-trinor-cis-7-nonenoic acid acetonide (Example 13, 2.0 g.) in 100 ml. of dichloromethane. This mixture is stirred 3 hrs. under nitrogen at 25° C. Water (50 ml.) is then added, and the mixture is stirred 10 min. The dichloromethane is concentrated under reduced pressure, and the residue is extracted repeatedly with ethyl acetate. The combined extracts are washed with ice-cold 3 N. hydrochloric acid. Then, the extracts are washed successively with aqueous sodium bicarbonate solution and

139 brine, dried, and concentrated under reduced pressure. The residue is chromatographed on 600 g. of silica gel, eluting with 10 l. of a 20–100% ethyl acetate-Skellysolve B gradient, collecting 50ml. fractions. The middle fractions which show a product free of starting materials on TLC are combined and concentrated under reduced pressure to give the title compound.

Following the procedure of Example 26, but using in place of the formula-LXXVIII 3-hydroxybicyclo[3.1.0-]hexane acid acetonide, each of the specific endo and exo, alpha and beta, saturated and unsaturated formula-LXXVIII hydroxy acid ketals defined after Example 13, there are obtained the corresponding $\beta,\beta,\beta$-trichloroethyl esters of those 3-hydroxybicyclo[3.1.0-]hexane acids.

Following the procedure of Example 26, but using in place of the formula-LXXVIII 3-hydroxybicyclo[3.1.0-]hexane acid ketal, each of the specific formula-LXXX 3-oxo-acid ketals defined after Example 13, there are obtained the corresponding formula-LXXXI $\beta,\beta,\beta$-trichloroethyl esters of those 3-oxo-acid ketals.

Following the procedure of Example 26 but using in place of the formula-LXXVIII 3-hydroxy-acid ketal, each of the specific formula-LXXXIV (Chart H) 3-hydroxy and formula-LXXXVI 3-oxo acids defined after Example 14, there are obtained the corresponding formula-LXXXV and formulaLXXXVII $\beta,\beta,\beta$-trichloroethyl esters of those acids, respectively.

Following the procedures of Examples 3 and 9, each of the formula-LXXXI cyclic ketal haloethyl esters of Example 26 is transformed to the corresponding formula-XL (Chart D) 3-oxa or 4-oxa phenyl-substituted $PGE_1$ $\beta,\beta,\beta$-trichloroethyl ester. Thence, following the procedure of Example 23, each of the esters is transformed to the oxaphenylene $PGE_1$ acid compound wherein $R_{10}$ of formula-XL is replaced with hydrogen.

Following the procedure of Examples 2 and 3 each of the formula-LXXXVII olefin haloethyl esters of Example 26 is transformed to the corresponding formula-XLVII (Chart E) oxa-phenylene $PGE_1$ $\beta,\beta,\beta$-trichloroethyl ester. Thence, following the procedure of Example 23, each of the esters is transformed to the corresponding $PGE_1$-type acid compound wherein $R_{10}$ of formula-XL is replaced with hydrogen.

EXAMPLE 27 dl-3-Oxa-3,7-inter-m-phenylene-4,5,6-trinor-$PGA_1$ Methyl Ester (Formula XXIV: $C_qH_{2q}$ and $C_pH_{2p}$ are valence bonds in meta relationship, G is n-pentyl, Q is

H⁄ \OH, $R_1$ is methyl, and ~ is alpha).

A solution of diazomethane (about 50% excess) in diethyl ether (25 ml.) is added to a solution of dl-3-oxa-3,7-inter-m-phenylene-4,5,6-trinor-p$GA_1$ (Example 5, 50 mg.) in 25 ml. of a mixture of methanol and diethyl ether (1:1). The mixture is allowed to stand at 25° C. for 5 min. Then the mixture is concentrated to give the title compound.

Following the procedure of Example 27, each of the other specific phenyl-substituted PGB type, PGA type, PGE type, and PGF type free acids defined above is converted to the corresponding methyl ester.

140

Also following the procedure of Example 27, but using in place of the diazomethane, diazoethane, diazobutane, 1-diazo-2-ethylhexane, and diazocyclohexane, there are obtained the corresponding ethyl, butyl, 2-ethylhexyl, and cyclohexyl esters of 3-oxa-3,7-inter-m-phenylene-4,5,6-trinor-$PGA_1$. In the same manner, each of the other specific phenyl-substituted PGB type, PGA type, PGE type, and PGF type free acids defined above is converted to the corresponding ethyl, butyl, 2-ethylhexyl, and cyclohexyl esters.

EXAMPLE 28 dl-3-Oxa-3,7-inter-m-phenylene-4,5,6-trinor-$PGE_1$ Methyl Ester Diacetate.

Acetic anhydride (5 ml.) and pyridine (5 ml.) are mixed with dl-3-oxa-3,7-inter-m-phenylene-4,5,6-trinor-$PGE_1$ methyl ester (Example 3, 20 mg.), and the mixture is allowed to stand at 25° C. for 18 hrs. The mixture is then cooled to 0° C., diluted with 50 ml. of water, and acidified with 5% hydrochloric acid to pH 1. That mixture is extracted with ethyl acetate. The extract is washed successively with 5% hydrochloric acid, 5% aqueous sodium bicarbonate solution, water, and brine, dried and concentrated to give the title compound.

Following the procedure of Example 28 but replacing the acetic anhydride with propionic anhydride, isobutyric anhydride, and hexanoic acid anhydride, there are obtained the corresponding dipropionate, diisobutyrate and dihexanoate derivatives of dl-3-oxa-3,7-inter-m-phenylene-4,5,6-trinor-$PGE_1$ methyl ester.

Also following the procedure of Example 28, but replacing the 3-oxa-3,7-inter-m-phenylene-4,5,6-trinor-$PGE_1$ compound with dl-3-oxa-3,7-inter-m-phenylene-4,5,6-trinor-$PGF_{1\alpha}$ and -$PGF_1\beta$, and dl-15-methyl-3-oxa-3,7-inter-m-phenylene-4,5,6-trinor-$PGF_{1\alpha}$ and -$PGF_1\beta$, there are obtained the corresponding triacetate derivatives of the 3-oxa-3,7-inter-m-phenylene-4,5,6-trinor-PGF compounds.

Also following the procedure of Example 28, each of the phenyl-substituted PGE type, PGF type, PGA type, and PGB type esters and free acids defined above is transformed to the corresponding acetates, propionates, isobutyrates, and hexanoates, the PGE-type derivatives being dicarboxyacylates, the PGF-type derivatives being tricarboxyacylates, and the PGA-type and PGB-type derivatives being monocarboxyacylates.

EXAMPLE 29 dl-3-Oxa-3,7-inter-m-phenylene-4,5,6-trinor-$PGE_1$ Sodium Salt.

A solution of dl-3-oxa-3,7-inter-m-phenylene-4,5,6-trinor-$PGE_1$ (Example 23, 100 mg.) in 50 ml. of a waterethanol mixture (1:1) is cooled to 5° C. and neutralized with an equivalent amount of 0.1 N, aqueous sodium hydroxide solution. The neutral solution is concentrated to give the title compound.

Following the procedure of Example 29 but using potassium hydroxide, calcium hydroxide, tetramethylammonium hydroxide, and benzyltrimethylammonium hydroxide in place of sodium hydroxide, there are obtained the correspondence salts of dl-3-oxa-3,71-inter-m-phenylene-4,5,6-trinor-$PGE_1$.

Also following the procedure of Example 29 each of the phenyl-substituted PGE type, PGF type, PGA type, and PGB type acids defined above is transformed to the sodium, potassium, calcium, tetramethylammonium, and benzyltrimethylammonium salts.

The various Preparations and Examples given above describe the preparation of racemic intermediates and final products. Each of the intermediates and final products named and defined above is also obtained in each of the enantiomeric forms, d and l, by resolution that compound or by resolution of an intermediate used to prepare that compound. For example, natural configuration 3-oxa-3,7-inter-m-phenylene-4,5,6-trinor-PGA$_1$ free acid is prepared by resolution of dl-3-oxa-3,7-inter-m-phenylene-4,5,6-trinor-PGA$_1$ free acid (Example 5) or by dehydration as in Example 5 of optically active 3-oxa-3,7-inter-m-phenylene-4,5,6-trinor-PGE$_1$ free acid with the same absolute configuration. These resolutions are carried out by procedures known in the art, and may be used to obtain prostaglandin-like materials having the spatial configuration of the natural prostaglandins, as typified by the following Examples 30–32.

EXAMPLE 30

Natural Configuration
3-oxa-3,5-inter-m-phenylene-4-nor-PGE$_2$ and PGF$_{2\alpha}$ Methyl Esters (Formula-XVII and -XXI: wherein C$_j$H$_{2j}$ and C$_p$H$_{2p}$ are valence bonds in meta relationship, G is n-pentyl, Q is

R$_1$ is methyl; R$_3$ and R$_4$ are hydrogen; and ~ is alpha).

The process shown in Chart D is used to prepare the PGE$_2$-type compound first. The formula-XXXVII cyclic ketal intermediate wherein G is n-pentyl; J' is

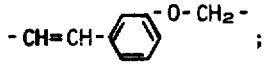

R$_2$, R$_9$, and R$_{26}$ are hydrogen; R$_{10}$, R$_{11}$, and R$_{12}$ are methyl; and ~ is endo and alpha is prepared following the procedures of Example 9.

The formula-XXXVII compound is resolved as its optical isomers by the method of Corey et al., J. Am. Chem. Soc. 84, 2938 (1962), by reacting this keto compound with optically active L(+)-2,3-butanedithiol in the presence of p-toluene-sulfonic acid. The diastereomeric ketals are completely resolved on a preparative chromatographic column, and are then hydrolyzed separately, following the procedure of Example 9, to the formula-XXXVIII dihydroxy compounds. Transformation to the formula-XVII PGE$_2$-type compounds is accomplished by the procedures of Example 3. Of the separate diastereoisomers, one corresponds to the configuration of natural PGE$_2$ and the other to its enantiomer. Conversion of the PGE$_2$-type compound having the configuration of the natural product to the PGF$_{2\alpha}$-type methyl ester is done by borohydride reduction following the procedure of Example 4. The natural configuration-PGF$_{2\alpha}$-type free acid is formed from the methyl ester by saponification, following the procedure of Example 24.

EXAMPLE 31

Natural Configuration
3-oxa-3,5-inter-o-phenylene-4-nor-PGE$_1$ Methyl Ester (Formula XVI: C$_o$H$_{2o}$ is ethylene; C$_p$H$_{2p}$ is a valence bond in ortho relationship to C$_o$H$_{2o}$, G is n-pentyl, Q is

R$_1$ is methyl, and ~ is alpha).

Refer to Chart E. A. Methyl 7-[endo-6-(1-heptenyl)-3-oxobicyclo-[3.1.0]hex-2α-yl]-3-oxa-3,5-inter-o-phenylene-4-nor-heptanoate (Formula-XLIV, Chart E: G is n-pentyl; R$_2$, R$_9$, and R$_{26}$ are hydrogen; R$_{10}$ is methyl; Z' is

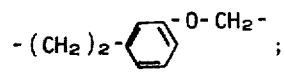

and ~ is alpha and endo).

1. Methyl 2-(3-hydroxypropyl)phenoxyacetate. To a solution of potassium t-butoxide (11.2 g.) in 150 ml. of dry tetrahydrofuran at 0°–5° C. is added with stirring 3-(o-hydroxyphenyl)propanol (15.2 g.) followed in a few minutes by methyl bromoacetate (20 g.). The cooling bath is removed and the mixture is stirred at ambient temperature until the reaction mixture becomes essentially neutral. The mixture is concentrated in vacuo at 30° C. and the residue is shaken with ether and water. The organic layer is washed with dilute potassium hydroxide solution, water, brine, and is dried over sodium sulfate and then concentrated in vacuo. The residue is distilled in a high vacuum to afford methyl 2-(3-hydroxypropyl)phenoxyacetate. 2. Methyl 2-(3-chloropropyl)phenoxyacetate. A mixture of methyl 2-(3-hydroxypropyl)phenoxyacetate (step A-1, 25 g.) and thionyl chloride (20 ml.) is heated to reflux for 1–2 hrs. The excess thionyl chloride is removed in vacuo and the residue is distilled in a high vacuum to afford methyl 2-(3-chloropropyl)phenoxyacetate. 3. Methyl 2-(3-iodopropyl)phenoxyacetate. A mixture of methyl 2-(3-chloropropyl)phenoxyacetate (step A-2, 24.3 g.), acetone (250 ml.) and sodium iodide (30 g.) is heated to reflux with stirring for about 40 hrs. The mixture is cooled, filtered and the filtrate is concentrated in vacuo at about 30° C. The residue is diluted with ether and the solution is washed with water, dilute sodium thiosulfate solution, brine and is dried over magnesium sulfate and then concentrated in vacuo. The product, methyl 2-(3-iodopropyl)phenoxyacetate, is used directly in the next step. 4. Following the procedure of Example 1-B, but replacing the methyl m-(chloromethyl)phenoxyacetate with methyl 2-(3-iodopropyl) phenoxyacetate (step A-3, 18 g.) and allowing the alkylation reaction to proceed for about 5 min. before acidification with hydrochloric acid, there is obtained the desired formula-XLIV methyl 7-]endo-6-(1-heptenyl)-3-oxobicyclo[3.1.0]hex-2α-yl]-3-oxa-3,5-inter-o-phenylene-4-nor-heptanoate.

Following the procedure of Example 30, the above racemic formula-XLIV compound is resolved as two optically active isomers. These are both transformed by the subsequent steps of this example to the formula-XVI PGE$_1$-type compounds, one of which corresponds to the configuration of natural PGE₁ and the other to its enantiomer.

B. Methyl 7-[endo-6-(1,2-dihydroxyheptyl)-3-oxobicyclo[3.1.0]hex-2α-yl]-3-oxa-3,5-inter-o-phenylene-4-nor-heptanoate (Formula-XLV, Chart E: G' is n-pentyl; $R_2$, $R_9$, and $R_{26}$ are hydrogen; $R_{10}$ is methyl; Z' is

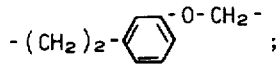

and ~ is alpha and endo). To a solution of methyl 7-[endo-6-(1-heptenyl)-3-oxobicyclo[3.1.0]-hex-2α-yl]-3-oxa-3,5-inter-o-phenylene-4-nor-heptanoate (step A, above, 1.8 g.) in 30 ml. of tetrahydrofuran at 50° is added, with stirring, osmium tetroxide (200 mg.) followed by potassium chlorate (1.2g.) and 15 ml. of water. The reaction mixture is maintained at 50° for 2 hrs., cooled, the tetrahydrofuran is removed, and the aqueous phase is extracted with dichloromethane. The organic layer is dried and concentrated and the residue is chromatographed on 200 g. of silica gel. The column is eluted with 1 l. of 35% ethyl acetate-benzene and 1 l. of 40% ethyl acetate-benzene, collecting 30-ml. fractions. Those fractions containing the formula-XLV compound, in its isomeric erythro and threo forms free of starting material and impurities, are combined and concentrated.

C. Title compound. To a solution of the formula-XLV dihydroxy compound (step B, above, 0.8 g.) in 10 ml. of pyridine, cooled to 0°, is added 1.2 ml. of methane-sulfonyl chloride. The reaction mixture is stirred for 2 hrs. and 20 g. of ice is added. The mixture is extracted with ether-dichloromethane (1:1) and the organic layer is washed successively with dilute hydrochloride acid, water, saturated aqueous sodium bicarbonate, and brine, dried, and concentrated. The residue, containing the bismesylate, is treated with 15 ml. of acetone and 10 ml. of water and stirred for 8-16 hrs. at 25°. The acetone is removed in vacuo and the remaining solution is extracted with dichloromethane. The extract is dried and concentrated and the residue is chromatographed on 150 g. of silica gel using 500 ml. ethyl acetate followed by 3% methanol ethyl acetate as eluting solvent while collecting 30-ml. fractions. Those fractions containing the formula-XLVII product, free of starting material and impurities, are combined and concentrated to give the title compound; principle NMR spectral peaks at 6.57-7.3 (multiplet); 5.42-5.65 (multiplet); 4.60 (singlet) and 3.76 (singlet) δ.

EXAMPLE 32

Natural Configuration
3-Oxa-3,5-inter-o-phenylene-4-nor-PGF₁α Methyl Ester (Formula-XX: $C_oH_{2o}$ is ethylene, $C_pH_{2p}$ is a valence bond in ortho relationship to $C_qH_{2q}$. G is n-pentyl, Q is

$R_1$ is methyl, and ~ is alpha for the carboxyl-containing moiety and for the ring hydroxyl).

Refer to Chart A. Following the procedure of Example 4, the formula-XVI PGE₁-type compound of Example 31 is transformed to the title compound; principle NMR spectral peaks at 6.57-7.3 (multiplet); 5.33-5.56 (multiplet); 4.62 (singlet) and 3.75 (singlet) δ.

EXAMPLE 33 dl-3-Oxa-3,5-inter-m-phenylene-4-nor-PGE₃ Methyl Ester (Formula-XXXII; $C_jH_{2j}$ and $C_pH_{2p}$ are valence bonds in meta relationship, $C_nH_{2n}$ is methylene, Q is

$R_1$ is methyl, $R_5$ is ethyl, and ~ is alpha) and dl-15-Beta-3-oxa-3,5-inter-m-phenylene-4-nor-PGE₃ Methyl Ester

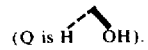

a. Refer to Chart F. Following the procedure of Preparation 4b, a solution of 100 g. of endo-bicyclo-[3.1.0]hexan-3-ol-6-carboxaldehyde 3-tetrahydropyranyl ether in 200 ml. of benzene is reacted with 250 g. of (hex-3-ynyl)triphenylphosphonium bromide (Axen et al., Chem. Comm. 1970, 602) in 3 l. of benzene at about −15° C. The mixture is warmed to 70° C. for 2.5 hours., cooled and filtered. The crude product is hydrolyzed to the 3-hydroxy compound and then oxidized to the 3-oxo ketone with Jones reagent. The desired fromula-LXIX intermediate is isolated after silica gel chromatography.

b. There is next prepared the formula-LXX compound by alkylation. Following the procedures of Example 1-B, the product of step a above is reacted with methyl 9-chloro-3-oxa-3,7-inter-m-phenylene-4,5,6-trinor-7-nonynoate (Preparation 7) to yield 7-[endo-6-(cis-1-hepten-4-ynyl)-3-oxobicyclo[3.1.0]hex-2α-yl]-3-oxa-3,7-inter-m-phenylene-4,5,6-trinor-7-nonynoate.

c. Glycol LXXI is next prepared, employing the product of step b and following the procedures of Example 2. Without separating the isomeric glycols, the bismesylate corresponding to formula-LXXII is then prepared following the procedures of Example 3. Thereafter, following hydrolysis of the bismesylate by the procedures of Example 3, the bisdehydro E₃ type compound corresponding to formula-LXXIII is recovered. Silica gel chromatography yields the respective C-15 epimers.

d. Following the procedures of Preparation 8, each of the C-15 epimers of step C above is hydrogenated to yield the corresponding title compounds.

EXAMPLE 34

1-Bicyclo[3.1.0]hex-2-ene-6-endocarboxaldehyde Neopentyl Glycol Acetal (Formula $c_{IX}$: $R_{31}$ and $R_{32}$ taken together are —CH₂—C(CH₃)₂—CH₂— and ~ is endo).

A mixture of 2,2-dimethyl-1,3-propanediol (900 g.), 5 l. of benzene and 3 ml. of 85% phosphoric acid is heated at reflux. To it is added, in 1.5 hr., a solution of optically active bicyclo[3.1.0]hex-2-ene-6-endo-carboxaldehyde (Prep.10, 500 g.) in one liter of benzene. Provision is made to take off azeotropically distilled water with a Dean-Stark trap. After 3 hr. the mixture is cooled and extracted with 2 liters off 5% sodium bicarbonate. The organic phase is dried over sodium sulfate and concentrated under reduced pressure. The resulting semisolid residue is taken up in methanol and recrystallized, using a total of 1200 ml. of methanol to which 600 ml. of water is added, then chilled to $-13°$ C. to yield 300 g. of the title compound, m.p. $52°-55°$ C., and having NMR peaks at 0.66, 1.20, 0.83–2.65, 3.17–3.8, 3.96, and 5.47–5.88 $\delta$, $[\alpha]_D -227°$ (C=0.8976 in methanol), and $R_f$ 0.60 (TLC on silica gel in 25% ethyl acetate in mixed isomeric hexanes). Further work-up of the mother liquors yields 50–100 g. of additional product.

Following the procedures of Example 34 but replacing the aldehyde with optically active bicyclo[3.1.0-]hex-2-ene-6-exo-carboxaldehyde (see U.S. Pat. No. 3,711,515), there is obtained the corresponding formula-CIX acetal.

Following the procedures of Example 34 but using either the endo or exo form of the aldehyde and substituting for 2,2-dimethyl-1,3-propanediol one of the following glycols: ethylene glycol, 1,2-propanediol, 1,2-hexanediol, 1,3-butanediol, 2,3-pentanediol, 2,4-hexanediol, 2,4-octanediol, 3,5-nonanediol, 3,3-dimethyl-2,4-heptanediol, 4-ethyl-4-methyl-3,5-heptanediol, phenyl-1,2-ethanediol and 1-pentyl-1,2-propanediol, there are obtained the corresponding formula-CIX acetals.

EXAMPLE 35 d-8-(m-Acetoxyphenyl)-7-oxa-tricyclo-[4.2.0.0$^{2,4}$]octane-6-endo-carboxaldehyde Neopentyl Glycol Acetal (Formual CX: $C_pH_{2p}$ is a valence bond with attachment in the meta position, $R_{31}$ and $R_{32}$ taken together are $-CH_2-C(CH_3)_2-CH_2$, $R_{39}$ is

and $\sim$ is endo).

Refer to Chart L, step (a). A solution of the formula-CIX l-bicyclo[3.1.0]hex-2-ene-6-endo-carboxaldehyde neopentyl glycol acetal (Example 34, 5.82 g.) and m-acetoxybenzaldehyde (1.64 g.) in 25 ml. of benzene is charged to a Pyrex photolysis vessel equipped with an immersible water-cooled cold-finger and a fritted gas inlet tube. Dissolved oxygen is removed by bubbling nitrogen through the solution. The mixture is then irradiated at 350 nm. with a Rayonet Type RS Preparative Photochemical Reacter (The Southern New England Ultraviolet Co., Middletown, Conn.) equipped with six RUL 3500 A lamps. After 24 hr. the photolysate is concentrated under reduced pressure to a pale yellow oil, 10 g., which is subjected to silica gel chromatography. Elution with 10–70% ethyl acetate in Skellysolve B (mixture of isomeric hexanes) yields separate fractions of the recovered starting material and the formula-CX title compound, a pale yellow oil, 0.86 g., having NMR peaks at 0.68. 1.20, 0.8–2.5, 2.28, 2.99, 3.12–3.88, 3.48, 4.97–5.52, and 6.78–7.60 $\delta$; infrared absorption bands at 3040, 2950, 2860, 2840, 1765, 1610, 1590, 1485, 1470, 1370, 1205, 1115, 1020, 1005, 990, 790, and 700 cm$^{-1}$; mass spectral peaks at 358, 357, 116, 115, 108, 107, 79, 70, 69, 45, 43, and 41; $[\alpha]_D +55°$ (C=0.7505 in 95% ethanol); and $R_f$ 0.18 (TLC on silica gel in 25% ethyl acetate in mixed isomeric hexanes).

Following the procedures of Example 35 but replacing the formula-CIX acetal with the formula-CIX compounds disclosed following Example 34, there are obtained the corresponding formula-CX compounds in their endo or exo forms and with corresponding exemplification of $R_{31}$ and $R_{32}$.

Likewise following the procedures of Example 35 but replacing m-acetoxybenzaldehyde with aldehydes within the scope of formula CXIX above, as to $C_pH_{2p}$, the attachment position of the phenyl ring, and the carboxyacyl group $R_{39}$, or defined above, the corresponding formula-CX oxetanes are obtained wherein $\sim$ is endo or exo, and $R_{31}$ and $R_{32}$ correspond to the glycols employed after Example 34 above. Specifically, the following formula-CXIX aldehydes are employed:

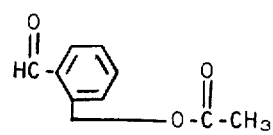

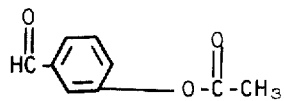

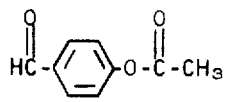

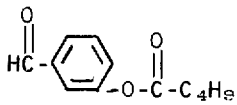

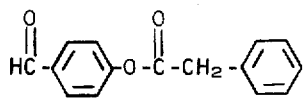

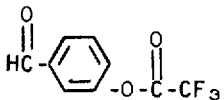

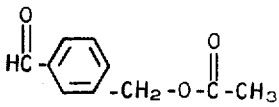

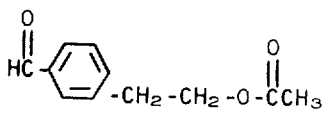

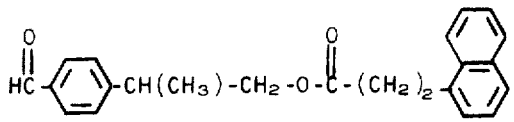

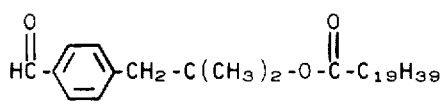

EXAMPLE 36 d-2-Exo-[m-(pivaloyloxy)benzyl]-3-exobicyclo[3.1.0-]hexane-6-endo-carboxaldehyde Neopentyl Glycol Acetal (Formula CXII: $C_pH_{2p}$ is a valence bond with attachment in the meta position, $R_{31}$ and $R_{32}$ taken together are $-CH_2-C(CH_3)_2-CH_2-$, $R_{43}$ is

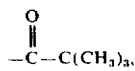

and ~ is endo).

(I). Refer to Chart L, steps (b) and (c). A mixture of lithium (0.25 g.) in 70 ml. of ethylamine is prepared at 0° C. and cooled to −78° C. A solution of the formula-CX d-8-(m-acetoxyphenyl)-7-oxa-tricyclo[4.2.0.0$^{2,4}$]-octane-6-endo-carboxaldehyde neopentyl glycol acetal (Example 35, 1.83 g.) in 10 ml. of tetrahydrofuran is added dropwise in about 5 min. After stirring at −78° C. for about 3.5 hr. the reaction is quenched with solid ammonium chloride and water-tetrahydrofuran. Unreacted lithium is removed, the mixture is warmed slowly to about 25° C., and ethylamine is removed. The residue is neutralized with dilute acetic acid, mixed with 200 ml. of brine, and extracted with ethyl acetate. The organic phase is washed with brine and a mixture of brine and saturated aqueous sodium bicarbonate (1:1), and dried over sodium sulfate. Concentration under reduced pressure yields the formula-CXI diol as a pale tan foamed oil, 1.64 g., having $R_f$ 0.03 (TLC on silica gel in 25% ethyl acetate in mixed isomeric hexanes).

(II). The product of part (I) is dissolved in 30 ml. of pyridine and treated with 1.5 ml. of pivaloyl chloride over a period of 22 hr. at about 25° C. The reaction mixture is mixed with water, then brine and extracted with ethyl acetate. The organic phase is washed successively with brine, water, saturated aqueous copper (II) sulfate, saturated aqueous sodium bicarbonate, and brine, and dried over sodium sulfate. Concentration under reduced pressure yields a residue, 2.53 g., which is subjected to silica gel chromatography to yield the formula-CXII title compound, 1.87 g., having NMR peaks at 0.71, 1.20, 1.33, 0.9–3.1, 3.28–4.00, 4.17, 4.7–5.2, and 6.77–7.53 δ; mass spectral peaks at 486, 485, 115, 73, 72, 57, 44, 43, 42, 41, 30, 29, 15; $[α]_D +10°$ (C=0.8385 in ethanol); and $R_f$ 0.50 (TLC on silica gel in 25% ethyl acetate in mixed isomeric hexanes).

EXAMPLE 37 d-2-Exo-(m-acetoxybenzyl)-3-exo-acetoxybixyclo]3.1.0]hexane-6-endo-carboxaldehyde Neopentyl Glycol Acetal (Formula CXII: $C_pH_{2p}$ is a valence bond with attachment in the meta position, $R_{31}$ and $R_{32}$ taken together are $-CH_2C(CH_3)_2-CH_2-$, $R_{43}$ is

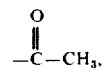

and ~ is endo).

Following the procedure of Example 36-(II) but replacing pivaloyl chloride with acetic anhydride, and using 1.01 g. of the formula-CXI diol, there is obtained the title compound, 0.75 g., having NMR peaks at 0.72, 1.22, 1.98, 2.27, 0.8–3.0, 3.28–3.85, 4.17, 4.75–5.22, and 6.8–7.47 δ; mass spectral peaks at 402, 401, 115, 107, 73, 69, 45, 44, 43, 42, 41, 30; $[α]_D +7°$ (C=0.7060 in ethanol); and $R_f$ 0.66 (TLC on silica gel in 50% ethyl acetate in mixed isomeric hexanes).

EXAMPLE 38

2-Exo-[m-(pivaloyloxy)benzyl]-3-exo-(pivaloyloxy)-bicyclo[3.1.0]hexane-6-endo-carboxaldehyde (Formula CXIII: $C_pH_{2p}$ is a valence bond with attachment in the meta position, $R_{42}$ is

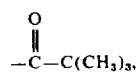

and ~ is endo).

Refer to Chart L step (d). The formula-CXII acetal, i.e. d-2-exo-[m-pivaloyloxy)benzyl]-3-exo-(pivaloyloxy)-bicycly[3.1.0]hexane-6-endo-carboxaldehyde neopentyl glycol acetal (Example 36, 0.48 g.) is treated at 0° C. with 25 ml. of 88% formic acid for 4 hr. The mixture is diluted with 200 ml. of brine and extracted with ethyl acetate. The organic phase is washed with brine and saturated aqueous sodium bicarbonate, and dried over magnesium sulfate. Concentration under reduced pressure yields an oil, 0.55 g., which is subjected to silica gel chromatography. Elution with 5–15% ethyl acetate in Skellysolve B yields the formula-CXIII title compound as an oil, 0.37 g., having NMR peaks at 1.20, 1.33, 0.6–3.2, 5.1–5.5, 6.6–7.5, and 9.73 δ; and $R_f$ 0.50 (TLC on silica gel in 25% ethyl acetate in mixed isomeric hexanes).

EXAMPLE 39

2-Exo-[m-(pivaloyloxy)benzyl]-3-exo-(pivaloyloxy)-6-endo-(cis-1-heptenyl)-bicyclo[3.1.0]hexane (Formula CXIV: $C_pH_{2p}$ is a valence bond with attachment in the meta position, G is n-pentyl, $R_{42}$ is

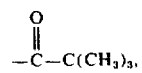

R$_2$ is hydrogen, and ~ is endo); and
2-Exo-(m-hydroxybenzyl)-3-exo-hydroxy-6-endo-(cis-1-heptenyl)bicyclo[3.1.0]hexane (Formula CXV : C$_p$H$_{2p}$ is a valence bond in the meta position, G is n-pentyl, R$_2$ and R$_{42}$ are hydrogen, and ~ is endo).

(I). Refer to Chart L, steps (e) and (f). The Wittig ylid reagent is prepared in 10 ml. of benzene from n-hexyltriphenylphosphonium bromide (0.79 g.) and n-butyllithium (0.6 ml. of 2.32 M. solution in hexane) at about 25° C. for 0.5 hr. After the precipitated lithium bromdie has settled, the solution is removed and added to a cold (0° C.) slurry of the formula-CXIII aldehyde (Examples 38, 0.37 g.). After 15 min. there is added 1.0 ml. of acetone and the mixture is heated to 60° C. for 10 min. The mixture is concentrated under reduced pressure. The residue is washed with 10% ethyl acetate in Skellysolve B and these washings are concentrated to the formula-CXIV title compound, an oil, 0.33 g. having NMR peaks at 1.18, 1.33, 0.6–3.2, 4.5–6.0 and 6.67–7.62 δ; and R$_f$ 0.78 (TLC on silica gel in 25% ethyl acetate in Skellysolve B).

(II.) The above product of part (I) is transformed to the formula-CXV diol by treatment with sodium methoxide (2.5 ml. of a 25% solution in methanol) for 4 hr., followed by addition of 0.5 g. of solid sodium methoxide and further stirring for 15 hr. at 25° C., then at reflux for 6 hr. The mixture is cooled, mixed with 300 ml. of brine, and extracted with ethyl acetate. The organic phase is washed with brine, dried over magnesium sulfate, and concentrated under reduced pressure to a residue, 0.27 g. The residue is subjected to silica gel chromatography, eluting with 25–35% ethyl acetate in Skellysolve B, to yield the formula-CXV title compound an an oil, 0.21 g., having NMR peaks at 0.87, 0.6–3.25, 3.88–4.35, 4.82–5.92, and 6.47–7.33 δ; and R$_f$ 0.13 (TLC on silica gel in 25% ethyl acetate in Skellysolve B).

Following the procedures of Examples 36, 38, and 39 but replacing the formula CX oxetane with each of those obtained following Example 35, there are obtained successively the corresponding formula-CXI, -CXII, -CXIII, and -CXIV compounds wherein C$_p$H$_{2p}$ and its attachment position on the phenyl ring correspond to the specific aldehydes employed following Example 35. These are obtained in both their endo and exo forms.

Further following the procedures of Example 39, but replacing the Wittig ylid reagent with one prepared from a compound of the formula
Br—P(C$_6$H$_5$)$_3$—CHR$_2$—G
wherein —CHR$_2$—G is each of the following:
—(CH$_2$)$_3$—CH$_3$
—(CH$_2$)$_4$—CH$_3$
—(CH$_2$)$_6$—CH$_3$
—(CH$_2$)$_7$—CH$_3$
—CH(CH$_3$)—(CH$_2$)$_5$—CH$_3$
—CH$_2$—CH(CH$_3$)—(CH$_2$)$_3$—CH$_3$
—CH$_2$—C(CH$_3$)$_2$—(CH$_2$)$_3$—CH$_3$
—CH(CH$_3$)—C(C$_2$H$_5$)$_2$—(CH$_2$)$_3$—CH$_3$
—CH$_2$—CHF—(CH$_2$)$_3$—CH$_3$
—CH$_2$—CF$_2$—(CH$_2$)$_3$—CH$_3$
—CH(CH$_3$)—CF$_2$—(CH$_2$)$_3$—CH$_3$

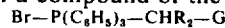

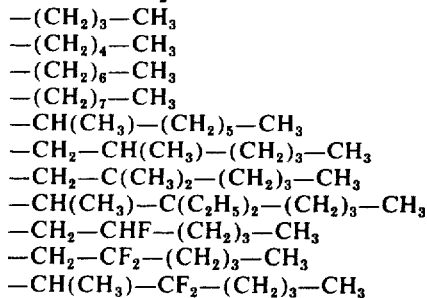

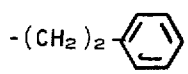

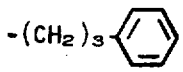

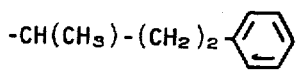

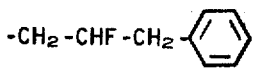

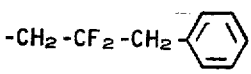

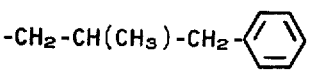

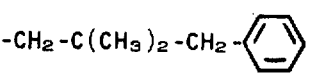

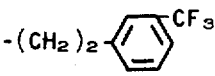

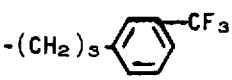

—(CH$_2$)$_2$—C ≡ C—C$_2$H$_5$
—CH$_2$—CH(CH$_3$)—C ≡ C—C$_2$H$_5$
—CH$_2$—C(CH$_3$)$_2$—C ≡ C—C$_2$H$_5$
or
—CH(CH$_3$)—CH$_2$—C ≡ C—C$_2$H$_5$ there are obtained the corresponding compounds within the scope of formula CXIV wherein C$_p$H$_{2p}$ and its attachment to the phenyl ring correspond to the specific compounds of Example 39 and those illustrated in the paragraph immediately thereafter, in both their endo and exo forms.

EXAMPLE 40

2-Exo-{m-[(carboxy)methoxy]}-3-exo-hydroxy-6-endo-(cis-1-heptenyl)bicyclo[3.1.0]hexane (Formula CXVI : C$_p$H$_{2p}$ is a valence bond with attachment in the meta position, G is n-pentyl, R$_1$, R$_2$, and R$_{42}$ are hydrogen, and ~ is endo).

Refer to Chart L, step (g). The formula-CXV diol, i.e. 2-exo-(m-hydroxybenzyl)-3-exo-hydroxy-6-endo-(cis-1-hepentyl)bicyclo[3.1.0]hexane (Example 39, 0.19 g.) is treated in 8 ml. of dioxane with bromoacetic acid (0.61 g.) and 6 ml. of 1N. aqueous sodium hydroxide. After the mixture has been heated at reflux for 3 hr., with sodium hydroxide solution added when necessary to maintain a pH of about 10, the mixture is cooled, diluted with 100 ml. of water, and extracted with diethyl ether. The aqueous phase is acidified to pH 1–2 and extracted with ethyl acetate to yield the formula-CXVI title compound, a pale yellow oil, 0.20 g. Recovered formula- CXV diol is obtained from the diethyl ether organic phase on drying and concentrating, 0.025 g.

Following the procedures of Example 40 but replacing bromoacetic acid with a haloacetate within the scope of Hal—$CH_2$—$COOR_1$ as defined herein and specifically illustrated as follows Cl—$CH_2$—$COOCH_3$
Br—$CH_2$—$COOC_2H_5$
Cl—$CH_2$—$COOC_8H_{17}$(n)
I—$CH_2$—$COOCH_2C_6H_5$
Cl—$CH_2$—COO(m-Cl—$C_6H_4$)

there are obtained the corresponding formula-CXVI compounds wherein $R_1$ is respectively methyl, ethyl, n-octyl, benzyl, and m-chlorophenyl.

Likewise following the procedures of Example 40 with each of the formula-CXIV compounds disclosed following Example 39 and using each of the haloacetates specifically identified above, there are obtained the corresponding formula-CXVI compounds.

EXAMPLE 41

3-Oxa-3,7-inter-m-phenylene-4,5,6-trinor-$PGF_{1\alpha}$ (Formula CI : $C_pH_{2p}$ is a valence bond with attachment in the meta position, $R_{30}$ is n-pentyl, and $R_1$ and $R_2$ are hydrogen).

(I.) Refer to Chart L. The formula-CXVI alkene is transformed to the title compound applying the procedures disclosed in U.S. Pat. No. 3,711,515. Thus, compound CXVI (Example 40) is hydroxylated by the procedures of Example 39 of that patent to the formula-CXVII glycol of Chart L, using osmium tetroxide either alone or in combination with N-methylmorpholine oxide-hydrogen peroxide complex.

The glycol is then either (1) sulfonated, for example to yield the bismesylate, and then hydroyzed to a mixture of the title compound and its 15-epimer, applying the procedures of Example 7 of that patent, or (2) treated with substantially 100% formic acid to form the diformate of CI and thereafter hydroyzed to a mixture of the title compound and its 15 epimer, applying the procedures of Examples 20 and 21 of that patent. The epimers are separated by silica gel chromatography to yield the title compound and its 15-epimer.

(II). A third route from glycol CXVII to the title compound is by way of a formula-CXX cyclic ortho ester

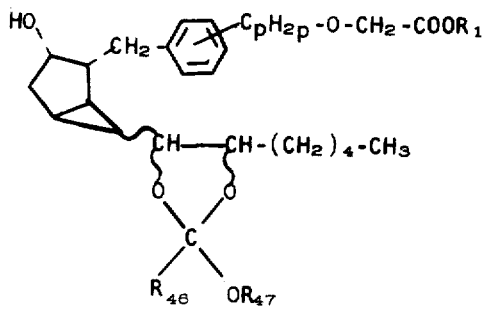

wherein $C_pH_{2p}$, $R_{46}$, $R_{47}$ and ~ are as defined above. The glycol CXVII is treated as a 1–20% solution in benzene with trimethyl orthoformate (1.5–10 molar equivalents) and a catalytic amount (1% of the weight of the glycol) of pyridine hydrochloride at about 25°C. The reaction is followed by TLC (thin layer chromatography) and is complete in a few minutes. There is thus obtained the formula-CXX cyclic ortho ester in 100% yield.

The cyclic ortho ester is then treated with 20 volumes of 100% formic acid at about 25° C. In about 10 min. the reaction mixture is quenched in water or aqueous alkaline bicarbonate solution and extracted with dichloromethane. The organic phase is shaken with 5% aqueous sodium bicarbonate, dried over sodium sulfate, and concentrated to yield the formula CXXI diester, in this example identical with the diformate of compound CI. The diformate is contacted with 10–50 volumes of anhydrous methanol and 10–20% of its weight of potassium carbonate at about 25° C. until the formyl groups are removed. The mixture of 15-epimers thus obtained is then separated to yield the formula-CI title compound and its 15-epimer.

Following the procedures of Example 41, each of the formula- CXVI alkenes disclosed following Example 40 is converted into the corresponding oxa-phenylene PGF analog and its 15-epimer. There are likewise formed the corresponding oxa-phenylene 17,18-didehydro-PGF analogs as shown in Chart N.

EXAMPLE 42

2-Exo-[m-(carboxymethoxy)benzyl]-3-exohydroxy-6-endo-(cis-1-heptenyl)bicyclo-[3.1.0]hexane (Formula CXXVII: $C_pH_{2p}$ is a valence bond with attachment in the meta position, G is n-pentyl, $R_1$ and $R_2$ are hydrogen, and ~ is endo).

Refer to Chart M, steps (a)-(f). There is first prepared the formula-CXXII oxetane. Following the procedures of Examples 34 and 35 but replacing the m-acetoxybenzaldehyde of Example 35 with an aldehyde within the scope of

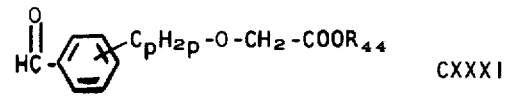

as to $C_pH_{2p}$, the attachment position on the phenyl ring, and the carboxyl group $R_{44}$, as defined above, the corresponding formula-CXXII oxetanes are obtained with a fully developed side chain. Specifically, the following formula-CXXXI aldehydes are employed:

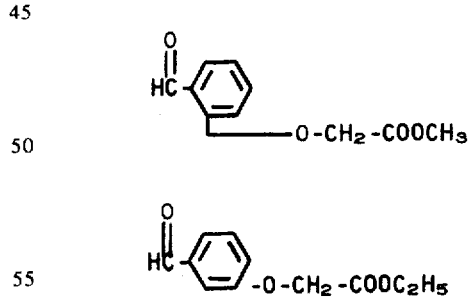

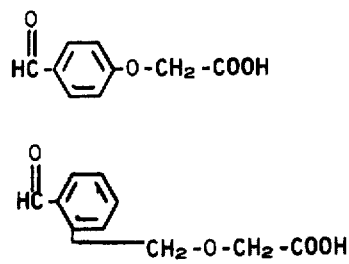

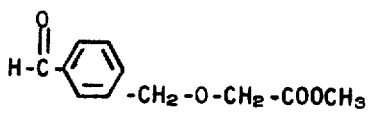

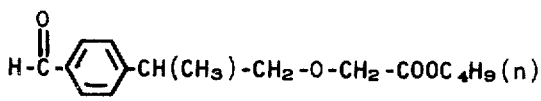

and

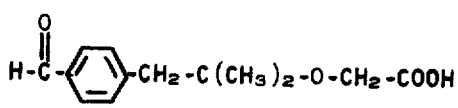

Thereafter, following the procedures of Examples 36, 38, and 39, but replacing the formula-XX octane of Example 36 with those obtained by the procedure disclosed in the above paragraph of this example, there are obtained the corresponding formula-CXXVI products. Likewise following those procedures of Examples 36, 38, and 39, but replacing the Wittig ylid reagent of Example 39 with each one disclosed after Example 39, and applying it to each of the above formula-CX compounds of this example, there are obtained the corresponding formula-CXXVI compounds with those specific sidechains.

Finally, the blocking groups on each CXXVI compound are removed by methods disclosed herein or known in the art to yield the formula-CXXVII title compound and the corresponding formula-CXXVII compounds from those formula-CXXVI compounds above.

EXAMPLE 43

2-Exo-{m-[(methoxycarbonyl)methoxy]benzyl}-3-exo hydroxy-6-endo-(cis-1-heptenyl)bicyclo[3.1.0]hexane (Formula-CXXVII: $C_pH_{2p}$ is a valence bond with attachment in the meta position, G is n-pentyl, $R_1$ is methyl, $R_2$ is hydrogen, and ~ is endo).

Refer to Chart M. The formula-CXXVII acid (Example 40, 0.20 g.) is treated in methanol solution at 0° C. with a solution of diazomethane in diethyl ether (prepared from N-methyl-N-nitroso-N′-nitroguanidine (2.0 g.) and potassium hydroxide (6 ml. of 40% aqueous solution)) until a permanent yellow color is produced, and the mixture is concentrated to yield the title compound, a pale tan oil.

EXAMPLE 44

1-6-Endo-(cis-1-heptenyl)-2-exo-{m-[(methoxycarbonyl)methoxy]benzyl}bicyclo[3.1.0]hexan-3-one (Formula CXXVIII: $C_pH_{2p}$ is a valence bond with attachment in the meta position, G is n-pentyl, $R_1$ is methyl, $R_2$ is hydrogen, and ~ is endo).

Refer to Chart M, step (g). The formula-CXXVII methyl ester is oxidized to the bicyclic hexanone as follows. The formula-CXXVII methyl ester (Example 41, 0.21 g.) is added in 2 ml. of dichloromethane to a solution of Collins reagent (prepared from pyridine (0.53 g.) and chromium trioxide (0.34 g.) in 10 ml. of dichloromethane) at about 25° C. for 15 min. The mixture is then shaken with a mixture of 60 ml. of diethyl ether, ice, and 25 ml. of 1 N. aqueous sodium hydroxide, and the organic phase is separated. The organic phase is washed with 1 N. aqueous sodium hydroxide, 1.2 N. aqueous hydrochloric acid, and brine, dried, and concentrated under reduced pressure. The residue, a colorless oil, 0.19 g., is subjected to silica gel chromatography, eluting with 5–20% ethyl acetate in Skellysolve B. There is thus obtained the formula-CXXVIII title compound, a colorless oil, 0.13 g., having NMR peaks at 0.87, 0.6–3.3, 3.77, 4.60, 4.5–5.1, 5.37–5.95, and 6.58–7.40 $\delta$; $[\alpha]_D$ −39° (C=0.8380 in 95% ethanol); and $R_f$ 0.42 (TLC on silica gel in 25% ethyl acetate in Skellysolve B).

Following the procedures of Examples 43 and 44, each of the above-identified formula-CXXVII compounds following Example 42 is oxidized to the corresponding formula-CXXVIII compound.

EXAMPLE 45

3-Oxa-3,7-inter-m-phenylene-4,5,6-trinor-PGE$_1$, Methyl Ester (Formula-XCVII: $C_pH_{2p}$ is a valence bond with attachment in the meta position, $R_1$ is methyl, $R_{30}$ is n-pentyl, and $R_2$ is hydrogen).

Following the procedures of Example 41, the formula-CXXVIII alkene is transformed in several steps to the title compound.

Likewise, following the same procedures, each of the formula-CXXVIII alkenes disclosed following Example 44 is converted into the corresponding oxa-phenylene PGE analog and its 15epimer.

Following the procedures of Examples 34–45, each of the endo intermediates is replaced by the corresponding exo intermediate to yield the corresponding exo intermediate or the ultimate oxa-phenylene PG analog.

Likewise following the procedures of Examples 34–45, each of the optically active isomers is replaced by the corresponding racemic mixture to yield the corresponding racemic intermediate or ultimate oxa-phenylene PG analog.

I claim:

1. An optically active compound of the formula:

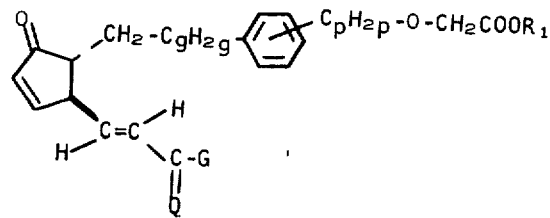

or a racemic mixture of that compound and the enantiomer thereof, wherein $C_gH_{2g}$ represents a valence bond or alkylene of one to 4 carbon atoms, inclusive, with one to 4 carbon atoms, inclusive, with one or 2 chain carbon atoms between —CH$_2$— and the ring; wherein $C_pH_{2p}$ represents a valence bond or alkylene of one to 4 carbon atoms between the ring and the —O—; wherein $C_gH_{2g}$ and $C_pH_{2p}$ together represent zero to 8 carbon atoms, inclusive, with total chain lengths zero to 3 carbon atoms, inclusive; wherein G is (1) alkyl of 2 to 10 carbon atoms, inclusive, substituted with zero, one, 2, or 3 fluoro or (2) a mono-valent moiety of the formula

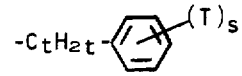

wherein $C_tH_{2t}$ represents a valence bond or alkylene of one to 10 carbon atoms, inclusive, substituted with zero, one, or 2 fluoro, with one to 7 carbon atoms, inclusive, between

and the ring, wherein T is alkyl of one to 4 carbon atoms, inclusive, fluoro, chloro, trifluoromethyl, or —OR$_6$, wherein R$_6$ is hydrogen or alkyl of one to 4 carbon atoms, inclusive, and wherein s is zero, one, 2, or 3, with the proviso that not more than two T's are other than alkyl; wherein Q is

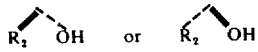

wherein R$_2$ is hydrogen or alkyl of one to 4 carbon atoms, inclusive; and wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive; including the lower alkanoates thereof and the pharmacologically acceptable salts thereof when R$_1$ is hydrogen.

2. A compound according to claim 1 wherein G is alkyl of 2 to 10 carbon atoms, inclusive, substituted with zero, one, 2, or 3 fluoro.

3. A compound according to claim 2 wherein Q is

4. A compound according to claim 3 wherein R$_1$ is hydrogen or alkyl of one to 12 carbon atoms.

5. A compound according to claim 3 wherein R$_1$ is hydrogen, methyl, or ethyl.

6. A compound according to claim 4 wherein R$_2$ is hydrogen.

7. A compound according to claim 4 wherein R$_2$ is methyl or ethyl.

8. A compound according to claim 4 wherein C$_g$H$_{2g}$ is a valence bond.

9. A compound according to claim 8 wherein C$_p$H$_{2p}$ is methylene.

10. A compound according to claim 8 wherein C$_p$H$_{2p}$ is a valence bond.

11. A compound according to claim 10 wherein G is

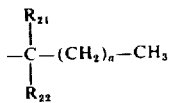

wherein a is one, 2, 3, 4, or 5, and wherein R$_{21}$ and R$_{22}$ are hydrogen, alkyl of one to 4 carbon atoms, inclusive, or fluoro, being the same or different, with the proviso that R$_{22}$ is fluoro only when R$_{21}$ is hydrogen or fluoro.

12. A compound according to claim 11 wherein a is 2, 3, or 4, and wherein R$_{21}$ and R$_{22}$ are hydrogen, methyl, ethyl, or fluoro, being the same or different.

13. 3-Oxa-3,7-inter-m-phenylene-4,5,6-trinor-PGA$_1$, a compound according to claim 10.

14. 3-Oxa-3,7-inter-m-phenylene-4,5,6-trinor-PGA$_1$, methyl ester, a compound according to claim 10.

15. 15(S)-15-Methyl-3-oxa-3,7-inter-m-phenylene-4,5,6-trinor-PGA$_1$, a compound according to claim 10.

16. 16,16-Dimethyl-3-oxa-3,7-inter-m-phenylene-4,5,6-trinor-PGA$_1$, a compound according to claim 10.

17. A compound according to claim 1 wherein G is a monovalent moiety of the formula

wherein C$_t$H$_{2t}$ represents a valence bond or alkylene of one to 10 carbon atoms, inclusive, substituted with zero, one, or 2 fluoro, with one to 7 carbon atoms, inclusive, between

and the ring, wherein T is alkyl of one to 4 carbon atoms, inclusive, fluoro, chloro, trifluoromethyl, or —OR$_6$, wherein R$_6$ is hydrogen or alkyl of one to 4 carbon atoms, inclusive, and wherein s is zero, one, 2, or 3, with the proviso that not more than two T's are other than alkyl.

18. A compound according to claim 17 wherein ~ indicates attachment of the side chain to the cyclopentane ring in alpha configuration.

19. A compound according to claim 18 wherein Q is

20. A compound according to claim 19 wherein R$_1$ is hydrogen or alkyl of one to 12 carbon atoms.

21. A compound according to claim 19 wherein R$_1$ is hydrogen, methyl, or ethyl.

22. A compound according to claim 20 wherein R$_2$ is hydrogen.

23. A compound according to claim 20 wherein R$_2$ is methyl or ethyl.

24. A compound according to claim 20 wherein C$_g$H$_{2g}$ is a valence bond.

25. A compound according to claim 24 wherein C$_p$H$_{2p}$ is methylene.

26. A compound according to claim 24 wherein C$_p$H$_{2p}$ is a valence bond.

27. A compound according to claim 26 wherein G is

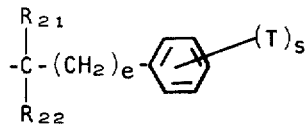

wherein e is zero, one, 2, or 3; wherein R$_{21}$ and R$_{22}$ are hydrogen, alkyl of one to 4 carbon atoms, inclusive, or fluoro, being the same or different, with the proviso that R$_{22}$ is fluoro only when R$_{21}$ is hydrogen or fluoro; wherein T is alkyl of one to 4 carbon atoms, inclusive, fluoro, chloro, trifluoromethyl, or —OR$_6$, wherein R$_6$ is hydrogen or alkyl of one to 4 carbon atoms, inclusive, and wherein s is zero, one, 2, or 3, with the proviso that not more than two T's are other alkyl.

28. A compound according to claim 27 wherein R$_{21}$ and R$_{22}$ are hydrogen, methyl, ethyl, or fluoro, being the same or different.

29. 3-Oxa-3,7-inter-m-phenylene-17-phenyl-4,5,6,18,19,20-hexanor-PGA$_1$, a compound according to claim 26.

30. 15(S)-15-Methyl-3-oxa-3,7-inter-m-phenylene-17-phenyl-4,5,6,18,19,20-hexanor-PGA$_1$, a compound according to claim 26.

* * * * *